US012187696B2

(12) United States Patent
Le et al.

(10) Patent No.: US 12,187,696 B2
(45) Date of Patent: Jan. 7, 2025

(54) UREA MOTIF CONTAINING COMPOUNDS AND DERIVATIVES THEREOF AS ANTIBACTERIAL DRUGS

(71) Applicant: Technische Universität München, Munich (DE)

(72) Inventors: Philipp Le, Munich (DE); Stephan Sieber, Utting am Ammersee (DE); Elena Kunold, Sundbyberg (SE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 614 days.

(21) Appl. No.: 16/304,521

(22) PCT Filed: May 30, 2017

(86) PCT No.: PCT/EP2017/063014
§ 371 (c)(1),
(2) Date: Nov. 26, 2018

(87) PCT Pub. No.: WO2017/207556
PCT Pub. Date: Dec. 7, 2017

(65) Prior Publication Data
US 2021/0009550 A1    Jan. 14, 2021

(30) Foreign Application Priority Data
May 30, 2016   (EP) .................................... 16171906

(51) Int. Cl.
| C07D 317/66 | (2006.01) |
| A61P 31/04 | (2006.01) |
| C07C 275/34 | (2006.01) |
| C07C 275/38 | (2006.01) |
| C07C 275/42 | (2006.01) |
| C07D 317/46 | (2006.01) |

(52) U.S. Cl.
CPC ............ C07D 317/66 (2013.01); A61P 31/04 (2018.01); C07C 275/34 (2013.01); C07C 275/38 (2013.01); C07C 275/42 (2013.01); C07D 317/46 (2013.01)

(58) Field of Classification Search
CPC ................ C07D 317/66; C07D 317/46; C07C 275/34; C07C 275/38; C07C 275/42
See application file for complete search history.

(56) References Cited

U.S. PATENT DOCUMENTS

| 3,503,886 | A | * | 3/1970 | Noel ....................... A01N 31/12 510/501 |
| 3,579,578 | A | * | 5/1971 | Nikawitz .............. C07C 275/30 564/53 |
| 5,985,795 | A | * | 11/1999 | Suganuma ............. A01N 59/26 504/121 |
| 6,207,679 | B1 | * | 3/2001 | Cuny ................... C07D 209/14 514/312 |
| 2004/0102636 | A1 | | 5/2004 | Miller et al. |
| 2009/0082395 | A1 | * | 3/2009 | Gless, Jr. ............. C07D 317/46 514/313 |
| 2010/0048573 | A1 | * | 2/2010 | Sperandio .............. A61K 31/17 514/239.5 |
| 2015/0335594 | A1 | | 11/2015 | Choudhary et al. |

FOREIGN PATENT DOCUMENTS

| CN | 103130686 A | 6/2013 | |
| GB | 921682 A * | 3/1963 | ............. A01N 47/30 |
| JP | 2-500371 A | 3/1989 | |
| JP | 10-109912 A | 4/1998 | |
| JP | 2010 528098 A | 8/2010 | |
| KR | 20030080509 A * | 10/2003 | |
| WO | 89/00563 A | 1/1989 | |
| WO | WO-9900357 A1 * | 1/1999 | ........... C07C 275/28 |
| WO | 0032196 A2 | 6/2000 | |
| WO | 02/055661 A2 | 7/2002 | |
| WO | WO-2005009944 A1 * | 2/2005 | ............. A61P 31/00 |
| WO | WO-2006049941 A2 * | 5/2006 | ............. A61K 31/17 |
| WO | 2007/101710 A1 | 9/2007 | |
| WO | WO-2007141423 A1 * | 12/2007 | ........... C07C 233/29 |
| WO | 2008/146030 A1 | 12/2008 | |
| WO | 2009/035951 A2 | 3/2009 | |
| WO | 2009/088549 A2 | 7/2009 | |
| WO | 2009/088549 A3 | 7/2009 | |
| WO | 2010123591 A2 | 10/2010 | |
| WO | 2013/142628 A2 | 9/2013 | |
| WO | 2013/142628 A3 | 9/2013 | |
| WO | 2013/142628 A4 | 9/2013 | |
| WO | 2014089226 A1 | 6/2014 | |
| WO | 2015/051149 A2 | 4/2015 | |

OTHER PUBLICATIONS

CAS Registry No. 1351833-31-2, which entered STN on Dec. 23, 2011 (Year: 2011).*
CAS Registry No. 1261004-24-3, which entered STN on Jan. 28, 2011 (Year: 2011).*
CAS Registry No. 1241992-25-5, which entered STN on Sep. 17, 2010 (Year: 2010).*
CAS Registry No. 1241968-93-3, which entered STN on Sep. 17, 2010 (Year: 2010).*
CAS Registry No. 904498-66-4, which entered STN on Aug. 25, 2006 (Year: 2006).*
CAS Registry No. 894163-24-7, which entered STN on Jul. 18, 2006 (Year: 2006).*
CAS Registry No. 892771-20-9, which entered STN on Jul. 16, 2006 (Year: 2006).*
CAS Registry No. 701945-67-7, which entered STN on Jul. 1, 2004 (Year: 2004).*
Bone et al. JAMA 1992, 268, 3452-3455 (Year: 1992).*
Phetsuksiri et al. Antimicrobial Agents and Chemotherapy 1999, 43, 1042-1051 (Year: 1999).*

(Continued)

Primary Examiner — Matthew P Coughlin
(74) Attorney, Agent, or Firm — SALIWANCHIK, LLOYD & EISENSCHENK

(57) ABSTRACT

The invention relates to compounds which are suitable for treating bacterial diseases and to pharmaceutical compositions containing such compounds. The invention further relates to a kit of parts comprising such compounds and to the use of such compounds as disinfectants.

10 Claims, 16 Drawing Sheets

Specification includes a Sequence Listing.

(56) References Cited

OTHER PUBLICATIONS

Fluit et al. Clin Microbiol Infect 2012, 18, 735-744 (Year: 2012).*
Smith et al. J. Med. Microbiol. 2001, 50, 940-946 (Year: 2001).*
Huovinen et al. Toxicology in Vitro 2015, 29, 1577-1586 (Year: 2015).*
Zhang et al. ACS Med. Chem. Lett. 2010, 1, 460-465 and its supporting information (Year: 2010).*
Nguyen et al. Emerging Infection Diseases 2005, 11, pp. 526-532 (Year: 2005).*
Chang, Han-Chu et al. "In vitro and in vivo activity of a novel sorafenib derivative SC5005 against MRSA," J. Antimicrob Chemother, 71:449-459, 2016 (advance access publication Nov. 8, 2015).
Choi, Seoung-Ryoung et al. "Development of potential broad spectrum antimicrobials using C2-symmetric 9-fluorenone alkyl amine," Bioorganic & Medicinal Chemistry Letters, 26:1997-1999, 2016.
Francisco, Gerardo D. et al. "Phenyl thiazolyl urea and carbamate derivatives as new inhibitors of bacterial cell-wall biosynthesis," Bioorganic & Medicinal Chemistry Letters, 14:235-238, 2004.
Pandurangan, Komala et al. "Supramolecular pyridyl urea gels as soft matter with antibacterial properties against MRSA and/or E. coli," Chem. Commun., 50:10819-10822, 2014.
Lourenco, A.L. et al. "Synthesis and Antiplatelet Activity of Antithrombotic Thiourea Compounds: Biological and Structure-Activity Relationship Studies" Molecules, 2015, pp. 7174-7200, vol. 20.
Ricci, A. et al. "Cytokinin-like activity of N,N'-diphenylureas. N, N'-bis(2,3-methylenedioxyphenyl)urea and N, N'-bis-(3,4-methylenedioxyphenyl)urea enhance adventitious root formation in apple rootstock M26 (*Malus pumila* Mill.)" Plant Sciences, 2001, pp. 1055-1065, vol. 160.
Database Registry [online] Chemical Abstract Service, US; Retrieved from STN, RN 1261004-24-3, Jan. 28, 2011, N-1,3-benzodioxol-5-yl-N'-(4-fluoro-3-methylphenyl)thiourea.
Database Registry [online] Chemical Abstract Service, US; Retrieved from STN, RN 1241992-25-5, Sep. 17, 2010, N-1,3-benzodioxol-5-yl-N'-(4-chloro-3-methylphenyl)urea.
Database Registry [online] Chemical Abstract Service, US; Retrieved from STN, RN 1241968-93-3, Sep. 17, 2010, N-1,3-benzodioxol-5-yl-N'-(4-fluoro-3-methylphenyl)urea.
Database Registry [online] Chemical Abstract Service, US; Retrieved from STN, RN 904498-66-4, Aug. 25, 2006, N-1,3-benzodioxol-5-yl-N'-[4-chloro-3-(trifluoromethyl)phenyl]thio urea.
Database Registry [online] Chemical Abstract Service, US; Retrieved from STN, RN 894163-24-7, Jul. 18, 2006, N-1,3-benzodioxol-5-yl-N'-(4-bromo-3-methylphenyl)urea.
Database Registry [online] Chemical Abstract Service, US; Retrieved from STN, RN 892771-20-9, Jul. 16, 2006, N-1,3-benzodioxol-5-yl-N'-(4-bromo-3-methylphenyl)thiourea.
Database Registry [online] Chemical Abstract Service, US; Retrieved from STN, RN 701945-67-7, Jul. 1, 2004, N-1,3-benzodioxol-5-yl-N'-[4-chloro-3-(trifluoromethyl)phenyl]urea.
Database Registry [online] Chemical Abstract Service, US; Retrieved from STN, RN 1351833-31-2, Dec. 23, 2011, N-1,3-benzodioxol-5-yl-N'-(4-chloro-3-methylphenyl)thiourea.
Bielenica, A. et al. "Synthesis, cytotoxicity and antimicrobial activity of thiourea derivatives incorporating 3-(trifluoromethyl)phenyl moiety" European Journal of Medicinal Chemistry, 2015, pp. 111-125, vol. 101.
Fujikawa, F. et al. "Studies on Chemotherapeutic Agents Against *Mycobacterium tuberculosis*. XXVI, Synthesis and Antituberculous Activity of Phenylthiourea, p-Ethoxyphenyl-thiourea and 3-Bromo-4-ethoxyphenylthiourea Derivatives" Kyoto University, 1971, pp. 1-8, vol. 91.
Office Action issued by the Japanese Patent Office in parallel Japanese Patent Application No. 2018-562297 dated Mar. 6, 2021 with English translation.
2nd Written Opinion issued by the Singapore Patent Office in the parallel Singapore Patent Application No. 11201809537V issued Aug. 3, 2021.

* cited by examiner

PK/X17-1-058
MIC 10 µM

| Cell line | A549 | HeLa | NIH/3T3 | HepG2 |
|---|---|---|---|---|
| Compound | | | | |
| Sorafenib | 1.27 ± 0.056 | 0.978 ± 0.031 | 0.879 ± 0.026 | 0.230 ± 0.147 |
| PK/X17-2-011 | 2.02 ± 0.103 | 1.78 ± 0.111 | - | 1.11 ± 0.268 |
| PK/X17-1-150 | 0.971 ± 0.056 | 0.798 ± 0.098 | 0.899 ± 0.039 | 1.02 ± 0.100 |
| PK/X17-4-011 | 1.78 ± 0.303 | 1.41 ± 0.435 | - | 1.05 ± 0.062 | values given as a function of $\log_{10}$ [μM]

PK/X17-4-011
MIC >100 μM

PK/X17-1-150
MIC 0.3 μM

PK/X17-2-011
MIC >100 μM

Sorafenib
MIC 3 μM

* highest tested concentration 40x MIC

PK/X17-1-150
MIC 0.3 µM

A fluorescent peptide cleavage

SpsB

Sec

B

SpsB
DABCYL–AGHDAHASET–EDANS
ca. 40 Å

C

PK/X17-1-150
MIC 0.3 µM

A

B

UREA MOTIF CONTAINING COMPOUNDS AND DERIVATIVES THEREOF AS ANTIBACTERIAL DRUGS

CROSS REFERENCE TO RELATED APPLICATIONS

This application is a National Stage Application of International Application Number PCT/EP2017/063014, filed May 30, 2017; which claims priority to European Patent Application No. 16171906.7, filed May 30, 2016.

The Sequence Listing for this application is labeled "SeqList-14Nov18-ST25.txt", which was created on Nov. 14, 2018 and is 1 KB. The entire content is incorporated herein by reference in its entirety.

The invention relates to compounds which are suitable for treating bacterial diseases and to pharmaceutical compositions containing such compounds. The invention further relates to a kit of parts comprising such compounds and to the use of such compounds as disinfectants.

The rise of multi-drug resistant bacterial pathogens poses a severe threat for human health. In particular multi-resistant strains of the opportunistic pathogen *Staphylococcus aureus* have become a global problem. In the US 14% (11,285 out of 80,461) of patients hospitalized with invasive methicillin-resistant *S. aureus* (MRSA) infections died due to lacking treatment options in 2011 (Centers for Disease Control and Prevention (CDC). Antibiotic resistance threats in the United States, 2013. Atlanta: CDC; 2013. Available from: http://www.cdc.gov/drugresistance/threat-report-2013/pdf/ar-threats-2013-508.pdf). Today MRSA causes more deaths in the USA each year than HIV/AIDS, Parkinson's disease, emphysema and homicide combined (Ventola, C. L. *P T* 2015, 40 (4), 277-283). Given this scenario it is surprising to note that with the exception of the 1,3-oxazolidinone linezolid and the lipopeptide daptomycin there have been no novel antibacterial classes with clinical relevance discovered since 1970 (Walsh, C.; Wright, G. *Chem. Rev.* 2005, 105 (2), 391-394). This innovation gap combined with the emergence of bacterial strains resistant to current antibiotics is the main reason for the current crisis of antibacterial chemotherapy that threatens to return the treatment of bacterial infections to the 'dark age' of the pre-antibiotic era (Niccolai, D.; Tarsi, L.; Thomas, R. J. *Chem. Commun.* 1997, 24, 2333-2342 and Michael, C. A.; Dominey-Howes, D.; Labbate, M. *Front. Public Heal.* 2014, 2, 145). In view of this urgency many resources have been committed to improve existing antibiotic classes. However, it was recently suggested to refocus on the identification of new classes of antibiotic lead structures that address novel yet unexploited cellular targets, rather than to further optimize existing antibiotics that address a limited set of bacterial targets (bacterial cell wall biosynthesis, protein biosynthetic pathways, folate coenzyme biosynthesis, and DNA replication and repair) (Walsh, C.; Wright, G. *Chem. Rev.* 2005, 105 (2), 391-394; Lange, R. P.; Locher, H. H.; Wyss, P. C.; Then R. L. *Curr. Pharm. Des.* 2007, 13 (30), 3140-3154; Donadio, S.; Maffioli, S.; Monciardini, P.; Sosio, M.; Jabes, D. *J. Antibiot. (Tokyo).* 2010, 63 (8), 423-430; Gwynn, M. N.; Portnoy, A.; Rittenhouse, S. F.; Payne, D. J. *Ann. N. Y. Acad. Sci.* 2010, 1213, 5-19; Fischbach, M. A.; Walsh, C. T. *Science* 2009, 325 (5944), 1089-1093 and Payne, D. J.; Gwynn, M. N.; Holmes, D. J.; Pompliano, D. L. *Nat. Rev. Drug Discov.* 2007, 6 (1), 29-40).

The rapid emergence of resistance of pathogens is understood to be correlated to a liberal and widespread use of antibiotics as a result of overprescription and inappropriate, extensive medication as well as arbitrary use in farming industry. In order to survive antibacterial treatment bacteria have developed several strategies, namely the destruction of the antibiotic by bacterial enzymes, target modification to lower its susceptibility to the active agent and the reduction of the effective antibiotic concentration within the cell below toxic threshold concentrations by either an increased expression of efflux pumps, restricted penetration and/or by over-expression of the cellular target (Ventola, C. L. P T 2015, 40 (4), 277-283; Walsh, C.; Wright, G. *Chem. Rev.* 2005, 105 (2), 391-394 and Blair, J. M. A.; Webber, M. A.; Baylay, A. J.; Ogbolu, D. O.; Piddock, L. J. V. *Nat. Rev. Microbiol.* 2014, 13 (1), 42-51). Furthermore, there is the phenomenon of cross-resistances, which means that bacteria under drug treatment often become resistant to other antibiotics without direct contact to those ones. This is due to the limited set of currently exploited bacterial targets, which might mutate upon selection pressure and therefore become insensitive to several antibiotics at the same time. Examples of resistance development are known since the first days of antibiotic treatment. For example for penicillin which was first prescribed to treat serious infections in the 1940s, first resistant strains were observed shortly after. Another example is vancomycin: here first resistant strains of staphylococci were described in 1979 and 1983 only a few years after vancomycin was introduced to clinical practice in 1972 (Sengupta, S.; Chattopadhyay, M. K.; Grossart, H.-P. *Front. Microbiol.* 2013, 4, 47). Unfortunately, resistance has been observed to nearly all antibiotic agents of clinical relevance today.

Sorafenib (Nexavar, BAY 43-9006) is an approved human kinase inhibitor with oral bioavailability for the treatment of advanced renal cell carcinoma (RCC), unresectable hepatocellular carcinomas (HCC) and thyroid cancer. It targets several tyrosine [VEGFR2 ($IC_{50}$ 90 nM), PDGFRβ ($IC_{50}$ 57 nM), FLT3 ($IC_{50}$ 58 nM) and c-Kit ($IC_{50}$ 68 nM)] as well as serine/threonine kinases [Raf-1 ($IC_{50}$ 6 nM), and B-Raf ($IC_{50}$ 22 nM)] in a reversible manner by binding into the ATP-binding pocket and thereby outcompeting ATP (Wilhelm, S.; Carter, C.; Lynch, M.; Lowinger, T.; Dumas, J.; Smith, R. A.; Schwartz, B.; Simantov, R.; Kelley, S. *Nat. Rev. Drug Discov.* 2006, 5 (10), 835-844; Wilhelm, S. M.; Carter, C.; Tang, L.; Wilkie, D.; McNabola, A.; Rong, H.; Chen, C.; Zhang, X.; Vincent, P.; McHugh, M.; Cao, Y.; Shujath, J.; Gawlak, S.; Eveleigh, D.; Rowley, B.; Liu, L.; Adnane, L.; Lynch, M.; Auclair, D.; Taylor, I.; Gedrich, R.; Voznesensky, A.; Riedl, B.; Post, L. E.; Bollag, G.; Trail, P. A. *Cancer Res.* 2004, 64 (19), 7099-7109; Liu, L.; Cao, Y.; Chen, C.; Zhang, X.; McNabola, A.; Wilkie, D.; Wilhelm, S.; Lynch, M.; Carter, C. *Cancer Res.* 2006, 66 (24), 11851-11858; Ricci, M. S.; Kim, S.-H.; Ogi, K.; Plastaras, J. P.; Ling, J.; Wang, W.; Jin, Z.; Liu, Y. Y.; Dicker, D. T.; Chiao, P. J.; Flaherty, K. T.; Smith, C. D.; El-Deiry, W. S. *Cancer Cell* 2007, 12 (1), 66-80; Wilhelm, S. M.; Adnane, L.; Newell, P.; Villanueva, A.; Llovet, J. M.; Lynch, M. *Mol. Cancer Ther.* 2008, 7 (10), 3129-3140; Smalley, K. S. M.; Xiao, M.; Villanueva, J.; Nguyen, T. K.; Flaherty, K. T.; Letrero, R.; Van Belle, P.; Elder, D. E.; Wang, Y.; Nathanson, K. L.; Herlyn, M. *Oncogene* 2008, 28 (1), 85-94 and Zhang, Y.; Xu, D.; Wang, X.; Lu, M.; Gao, B.; Qiao, X. *Mol. Med. Rep.* 2014, 9 (1), 83-90). Antibiotic growth-suppressing properties of sorafenib and structurally closely related Regorafenib have recently been described in *Salmonella typhimurium*, *Streptococcus pyogenes*, methicillin-resistant *S. aureus* (MRSA), vancomycin-resistant enterococci (VRE), methicillin-resistant *Staphylococcus epidermis* (MRSE), and antibiotic-resistant *Acinetobacter baumanii* (Roberts, J.

L.; Tavallai, M.; Nourbakhsh, A.; Fidanza, A.; Cruz-Luna, T.; Smith, E.; Siembida, P.; Plamondon, P.; Cycon, K. A.; Doern, C. D.; Booth, L.; Dent, P. *J. Cell. Physiol.* 2015, 230 (10), 2552-2578). Roberts et al. suggested that Dna K, a chaperone protein involved in DNA replication, might be one antibiotic target of sorafenib and Regorafenib.

Recently, Chang et al. (2016), J. Antimicrob. Chemother. 71: 449-459 described the in vitro and in vivo activity of sorafenib derivatives against MRSA. The authors found in total five different sorafenib derivatives by two random chemical library syntheses and subsequent screening of library members in an antibacterial assay to determine the inhibitory activity of the randomly made compounds against various bacterial strains. However, Chang et al. have not disclosed any structure activity relationship (SAR) data, making it impossible for the person skilled in the art to dissect the molecules into motifs that are essential for antibacterial activity. The authors only disclose example compounds exhibiting antibiotic effects, however, data on compounds that lack this activity are needed in order to provide a rational for de-novo compound design. Without this information a rational development of derivatives is impossible.

There is still a great need for new small compounds having antibacterial activity for the treatment of bacterial diseases, in particular for the treatment of bacterial diseases caused by bacteria resistant to commonly used antibiotic agents.

The inventors of the present invention have conducted intensive studies and found surprisingly, that the compounds according to Formula I, Formula IA, Formula IB and Formula II, which are described in more detail below, satisfy this need. The compounds according to the present invention are based on an urea motif and show anti-bacterial activity against various bacterial strains, in particular against multi-resistant *Staphylococcus aureus* and clinical isolated thereof (see FIG. 2, Tables 1 and 2), without leading to resistance development (see FIG. 6). Further, they show excellent stability in mouse plasma and no significant rise in cytotoxicity compared to antibacterial compounds like sorafenib (see FIGS. 4 and 5). The inventors found surprisingly, that type I signal peptidase (SpsB) is a protein target of the compounds according to the invention, by using affinity-based protein profiling experiments (AfBPP) in *Staphylococcus aureus* utilizing a photoreactive derivative of sorafenib (see FIG. 3). Without wishing to be bound by theory, the inventors believe that the antibacterial effect of the compounds according to the invention is due to an activation of SpsB and thereby stimulation of SpsB proteolysis. This activation results in the cleavage of cell-wall remodeling proteins and their corresponding dysregulation (FIG. 9). The knowledge enables the skilled person to perform a precise design and directed synthesis of chemical compounds, which exhibit antibacterial properties against bacteria having type I signal peptidase (SpsB) and is a significant improvement compared to an approach based on randomly synthesized compounds, e.g. by randomly chemical library synthesis and subsequent screen of the synthesized library compounds against bacterial strains (see for example Chang et al. (2016), J. Antimicrob. Chemother. 71: 449-459).

Signal peptidase IB enzyme (SpsB) is a serine-endopeptidase, which resides in the cytoplasmic membrane and is involved in bacterial protein secretion. Type I bacterial signal peptidases remove N-terminal signal peptides from pre-proteins, thereby maturing and releasing translocated proteins from the cytoplasmic membrane (Craney, A.; Romesberg, F. E. *Bioorg. Med. Chem. Lett.* 2015, 25 (21), 4761-4766.). Furthermore, SpsB has been shown to play an important role in virulence due to its secretory functions of virulence factors such as haemolysins and superantigens as well as its involvement in agr dependent quorum sensing signaling (Schallenberger, M. A.; Niessen, S.; Shao, C.; Fowler, B. J.; Romesberg, F. E. *J. Bacteriol.* 2012, 194 (10), 2677-2686 and Kavanaugh, J. S.; Thoendel, M.; Horswill, A. R. *Mol. Microbiol.* 2007, 65 (3), 780-798). SpsB has been repeatedly described as an attractive target for the development of antibacterial agents due to several reasons (Rao C V, S.; De Waelheyns, E.; Economou, A.; Anné, *J. Biochim. Biophys. Acta* 2014, 1843 (8), 1762-1783 and Craney, A.; Romesberg, F. E. *Bioorg. Med. Chem. Lett.* 2015, 25 (21), 4761-4766). Most importantly, it is essential for bacterial viability and growth as accumulation of secretory proteins upon activation or inhibition of SpsB is leading to cell death. In addition, the active site of SpsB is exposed to the outer side of the cytoplasmic membrane making it easily accessible for drug treatment. Bacterial type I signal peptidases are serine proteases with a unique serine/lysine dyad active site acting via a si face nucleophilic attack in contrast to the more common serine/histidine/aspartate triad utilizing a mechanism with a re face nucleophilic attack. This difference allows selective inhibition/interaction with regards to other essential proteases in eukaryots and therefore minimizes the risk of harming the host. Despite the fact that SpsB is an attractive antibacterial target there are only few inhibitor classes for this enzyme described: the natural product krisynomycin, a cyclic depsipeptide, and the naturally occurring polypeptides of the arylomycin family, synthetic arylomycin-derivatives, including M131—a synthetic derivative of actinocarbasin (Kulanthaivel, P.; Kreuzman, A. J.; Strege, M. A.; Belvo, M. D.; Smitka, T. A.; Clemens, M.; Swatting, J. R.; Minton, K. L.; Zheng, F.; Angleton, E. L.; Mullen, D.; Jungheim, L. N.; Klimkowski, V. J.; Nicas, T. I.; Thompson, R. C.; Peng, S.-B. *J. Biol. Chem.* 2004, 279 (35), 36250-36258; Schimana, J.; Gebhardt, K.; Holtzel, A.; Schmid, D. G.; Süssmuth, R.; Müller, J.; Pukall, R.; Fiedler, H.-P. *J. Antibiot.* (Tokyo). 2002, 55 (6), 565-570; Tan, Y. X.; Romesberg, F. E. *Medchemcomm* 2012, 3 (8), 916 and Therien, A. G.; Huber, J. L.; Wilson, K. E.; Beaulieu, P.; Caron, A.; Claveau, D.; Deschamps, K.; Donald, R. G. K.; Galgoci, A. M.; Gallant, M.; Gu, X.; Kevin, N. J.; Lafleur, J.; Leavitt, P. S.; Lebeau-Jacob, C.; Lee, S. S.; Lin, M. M.; Michels, A. A.; Ogawa, A. M.; Painter, R. E.; Parish, C. A.; Park, Y.-W.; Benton-Perdomo, L.; Petcu, M.; Phillips, J. W.; Powles, M. A.; Skorey, K. I.; Tam, J.; Tan, C. M.; Young, K.; Wong, S.; Waddell, S. T.; Miesel, L. *Antimicrob. Agents Chemother.* 2012, 56 (9), 4662-4670), tricyclic penems (Harris, D. A.; Powers, M. E.; Romesberg, F. E. *Bioorg. Med. Chem. Lett.* 2009, 19 (14), 3787-3790) and rationally designed peptides/lipopetides (Bruton, G.; Huxley, A.; O'Hanlon, P.; Orlek, B.; Eggleston, D.; Humphries, J.; Readshaw, S.; West, A.; Ashman, S.; Brown, M.; Moore, K.; Pope, A.; O'Dwyer, K.; Wang, L. *Eur. J. Med. Chem.* 2003, 38 (4), 351-356 and Buzder-Lantos, P.; Bockstael, K.; Anné, J.; Herdewijn, P. *Bioorg. Med. Chem. Lett.* 2009, 19 (10), 2880-2883). However, all of these compounds possess either low in vivo antibacterial activity against *S. aureus*, e.g. MIC of 8 μM for the synthetic peptide (D)-KLKI6KLK-NH$_2$, or just restore susceptibility for other antibiotics, e.g. MIC of 1.2 μM for M131 in combination with imipenem (MIC 13.4 μM) (Rao C V, S.; De Waelheyns, E.; Economou, A.; Anné, *J. Biochim. Biophys. Acta* 2014, 1843 (8), 1762-1783 and Therien, A. G.; Huber, J. L.; Wilson, K. E.; Beaulieu, P.; Caron, A.; Claveau, D.; Deschamps, K.; Donald, R. G. K.;

Galgoci, A. M.; Gallant, M.; Gu, X.; Kevin, N. J.; Lafleur, J.; Leavitt, P. S.; Lebeau-Jacob, C.; Lee, S. S.; Lin, M. M.; Michels, A. A.; Ogawa, A. M.; Painter, R. E.; Parish, C. A.; Park, Y.-W.; Benton-Perdomo, L.; Petcu, M.; Phillips, J. W.; Powles, M. A.; Skorey, K. I.; Tam, J.; Tan, C. M.; Young, K.; Wong, S.; Waddell, S. T.; Miesel, L. *Antimicrob. Agents Chemother.* 2012, 56 (9), 4662-4670).

In contrast to the prior art inhibitors of SpsB as described above, the compounds of the present invention lead to an activation SpsB and exhibit excellent antibacterial activities against various bacterial strains, in particular against clinical isolates of MRSA.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments described throughout the specification should not be construed to limit the present invention to only the explicitly described embodiments. This description should be understood to support and encompass embodiments which combine the explicitly described embodiments with any number of the disclosed and/or preferred elements. Furthermore, any permutations and combinations of all elements described herein should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In order that the present invention may be more readily understood, certain terms are first defined. Additional definitions are set forth throughout the description.

As used herein and throughout the entire description, the term "alkyl" refers to a monoradical of a saturated straight or branched hydrocarbon. Preferably, the alkyl group comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. In some embodiments, the alkyl group employed in the invention contains 1-20 carbon atoms ($C_{1-20}$ alkyl). In another embodiment, the alkyl group employed contains 1-15 carbon atoms ($C_{1-18}$ alkyl). In another embodiment, the alkyl group employed contains 1-10 carbon atoms ($C_{1-20}$ alkyl). In another embodiment, the alkyl group employed contains 1-8 carbon atoms ($C_{1-8}$ alkyl). In another embodiment, the alkyl group employed contains 1-6 carbon atoms ($C_{1-6}$ alkyl). In another embodiment, the alkyl group employed contains 1-5 carbon atoms ($C_{1-5}$-alkyl). In another embodiment, the alkyl group employed contains 1-4 carbon atoms ($C_{1-4}$ alkyl). In another embodiment, the alkyl group employed contains 1-3 carbon atoms ($C_{1-3}$ alkyl). In another embodiment, the alkyl group employed contains 1-2 carbon atoms ($C_{1-2}$ alkyl). In another embodiment, the alkyl group employed is methyl. Examples of alkyl radicals include, but are not limited to, methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethyl-hexyl, n-nonyl, n-decyl, n-undecyl, n-dodecyl, and the like, which may bear one or more substituents. Alkyl group substituents include, but are not limited to, any of the substituents described herein, that result in the formation of a stable moiety. In some embodiments the alkyl chain is a linear. In some embodiments the alkyl chain is branched. In some embodiments the alkyl chain is substituted. In some embodiments the alkyl chain is unsubstituted. In some embodiments the alkyl chain is linear and substituted or unsubstituted. In some embodiments the alkyl chain is branched and substituted or unsubstituted.

As used herein and throughout the entire description, the term term "alkylene" refers to a diradical of a saturated straight or branched hydrocarbon. Preferably, the alkylene comprises from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylenisomers (e.g., 1,1-hexylene, 1,2-hexylene, 1,3-hexylene, 1,4-hexylene, 1,5-hexylene, 1,6-hexylene, and 1,1-isohexylene), and the like. Alkylene groups may be cyclic or acyclic, branched or unbranched, substituted or unsubstituted. Alkylene group substituents include, but are not limited to, any of the substituents described herein, that result in the formation of a stable moiety.

As used herein and throughout the entire description, the term "heteroalkyl," refers to an alkyl moiety, as defined herein, which contain one or more heteroatoms (e.g., oxygen, sulfur, nitrogen, phosphorus, or silicon atoms) in between carbon atoms. The heteroalkyl may be substituted or unsubstituted. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. In certain embodiments the heteroalkyl group is a substituted heteroalkyl group containing 1-6 carbon atoms and 1-3 heteroatoms ($C_{1-6}$ heteroalkyl). In certain embodiments the heteroalkyl group is an unsubstituted heteroalkyl group containing 1-6 carbon atoms and 1-3 heteroatoms ($C_{1-6}$ heteroalkyl). In some embodiments the heteroalkyl is an alkyl moiety wherein on methylene group is replaced by S. In some embodiments the heteroalkyl is an alkyl moiety wherein on methylene group is replaced by O. In some embodiments the heteroalkyl is an alkyl moiety wherein on methylene group is replaced by NR$^{100}$, wherein R$^{100}$ is selected from the group consisting of hydrogen, substituted or unsubstituted ($C_1$-$C_6$)alkyl, substituted or unsubstituted ($C_2$-$C_6$)alkenyl, substituted or unsubstituted ($C_2$-$C_6$)alkynyl, substituted or unsubstituted ($C_3$-$C_8$)cycloalkyl, substituted or unsubstituted ($C_6$-$C_{14}$)aryl and substituted or unsubstituted ($C_3$-$C_{14}$)heteroaryl. In some embodiments heteroalkyl is —CH$_2$SCH$_3$. In some embodiments heteroalkyl is —CH$_2$OCH$_3$. In some embodiments heteroalkyl is —CH$_2$N(H)CH$_3$.

As used herein and throughout the entire description, the term "heteroalkylene" refers to a heteroalkyl biradical derived from a heteroalkyl group, as defined herein, by removal of two hydrogen atoms. The heteroalkyl group substituents include, but are not limited to, any of the substituents described herein, that result in the formation of a stable moiety.

As used herein and throughout the entire description, the term "haloalkyl" refers to an alkyl group substituted by one halogen substituent up to per halo-substitution. The halogen substituent is preferably fluorine. The haloalkyl is preferably a perfluoroalkyl. In some embodiments, the haloalkyl group employed in the invention contains 1-6 carbon atoms ($C_{1-6}$ haloalkyl). In another embodiment, the haloalkyl group employed contains 1-5 carbon atoms ($C_{1-6}$ haloalkyl). In another embodiment, the haloalkyl group employed contains 1-4 carbon atoms ($C_{1-4}$ haloalkyl). In another embodiment, the haloalkyl group employed contains 1-3 carbon atoms ($C_{1-3}$ haloalkyl). In another embodiment, the haloalkyl group employed contains 1-2 carbon atoms ($C_{1-2}$ haloalkyl). In another embodiment, the haloalkyl group employed contains 1-carbon atom ($C_1$ haloalkyl). In another embodiment, the haloalkyl group employed is trifluoromethyl. Exemplary fluoro-substituted $C_1$-$C_2$ alkyl includes—CFH$_2$, —CF$_2$H, —CF$_3$, CH$_2$CH$_2$F, —CH$_2$CHF$_2$, —CHFCH$_3$, —CHFCH$_3$, —CF$_2$CHF$_2$. Perfluoro-substituted $C_1$-$C_2$ haloalkyl, for example include —CF$_3$, and —CF$_2$CF$_3$.

As used herein and throughout the entire description, the term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. In certain embodiments, the alkenyl group employed in the invention contains 2-20 carbon atoms ($C_{2-20}$ alkenyl). In some embodiments, the alkenyl group employed in the invention contains 2-15 carbon atoms ($C_{2-15}$ alkenyl). In another embodiment, the alkenyl group employed contains 2-10 carbon atoms ($C_{2-10}$ alkenyl). In still other embodiments, the alkenyl group contains 2-8 carbon atoms ($C_{2-8}$ alkenyl). In yet other embodiments, the alkenyl group contains 2-6 carbons ($C_{2-6}$ alkenyl). In yet other embodiments, the alkenyl group contains 2-5 carbons ($C_{2-5}$ alkenyl). In yet other embodiments, the alkenyl group contains 2-4 carbons ($C_{2-4}$ alkenyl). In yet other embodiments, the alkenyl group contains 2-3 carbons ($C_{2-3}$ alkenyl). In yet other embodiments, the alkenyl group contains 2 carbons ($C_2$ alkenyl). The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. In some embodiments the alkenyl chain is a linear. In some embodiments the alkenyl chain is branched. In some embodiments the alkenyl chain is substituted. In some embodiment the alkenyl chain is unsubstituted. In some embodiments the alkenyl chain is linear and substituted or unsubstituted. In some embodiments the alkenyl chain is branched and substituted or unsubstituted. Alkenyl group substituents include, but are not limited to, any of the substituents described herein, that result in the formation of a stable moiety.

As used herein and throughout the entire description, the term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 4, i.e., 1, 2, 3, or 4, carbon-carbon double bonds. Preferably, the alkenylene group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenylene group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenylene groups include ethen-1,2-diyl, vinyliden, 1-propen-1,2-diyl, 1-propen-1,3-diyl, 1-propen-2,3-diyl, allyliden, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like. If an alkenylene group is attached to a nitrogen atom, the double bond cannot be alpha to the nitrogen atom. Alkenylene groups may be cyclic or acyclic, branched or unbranched, substituted or unsubstituted. Alkenylene group substituents include, but are not limited to, any of the substituents described herein, that result in the formation of a stable moiety.

As used herein and throughout the entire description, the term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. In certain embodiments, the alkynyl group employed in the invention contains 2-20 carbon atoms ($C_{2-20}$ alkynyl). In some embodiments, the alkynyl group employed in the invention contains 2-15 carbon atoms ($C_{2-15}$ alkynyl). In another embodiment, the alkynyl group employed contains 2-10 carbon atoms ($C_{2-10}$ alkynyl). In still other embodiments, the alkynyl group contains 2-8 carbon atoms ($C_{2-8}$ alkynyl). In still other embodiments, the alkynyl group contains 2-6 carbon atoms ($C_{2-6}$ alkynyl). In still other embodiments, the alkynyl group contains 2-5 carbon atoms ($C_{2-5}$ alkynyl). In still other embodiments, the alkynyl group contains 2-4 carbon atoms ($C_{2-4}$ alkynyl). In still other embodiments, the alkynyl group contains 2-3 carbon atoms ($C_{2-3}$ alkynyl). In still other embodiments, the alkynyl group contains 2 carbon atoms ($C_2$ alkynyl). Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like, which may bear one or more substituents. Alkynyl group substituents include, but are not limited to, any of the substituents described herein, that result in the formation of a stable moiety. If an alkynyl group is attached to a nitrogen atom, the triple bond cannot be alpha to the nitrogen atom. In some embodiments the alkynyl chain is a linear. In some embodiments the alkynyl chain is branched. In some embodiments the alkynyl chain is substituted. In some embodiment the alkynyl chain is unsubstituted. In some embodiments the alkynyl chain is linear and substituted or unsubstituted. In some embodiments the alkynyl chain is branched and substituted or unsubstituted.

As used herein and throughout the entire description, the term "alkynylene" refers to a diradical of an unsaturated straight or branched hydrocarbon having at least one carbon-carbon triple bond. Generally, the maximal number of carbon-carbon triple bonds in the alkynylene group can be equal to the integer which is calculated by dividing the number of carbon atoms in the alkynylene group by 2 and, if the number of carbon atoms in the alkynylene group is uneven, rounding the result of the division down to the next integer. For example, for an alkynylene group having 9 carbon atoms, the maximum number of carbon-carbon triple bonds is 4. Preferably, the alkynylene group has 1 to 4, i.e., 1, 2, 3, or 4, more preferably 1 or 2 carbon-carbon triple bonds. Preferably, the alkynylene group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynylene group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynylene groups include ethyn-1,2-diyl, 1-propyn-1,3-diyl, 1-propyn-3,3-diyl, 1-butyn-1,3-diyl, 1-butyn-1,4-diyl, 1-butyn-3,4-diyl, 2-butyn-1,4-diyl and the like. If an alkynylene group is attached to a nitrogen atom, the triple bond cannot be alpha to the nitrogen atom. Alkynylene groups may be cyclic or acyclic, branched or unbranched, substituted or unsubstituted. Alkynylene group substituents include, but are not limited to, any of the substituents described herein, that result in the formation of a stable moiety.

As used herein and throughout the entire description, the term "cycloalkyl" or "cycloaliphatic" or "carbocyclic" or "carbocycle" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 8 carbon atoms, even more preferably 3 to 7 carbon atoms. In certain embodiments, the cycloalkyl group employed in the invention contains 3-14 carbon atoms ($C_{3-14}$ cycloalkyl). In certain embodiments, the cycloalkyl group employed in the invention contains 3-12 carbon atoms ($C_{3-12}$ cycloalkyl). In another embodiment, the cycloalkyl group employed in the invention contains 3-10 carbon atoms ($C_{3-10}$ cycloalkyl). In another embodiment, the cycloalkyl group employed in the invention contains 3-8 carbon atoms ($C_{3-8}$ cycloalkyl). In another embodiment, the cycloalkyl group employed in the invention contains 3-7 carbon atoms ($C_{3-7}$ cycloalkyl). In another embodiment, the cycloalkyl group employed in the invention contains 3-6 carbon atoms ($C_{3-6}$ cycloalkyl). In another embodiment, the cycloalkyl group employed in the invention contains 3-5 carbon atoms ($C_{3-5}$ cycloalkyl). In another embodiment, the cycloalkyl group employed in the invention contains 3-4 carbon atoms ($C_{3-4}$ cycloalkyl). In another embodiment, the cycloalkyl group employed in the invention contains 3 carbon atoms ($C_3$ cycloalkyl). Exemplary cycloalkyl groups include cyclopropyl, cyclopropenyl, cyclobutyl, cyclobutenyl, cyclopentyl, cycloheptenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl. Cycloalkyl group substituents include, but are not limited to, any of the substituents described herein, that result in the formation of a stable moiety.

As used herein and throughout the entire description, the term "cyclopropylene" means a cyclopropyl group as defined above in which one hydrogen atom has been removed resulting in a diradical. The cyclopropylene may link two atoms or moieties via the same carbon atom (1,1-cyclopropylene, i.e., a geminal diradical) or via two carbon atoms (1,2-cyclopropylene).

As used herein and throughout the entire description, the term "aryl" or "aromatic ring" refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but are not limited to, phenyl, biphenyl, naphthyl, and the like, which may bear one or more substituents. Preferably, the aryl group contains 3 to 14 (e.g., 5 to 10, such as 5, 6, or 10) carbon atoms, more preferably 6 to 10 carbon atoms, which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. In certain embodiments, the aryl group employed in the invention contains 3-20 carbon atoms ($C_{3-20}$ aryl). In certain embodiments, the aryl group employed in the invention contains 3-18 carbon atoms ($C_{3-18}$ aryl). In another embodiment, the aryl group employed in the invention contains 3-16 carbon atoms ($C_{3-16}$ aryl). In another embodiment, the aryl group employed in the invention contains 6-16 carbon atoms ($C_{6-16}$ aryl). In another embodiment, the aryl group employed in the invention contains 7-16 carbon atoms ($C_{7-16}$ aryl). In another embodiment, the aryl group employed in the invention contains 6-14 carbon atoms ($C_{6-14}$ aryl). In another embodiment, the aryl group employed in the invention contains 7-14 carbon atoms ($C_{7-14}$ aryl). In another embodiment, the aryl group employed in the invention contains 6-12 carbon atoms ($C_{6-12}$ aryl).). In another embodiment, the aryl group employed in the invention contains 7-12 carbon atoms ($C_{7-12}$ aryl). In another embodiment, the aryl group employed in the invention contains 6-11 carbon atoms ($C_{6-11}$ aryl). In another embodiment, the aryl group employed in the invention contains 7-11 carbon atoms ($C_{7-11}$ aryl). In another embodiment, the aryl group employed in the invention contains 6-10 carbon atoms ($C_{6-10}$ aryl). In another embodiment, the aryl group employed in the invention contains 7-10 carbon atoms ($C_{7-10}$ aryl). In another embodiment, the aryl group employed in the invention contains 6-8 carbon atoms ($C_{6-8}$ aryl). In another embodiment, the aryl group employed in the invention contains 6 carbon atoms ($C_6$ aryl). In another embodiment, the aryl group employed in the invention contains 10 carbon atoms ($C_{10}$ aryl).

As used herein and throughout the entire description, the term "arylene" refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

As used herein and throughout the entire description, the term "heteroaryl" or "heteroaromatic ring" means an aryl group as defined above in which one or more carbon atoms in the aryl group are replaced by heteroatoms of O, S, or N. Preferably, the heteroaryl group contains 3 to 14 carbon atoms. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. In certain embodiments, the heteroaryl group employed in the invention is a five membered aromatic monocyclic ring wherein 1, 2, or 3 carbon atoms are replaced by the same or different heteroatoms of O, N, or S. In certain embodiments, the heteroaryl group employed in the invention is a five membered aromatic monocyclic ring wherein 1, 2, or 3 carbon atoms are replaced by the same or different heteroatoms of O. In certain embodiments, the heteroaryl group employed in the invention is a five membered aromatic monocyclic ring wherein 1, 2, or 3 carbon atoms are replaced by the same or different heteroatoms of O and N. In certain embodiments, the heteroaryl group employed in the invention is a five membered aromatic monocyclic ring wherein 1, 2, or 3 carbon atoms are replaced by the same or different heteroatoms of O and S. In certain embodiments, the heteroaryl group employed in the invention is a five membered aromatic monocyclic ring wherein 1, 2, or 3 carbon atoms are replaced by the same or different heteroatoms of N and S. In certain embodiments, the heteroaryl group employed in the invention is a six membered aromatic monocyclic ring wherein 1, 2, or 3 carbon atoms are replaced by the same or different heteroatoms of O, S or N. In certain embodiments, the heteroaryl group employed in the invention is a six membered aromatic monocyclic ring wherein 1, 2, or 3 carbon atoms are replaced by N. In certain embodiments, the heteroaryl group employed in the invention is an aromatic bicyclic system wherein 1, 2, 3, 4, or 5 carbon atoms are replaced with the same or different heteroatoms of O, N, or S. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, azaindolyl (4-, 5-6- and 7-), diazaindolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, pyrrolopyrrolyl, and the like, which may bear one or more substituents. Heteroaryl substituents include, but are not limited to, any of the substituents described herein, that result in the formation of a stable moiety. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl. Exemplary bicyclic heteroaryl groups 7-azaindolyl, 6-azaindolyl, 5-azaindolyl, 4-azaindolyl, and indolyl.

As used herein and throughout the entire description, the term "heteroarylene" refers to a biradical derived from a heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

As used herein and throughout the entire description, the terms "arylalkyl" and "heteroarylalkyl" are meant to include those radicals in which an aryl group and heteroaryl group, respectively, is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Preferably the Arylalkyl is a substituted or unsubstituted ($C_6$-$C_{14}$)aryl($C_1$-$C_6$)alkyl Preferably the Arylalkyl is a substituted or unsubstituted ($C_6$-$C_{10}$)aryl($C_1$-$C_6$)alkyl. Preferably the Heteroarylalkyl is a substituted or unsubstituted ($C_3$-$C_{14}$)heteroaryl($C_1$-$C_6$)alkyl. Preferably the Heteroarylalkyl is a substituted or unsubstituted ($C_3$-$C_{10}$)heteroaryl($C_1$-$C_6$)alkyl. In some embodiments the alkyl chain is a linear. In some embodiments the alkyl chain is branched. In some embodiments the alkyl chain is substituted. In some embodiments the alkyl chain is unsubstituted. In some embodiments the alkyl chain is linear and substituted or unsubstituted. In some embodiments the alkyl chain is branched and substituted or unsubstituted.

As used herein and throughout the entire description, the term "heterocyclyl" or "heterocyclic ring" or "heterocycle refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. The heterocyclic group may be substituted or unsubstituted. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Preferably, in each ring of the heterocyclyl group the maximum number of 0 atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydrobenzofuranyl (1- and 2-), di- and tetrahydroindolyl, di- and tetrahydroisoindolyl, di- and tetrahydrobenzothienyl (1- and 2), di- and tetrahydro-1H-indazolyl, di- and tetrahydrobenzimidazolyl, di- and tetrahydrobenzoxazolyl, di- and tetrahydroindoxazinyl, di- and tetrahydrobenzisoxazolyl, di- and tetrahydrobenzothiazolyl, di- and tetrahydrobenzisothiazolyl, di- and tetrahydrobenzotriazolyl, di- and tetrahydroquinolinyl, di- and tetrahydroisoquinolinyl, di- and tetrahydrobenzodiazinyl, di- and tetrahydroquinoxalinyl, di- and tetrahydroquinazolinyl, di- and tetrahydrobenzotriazinyl (1,2,3- and 1,2,4-), di- and tetrahydropyridazinyl, di- and tetrahydrophenoxazinyl, di- and tetrahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro[1,3]thiazolo[5,4-c]pyridin-2-yl or 4,5,6-7-tetrahydro[1,3]thiazolo[4,5-c]pyridin-2-yl), di- and tetrahydropyrrolothiazolyl (such as 5,6-dihydro-4H-pyrrolo[3,4-d][1,3]thiazolyl), di- and tetrahydrophenothiazinyl, di- and tetrahydroisobenzofuranyl, di- and tetrahydrochromenyl, di- and tetrahydroxanthenyl, di- and tetrahydrophenoxathiinyl, di- and tetrahydropyrrolizinyl, di- and tetrahydroindolizinyl, di- and tetrahydroindazolyl, di- and tetrahydropurinyl, di- and tetrahydroquinolizinyl, di- and tetrahydrophthalazinyl, di- and tetrahydronaphthyridinyl (1,5-, 1,6-, 1,7-, 1,8-, and 2,6-), di- and tetrahydrocinnolinyl, di- and tetrahydropteridinyl, di- and tetrahydrocarbazolyl, di- and tetrahydrophenanthridinyl, di- and tetrahydroacridinyl, di- and tetrahydroperimidinyl, di- and tetrahydrophenanthrolinyl (1,7-, 1,8-, 1,10-, 3,8-, and 4,7-), di- and tetrahydrophenazinyl, di- and tetrahydrooxazolopyridinyl, di- and tetrahydroisoxazolopyridinyl, di- and tetrahydropyrrolooxazolyl, and di- and tetrahydropyrrolopyrrolyl. Exemplary 5- or 6-membered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydropyridazinyl and the like, which may bear one or more substituents. Preferably 2H-1-benzopyranyl (2H-chromenyl), benzodihydropyranyl (chromanyl), 4H-1-benzopyranyl (4H-chromenyl), 1H-2-benzopyranyl (1H-isochromenyl), isochromanyl, 3H-2-benzopyranyl (3H-isochromenyl), 1-benzopyran-4-on-yl (chromonyl), 4-chromanonyl, 1-benzopyran-2-on-yl (coumarinyl), dihydrocoumarinyl, 3-isochromanonyl, 2-coumaranon-yl. In some embodiments, the heterocyclyl group is substituted or unsubstituted 2H-1-benzopyranyl (2H-chromenyl). In some embodiments, the heterocyclyl group is substituted or unsubstituted benzodihydropyranyl (chromanyl). In some embodiments, the heterocyclyl group is substituted or unsubstituted 4H-1-benzopyranyl (4H-chromenyl). In some embodiments, the heterocyclyl group is substituted or unsubstituted 1H-2-benzopyranyl (1H-isochromenyl). In some embodiments, the heterocyclyl group is substituted or unsubstituted isochromanyl. In some embodiments, the heterocyclyl group is substituted or unsubstituted 3H-2-benzopyranyl (3H-isochromenyl). In some embodiments, the heterocyclyl group is substituted or unsubstituted 1-benzopyran-4-on-yl (chromonyl). In some embodiments, the heterocyclyl group is substituted or unsubstituted 4-chromanonyl. In some embodiments, the heterocyclyl group is substituted or unsubstituted 1-benzopyran-2-on-yl (coumarinyl). In some embodiments, the heterocyclyl group is substituted or unsubstituted dihydrocoumarinyl. In some embodiments, the heterocyclyl group is substituted or unsubstituted 3-isochromanonyl. In some embodiments, the heterocyclyl group is substituted or unsubstituted 2-coumaranon-yl. In some embodiments, the heterocyclyl group is a substituted or unsubstituted $(C_3-C_{14})$ heterocyclyl group, wherein 1, 2, 3, 4, or 5 carbon atoms are replaced with the same or different heteroatoms of O, N, or S. In some embodiments, the heterocyclyl group is a substituted or unsubstituted $(C_3-C_{14})$heterocyclyl group, wherein 1, 2, 3, 4, or 5 carbon atoms are replaced with O. In some embodiments, the heterocyclyl group is a substituted or unsubstituted $(C_3-C_{14})$heterocyclyl group, wherein 1, 2, 3, 4, or 5 carbon atoms are replaced with N. In some embodiments, the heterocyclyl group is a substituted or unsubstituted $(C_3-C_{14})$heterocyclyl group, wherein 1, 2, 3, 4, or 5 carbon atoms are replaced with S. In some embodiments, the heterocyclyl group is a substituted or unsubstituted $(C_9-C_{10})$heterocyclyl group, wherein 1, 2, 3, 4, or 5 carbon atoms are replaced with the same or different heteroatoms of O, N, or S. In some embodiments, the heterocyclyl group is a substituted or unsubstituted $(C_9-C_{10})$ heterocyclyl group, wherein 1, 2, 3, 4, or 5 carbon atoms are replaced with O. In some embodiments, the heterocyclyl group is a substituted or unsubstituted $(C_9-C_{10})$heterocyclyl group, wherein 1, 2, 3, 4, or 5 carbon atoms are replaced with N. In some embodiments, the heterocyclyl group is a substituted or unsubstituted $(C_8-C_{10})$heterocyclyl group, wherein 1, 2, 3, 4, or 5 carbon atoms are replaced with S. In some embodiments, the heterocyclyl group is a substituted or unsubstituted $(C_{10})$heterocyclyl group, wherein 1, 2, 3, 4, or 5 carbon atoms are replaced with the same or different heteroatoms of O, N, or S. In some embodiments, the heterocyclyl group is a substituted or unsubstituted $(C_{10})$ heterocyclyl group, wherein 1, 2, 3, 4, or 5 carbon atoms are replaced with O. In some embodiments, the heterocyclyl group is a substituted or unsubstituted $(C_{10})$heterocyclyl group, wherein 1, 2, 3, 4, or 5 carbon atoms are replaced with N. In some embodiments, the heterocyclyl group is a substituted or unsubstituted $(C_{10})$heterocyclyl group, wherein 1, 2, 3, 4, or 5 carbon atoms are replaced with S.

As used herein and throughout the entire description, the term "optionally substituted" or "substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group different from hydrogen such as $(C_1-C_6)$alkyl, $(C_1-C_6)$heteroalkyl, $(C_1-C_6)$haloalkyl; $(C_2-C_6)$alkenyl, $(C_2-C_6)$alkynyl, $(C_3-C_8)$ cycloalkyl, $(C_6-C_{10})$aryl, $(C_6-C_{10})$aryl$(C_1-C_6)$alkyl, $(C_3-C_{10})$heteroaryl, $(C_3-C_{18})$heteroaryl$(C_1-C_6)$alkyl, halogen, —CN, —NO$_2$, —OR$^{61}$, —N(R$^{62}$)(R$^{63}$), —N(R$^{61}$)(OR$^{61}$), —S(O)$_{0-2}$R$^{61}$, —S(O)$_{1-2}$OR$^{61}$, —OS(O)$_{1-2}$R$^{61}$, —OS(O)$_{1-2}$OR$^{61}$, —S(O)$_{1-2}$N(R$^{62}$)(R$^{6}$), —OS(O)$_{1-2}$N(R$^{62}$)(R$^{63}$), —N(R$^{61}$)S(O)$_{1-2}$R$^{61}$, —NR$^{61}$S(O)$_{1-2}$OR$^{61}$, —NR$^{61}$S(O)$_{1-2}$N(R$^{62}$)(R$^{63}$), —C(=W) R$^{61}$, —C(=W)WR$^{61}$, —WC(=W)R$^{61}$, and —WC(=W)WR$^{61}$; wherein R$^{61}$, R$^{62}$, and R$^{63}$ are independently selected from the group consisting of —H, alkyl, alkenyl, alkynyl, cycloalkyl, aryl, heteroaryl, and heterocyclyl, preferably wherein R$^{61}$, R$^{62}$, and R$^{63}$ are independently selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl; R$^{64}$ is independently selected from the group consisting of —H, alkyl, alkenyl, alkynyl, cycloalkyl, aryl, heteroaryl, heterocyclyl, and —OR$^{61}$; W is independently selected from O, S, and N(R$^{64}$).

As used herein and throughout the entire description, the term "halogen" or "halo" means fluoro, chloro, bromo, or iodo.

As used herein and throughout the entire description, the term "cyano" mean —CN.

As used herein and throughout the entire description, the terms "bacterial disease" or "bacterial infection" are used interchangeably and refer to any pathological state, including any asymptomatic, acute or chronic bacterial infection and any state caused by or associated with such bacterial infection. In some embodiments the bacterial infection is an infection caused by bacteria which belong to the groups of Firmicutes and Actinobacteria. In some embodiments the infection is caused by bacteria consisting of the group *Staphylococcus aureus*, MRSA, clinical isolates thereof, *Clostridium difficile, Streptococcus pneumonia, Streptococcus pyogenes, Streptococcus pneumonia, Staphylococcus epidermidis, Staphylococcus haemolyticus, Staphylococcus hominis*, Vancomycin-intermediate *S. aureus*, Vancomycin-resistant *S. aureus, Listeria monocytogenes, Mycobacterium tuberculosis, Burkholderia thailandensis*. In some embodiments the bacterial infection is an infection caused by gram-positive bacteria, preferably by *Staphylococcus aureus*, methicillin-resistant *Staphylococcus aureus* (MRSA) and clinical isolates thereof, and Vancomycin-intermediate *S. aureus*, Vancomycin-resistant *S. aureus*. In some embodiments the bacterial infection is an infection caused by bacterial of the *Mycobacterium tuberculosis* Complex, including *M. tuberculosis, M. africanum, M. bovis, M. caprae* etc. Further specific embodiments defining the bacterial disease are described herein below.

In a first aspect the present invention relates to a compound for use in the treatment of a bacterial disease, said compound having a structure according to Formula I

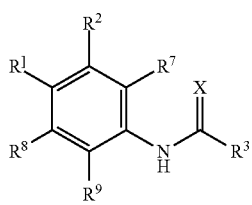

(I)

wherein
R$^1$, R$^2$, R$^7$, R$^8$, R$^9$ are each independently selected from the group consisting of hydrogen, halogen, cyano, (C$_1$-C$_6$)alkyl and (C$_1$-C$_6$)haloalkyl, preferably wherein R$^7$, R$^8$, R$^9$ are hydrogen and R$^1$ is selected from the group consisting of hydrogen, cyano and halogen, preferably hydrogen and halogen, and R$^2$ is (C$_1$-C$_6$) alkyl or (C$_1$-C$_6$)haloalkyl;

R$^3$ is NHR$^4$ or NR$^5$R$^6$;

R$^4$ is selected from the group consisting of

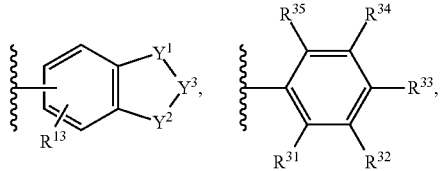

and substituted or unsubstituted naphthyl;

R$^5$ and R$^6$ are each independently selected from the group consisting of substituted or unsubstituted (C$_1$-C$_6$)alkyl, substituted or unsubstituted (C$_1$-C$_6$)heteroalkyl, substituted or unsubstituted (C$_2$-C$_6$)alkenyl and substituted or unsubstituted (C$_6$-C$_{10}$)aryl(C$_1$-C$_6$)alkyl;

wherein R$^5$ and R$^6$ join together with the nitrogen atom to which they are attached to form a ring, which is optionally substituted with one or more independently selected R$^{51}$, preferably wherein the formed ring is a five, six or seven-membered ring, which is optionally substituted with one or more independently selected R$^{51}$;

Y$^1$ and Y$^2$ are each independently selected from the group consisting of O, S, SO, SO$_2$ and CH$_2$;

Y$^3$ is CR$^{11}$R$^{12}$;

R$^{11}$ and R$^{12}$ are each independently selected from the group consisting of hydrogen and halogen;

R$^{13}$ is selected from the group consisting of hydrogen, (C$_1$-C$_6$)alkyl, (C$_1$-C$_6$)haloalkyl and halogen, preferably hydrogen;

R$^{14}$ is selected from —O—(C$_1$-C$_6$)alkyl, —O—(C$_1$-C$_6$)haloalkyl, —NH—CH$_3$ and substituted or unsubstituted (C$_6$-C$_{14}$)aryl;

R$^{15}$ is selected from the group consisting of (C$_1$-C$_6$)alkyl, (C$_1$-C$_6$)haloalkyl and substituted or unsubstituted (C$_6$-C$_{14}$)aryl, preferably (C$_1$-C$_6$)alkyl and (C$_1$-C$_6$)haloalkyl;

R$^{31}$, R$^{32}$, R$^{33}$, R$^{34}$ and R$^{35}$ are each independently selected from the group consisting of hydrogen, substituted or unsubstituted (C$_1$-C$_6$)alkyl, (C$_1$-C$_6$)haloalkyl, —C(O)R$^{14}$, substituted or unsubstituted (C$_6$-C$_{14}$)aryl(C$_1$-C$_6$)alkyl, —OR$^{15}$ and —NH—C(O)—NH—B;

R$^{51}$ is selected from the group consisting of hydrogen, substituted or unsubstituted (C$_1$-C$_6$)alkyl, (C$_1$-C$_6$)heteroalkyl, (C$_1$-C$_6$)haloalkyl; substituted or unsubstituted (C$_2$-C$_6$)alkenyl, substituted or unsubstituted (C$_2$-C$_6$) alkynyl, substituted or unsubstituted (C$_3$-C$_6$)cycloalkyl, substituted or unsubstituted (C$_6$-C$_{10}$)aryl, substituted or unsubstituted (C$_6$-C$_{10}$)aryl(C$_1$-C$_6$)alkyl, substituted or unsubstituted (C$_3$-C$_{10}$)heteroaryl, substituted or unsubstituted (C$_3$-C$_{10}$)heteroaryl(C$_1$-C$_6$)alkyl, halogen, —CN, —NO$_2$, —OR$^{61}$, —N(R$^{62}$)(R$^{63}$), —N(R$^{61}$)(OR$^{61}$), —S(O)$_{0-2}$R$^{61}$, —S(O)$_{1-2}$OR$^{61}$, —OS(O)$_{1-2}$R$^{61}$, —OS(O)$_{1-2}$OR$^{61}$, —S(O)$_{1-2}$N(R$^{62}$)(R$^{63}$), —OS(O)$_{1-2}$N(R$^{62}$)(R$^{63}$), —N(R$^{61}$)S(O)$_{1-2}$R$^{61}$, —NR$^{61}$S(O)$_{1-2}$OR$^{61}$, —NR$^{61}$S(O)$_{1-2}$N(R$^{62}$)(R$^{63}$), —C(=W)R$^{61}$, —C(=W)WR$^{61}$, —WC(=W)R$^{61}$, and —WC(=W)WR$^{61}$;

R$^{61}$ is, in each case, selected from the group consisting of —H, alkyl, alkenyl, alkynyl, cycloalkyl, aryl, heteroaryl, and heterocyclyl;

$R^{62}$ and $R^{63}$ are, in each case, independently selected from the group consisting of —H, alkyl, alkenyl, alkynyl, cycloalkyl, aryl, heteroaryl, and heterocyclyl;

$R^{64}$ is independently selected from the group consisting of —H, alkyl, alkenyl, alkynyl, cycloalkyl, aryl, heteroaryl, heterocyclyl, and —$OR^{61}$;

W is independently selected from O, S, and $N(R^{64})$;

B is phenyl, optionally substituted with 1-3 substituents independently selected from the group consisting of hydrogen, $(C_1-C_6)$alkyl, $(C_1-C_6)$haloalkyl, halogen, cyano, nitro, —O—$(C_1-C_6)$alkyl and —O—$(C_1-C_6)$haloalkyl, preferably hydrogen, $(C_1-C_6)$alkyl, $(C_1-C_6)$haloalkyl and halogen;

X is selected from O or S;

or a pharmaceutically acceptable salt, solvate or hydrate thereof.

As used herein and throughout the entire description, the term "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

As used herein and throughout the entire description, the term "pharmaceutically acceptable" may in particular mean approved by a regulatory agency or other generally recognized pharmacopoeia for use in animals, and more particularly in humans.

As used herein and throughout the entire description, the term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In another aspect the present invention relates to a pharmaceutical composition for use in the treatment of a bacterial disease, wherein said composition comprises a compound having a structure according to Formula I

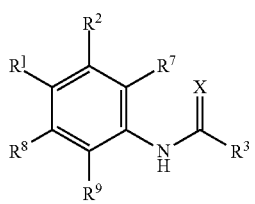

(I)

wherein $R^1$, $R^2$, $R^7$, $R^8$, $R^9$ are each independently selected from the group consisting of hydrogen, halogen, cyano, $(C_1-C_6)$alkyl and $(C_1-C_6)$haloalkyl, preferably wherein $R^7$, $R^8$, $R^9$ are hydrogen and $R^1$ is selected from the group consisting of hydrogen, cyano and halogen, preferably hydrogen and halogen, and $R^2$ is $(C_1-C_6)$alkyl or $(C_1-C_6)$haloalkyl;

$R^3$ is —$NHR^4$ or —$NR^5R^6$;

$R^4$ is selected from the group consisting of

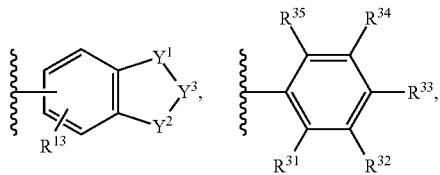

and substituted or unsubstituted naphthyl;

$R^5$ and $R^6$ are each independently selected from the group consisting of substituted or unsubstituted $(C_1-C_6)$alkyl, substituted or unsubstituted $(C_1-C_6)$heteroalkyl, substituted or unsubstituted $(C_2-C_6)$alkenyl and substituted or unsubstituted $(C_6-C_{10})$aryl$(C_1-C_6)$alkyl;

wherein $R^5$ and $R^6$ join together with the nitrogen atom to which they are attached to form a ring, which is optionally substituted with one or more independently selected $R^{51}$, preferably wherein the formed ring is five, six or seven-membered ring, which is optionally substituted with one or more independently selected $R^{51}$;

$Y^1$ and $Y^2$ are each independently selected from the group consisting of O, S, SO, $SO_2$ and $CH_2$;

$Y^3$ is $CR^{11}R^{12}$;

$R^{11}$ and $R^{12}$ are each independently selected from the group consisting of hydrogen and halogen;

$R^{13}$ is selected from the group consisting of hydrogen, $(C_1-C_6)$alkyl, $(C_1-C_6)$haloalkyl and halogen, preferably hydrogen;

$R^{14}$ is selected from —O—$(C_1-C_6)$alkyl, —O—$(C_1-C_6)$haloalkyl, —NH—$CH_3$ and substituted or unsubstituted $(C_6-C_{14})$aryl;

$R^{15}$ is selected from the group consisting of $(C_1-C_6)$alkyl, $(C_1-C_6)$haloalkyl and substituted or unsubstituted $(C_6-C_{14})$aryl, preferably $(C_1-C_6)$alkyl and $(C_1-C_6)$haloalkyl;

$R^{31}$, $R^{32}$, $R^{33}$, $R^{34}$ and $R^{35}$ are each independently selected from the group consisting of hydrogen, substituted or unsubstituted $(C_1-C_6)$alkyl, $(C_1-C_6)$haloalkyl, —$C(O)R^{14}$, substituted or unsubstituted $(C_6-C_{14})$aryl$(C_1-C_6)$alkyl, —$OR^{15}$ and —NH—C(O)—NH—B;

$R^{51}$ is selected from the group consisting of hydrogen, substituted or unsubstituted $(C_1-C_6)$alkyl, $(C_1-C_6)$heteroalkyl, $(C_1-C_6)$haloalkyl; substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{10})$aryl, substituted or unsubstituted $(C_6-C_{10})$aryl$(C_1-C_6)$alkyl, substituted or unsubstituted $(C_3-C_{10})$heteroaryl, substituted or unsubstituted $(C_3-C_{10})$heteroaryl$(C_1-C_6)$alkyl, halogen, —CN, —$NO_2$, —$OR^{61}$, —$N(R^{62})(R^{63})$, —$N(R^{61})(OR^{61})$, —$S(O)_{0-2}R^{61}$, —$S(O)_{1-2}OR^{61}$, —$OS(O)_{1-2}R^{61}$, —$OS(O)_{1-2}OR^{61}$, —$S(O)_{1-2}N(R^{62})(R^{63})$, —$OS(O)_{1-2}N(R^{62})(R^{63})$, —$N(R^{61})S(O)_{1-2}R^{61}$, —NR$^{61}$S(O)$_{1-2}$OR$^{61}$, —NR$^{61}$S(O)$_{1-2}$N(R$^{62}$)(R$^{63}$), —C(=W) R$^{61}$, —C(=W)WR$^{61}$, —WC(=W) R$^{61}$, and —WC(=W)WR$^{61}$;

R$^{61}$ is, in each case, selected from the group consisting of —H, alkyl, alkenyl, alkynyl, cycloalkyl, aryl, heteroaryl, and heterocyclyl;

R$^{62}$ and R$^{63}$ are, in each case, independently selected from the group consisting of —H, alkyl, alkenyl, alkynyl, cycloalkyl, aryl, heteroaryl, and heterocyclyl;

R$^{64}$ is independently selected from the group consisting of —H, alkyl, alkenyl, alkynyl, cycloalkyl, aryl, heteroaryl, heterocyclyl, and —OR$^{61}$;

W is independently selected from O, S, and N(R$^{64}$);

B is phenyl, optionally substituted with 1-3 substituents independently selected from the group consisting of hydrogen, (C$_1$-C$_6$)alkyl, (C$_1$-C$_6$)haloalkyl, halogen, cyano, nitro, —O—(C$_1$-C$_6$)alkyl and —O—(C$_1$-C$_6$)haloalkyl, preferably hydrogen, (C$_1$-C$_6$)alkyl, (C$_1$-C$_6$) haloalkyl and halogen;

X is selected from O or S;

or a pharmaceutically acceptable salt, solvate or hydrate thereof.

In the following embodiments the compound for use in treatment of a bacterial disease as disclosed herein above and the compound of the pharmaceutical composition for use in the treatment of a bacterial disease as disclosed herein above are further defined.

In some embodiments R$^1$ is selected from hydrogen and halogen, in other embodiments R$^1$ is halogen, in in other embodiments R$^1$ is chlorine.

In some embodiments R$^2$ is (C$_1$-C$_6$)alkyl, in other embodiments R$^2$ is (C$_1$-C$_5$)alkyl, in other embodiments R$^2$ is (C$_1$-C$_4$)alkyl, in other embodiments R$^2$ is (C$_1$-C$_3$)alkyl, in other embodiments R$^2$ is (C$_1$-C$_2$)alkyl, in other embodiments R$^2$ is methyl. In some embodiments R$^2$ is (C$_1$-C$_6$)haloalkyl, in other embodiments R$^2$ is (C$_1$-C$_5$)haloalkyl, in other embodiments R$^2$ is (C$_1$-C$_4$)haloalkyl, in other embodiments R$^2$ is (C$_1$-C$_3$)haloalkyl, in other embodiments R$^2$ is (C$_1$-C$_2$)haloalkyl, in other embodiments R$^2$ is —CF$_3$.

In some embodiments R$^1$, R$^2$, R$^7$, R$^8$, R$^9$ are each independently selected from the group consisting of hydrogen, halogen, cyano, (C$_1$-C$_6$)alkyl and (C$_1$-C$_6$)haloalkyl, wherein at least one of R$^1$, R$^2$, R$^7$, R$^8$ and R$^9$ is halogen. In some embodiments R$^1$, R$^2$, R$^7$, R$^8$, R$^9$ are each independently selected from the group consisting of hydrogen, halogen, cyano, (C$_1$-C$_6$)alkyl and (C$_1$-C$_6$)haloalkyl, wherein wherein one of R$^1$, R$^2$, R$^7$, R$^8$ and R$^9$ is (C$_1$-C$_6$)haloalkyl. In some embodiments R$^1$, R$^2$, R$^7$, R$^8$, R$^9$ are each independently selected from the group consisting of hydrogen, halogen, cyano, (C$_1$-C$_6$)alkyl and (C$_1$-C$_6$)haloalkyl, wherein one of R$^1$, R$^2$, R$^7$, R$^8$ and R$^9$ is (C$_1$-C$_6$)haloalkyl and one halogen. In some embodiments R$^1$, R$^2$, R$^7$, R$^8$, R$^9$ are each independently selected from the group consisting of hydrogen, halogen, cyano, (C$_1$-C$_6$)alkyl and (C$_1$-C$_6$)haloalkyl, wherein not more than two of R$^1$, R$^2$, R$^7$, R$^8$ and R$^9$ are different than hydrogen. In some embodiments three of R$^1$, R$^2$, R$^7$, R$^8$, R$^9$ are hydrogen and two are each independently selected from the group consisting of halogen, cyano, and (C$_1$-C$_6$)haloalkyl.

In some embodiments R$^3$ is selected from the group consisting of —NHR$^4$ and —NR$^5$R$^6$; in other embodiments R$^3$ is selected from the group consisting of —NHR$^4$— NR$^5$R$^6$,

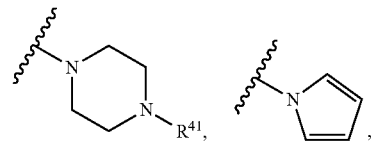

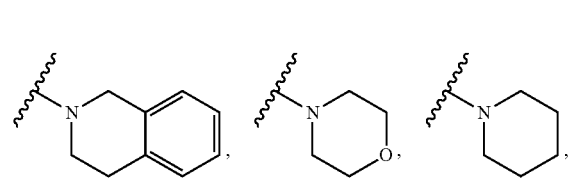

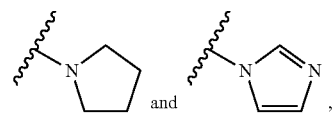

in other embodiments

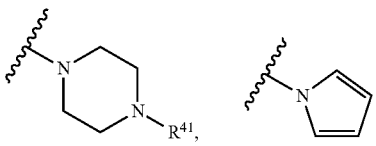

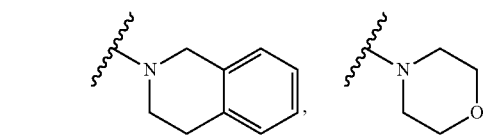

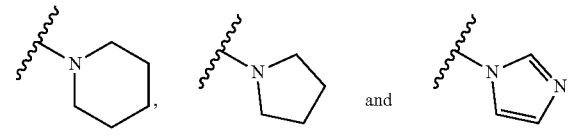

may be substituted or unsubstituted, in particular the CH$_2$ and/or CH groups of said ring structures may be each independently substituted with one or more residues selected from the group consisting of hydrogen, substituted or unsubstituted (C$_1$-C$_6$)alkyl, (C$_1$-C$_6$)heteroalkyl, (C$_1$-C$_6$)haloalkyl; substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{10}$)aryl, substituted or unsubstituted (C$_6$-C$_{10}$)aryl(C$_1$-C$_6$)alkyl, substituted or unsubstituted (C$_3$-C$_{10}$)heteroaryl, substituted or unsubstituted (C$_3$-C$_{10}$)heteroaryl(C$_1$-C$_6$)alkyl, halogen, —CN, —NO$_2$, —OR$^{61}$, —N(R$^{62}$)(R$^{63}$), —N(R$^{61}$)(OR$^{61}$), —S(O)$_{0-2}$R$^{61}$, —S(O)$_{1-2}$OR$^{61}$, —OS(O)$_{1-2}$R$^{61}$, —OS(O)$_{1-2}$OR$^{61}$, —S(O)$_{1-2}$N(R$^{62}$)(R$^{63}$), —OS(O)$_{1-2}$N(R$^{62}$)(R$^{63}$), —N(R$^{61}$)S(O)$_{1-2}$R$^{61}$, —NR$^{61}$S(O)$_{1-2}$OR$^{61}$, —NR$^{61}$S(O)$_{1-2}$N(R$^{62}$)(R$^{63}$), —C(=W)R$^{61}$, —C(=O)WR$^{61}$, —WC(=W) R$^{61}$, and —WC(=W)WR$^{61}$, preferably hydrogen, halogen, cyano, (C$_1$-C$_6$)haloalkyl and (C$_1$-C$_6$)alkyl, in other embodiments the CH$_2$ and/or CH groups of said ring structures may be each independently substituted with one or more halogen, preferably fluorine, i.e. the respective CH$_2$ or CH group is a CHF, CF$_2$ and CF group, in other embodiments R$^3$ is NHR$^4$, in other embodiments R$^3$ is NR$^5$R$^6$.

In some embodiments $R^4$ is selected from the group consisting of

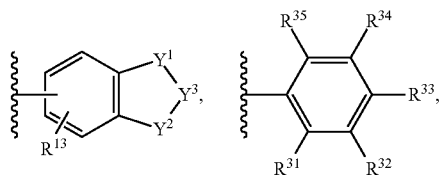

in other embodiments $R^4$ is

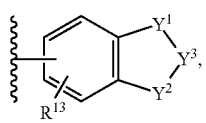

in other embodiments $R^4$ is

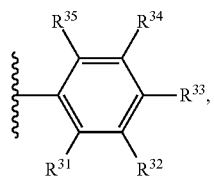

in other embodiments $R^4$ is substituted or unsubstituted naphthyl, in other embodiments $R^4$ is unsubstituted naphthyl, in other embodiments $R^4$ is substituted naphthyl.

In some embodiments $Y^1$ and $Y^2$ are each independently selected from the group consisting of O, S and $CH_2$, in other embodiments $Y^1$ and $Y^2$ are each independently selected from O and S; in other embodiments $Y^1$ and $Y^2$ are O, in other embodiments $Y^1$ and $Y^2$ are S, in other embodiments $Y^1$ and $Y^2$ are $CH_2$, In some embodiments $R^{11}$ and $R^{12}$ are hydrogen, in other embodiments $R^{11}$ and $R^{12}$ are halogen, in other embodiments $R^{11}$ and $R^{12}$ are fluorine.

In some embodiments $R^{13}$ is selected from hydrogen, $(C_1-C_6)$alkyl, $(C_1-C_6)$haloalkyl and halogen, in other embodiments $R^{13}$ is selected from hydrogen, $(C_1-C_5)$alkyl, $(C_1-C_5)$haloalkyl and halogen, in other embodiments $R^{13}$ is selected from hydrogen, $(C_1-C_4)$alkyl, $(C_1-C_4)$haloalkyl and halogen, in other embodiments $R^{13}$ is selected from hydrogen, $(C_1-C_3)$alkyl, $(C_1-C_3)$haloalkyl and halogen, in other embodiments $R^{13}$ is selected from hydrogen, $(C_1-C_2)$alkyl, $(C_1-C_2)$haloalkyl and halogen, in other embodiments $R^{13}$ is selected from hydrogen, methyl, —$CF_3$ and halogen, in other embodiments $R^{13}$ is selected from hydrogen, $(C_1-C_5)$ alkyl, and halogen, in other embodiments $R^{13}$ is selected from hydrogen, and halogen, in other embodiments $R^{13}$ is hydrogen.

In some embodiments $R^{31}$, $R^{32}$, $R^{33}$, $R^{34}$ and $R^{35}$ are each independently selected from the group consisting of hydrogen, substituted or unsubstituted $(C_1-C_6)$alkyl, $(C_1-C_6)$haloalkyl, —C(O)$R^{14}$, substituted or unsubstituted $(C_6-C_{14})$aryl$(C_1-C_6)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_6)$alkyl, $(C_1-C_6)$haloalkyl, —C(O)$R^{14}$, $(C_6-C_{14})$aryl$(C_1-C_6)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_5)$alkyl, $(C_1-C_5)$haloalkyl, —C(O)$R^{14}$, $(C_6-C_{10})$aryl$(C_1-C_6)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_4)$alkyl, $(C_1-C_4)$haloalkyl, —C(O)$R^{14}$, $(C_6)$aryl$(C_1-C_4)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_3)$alkyl, $(C_1-C_3)$haloalkyl, —C(O)$R^{14}$, $(C_6)$aryl$(C_1-C_2)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_2)$alkyl, $(C_1-C_2)$haloalkyl, —C(O)$R^{14}$, $(C_6)$aryl$(C_1-C_2)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, methyl, —$CF_3$, —C(O)$R^{14}$, benzyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_6)$alkyl, $(C_1-C_6)$haloalkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_6)$alkyl, $(C_1-C_6)$haloalkyl and —$OR^{15}$, in other embodiments $R^{31}$, $R^{32}$, $R^{33}$, $R^{34}$ and $R^{35}$ are each independently selected from the group consisting of hydrogen, $(C_1-C_6)$alkyl and $(C_1-C_6)$haloalkyl, in other embodiments $R^{31}$, $R^{32}$, $R^{33}$, $R^{34}$ and $R^{35}$ are each independently selected from the group consisting of $(C_1-C_6)$alkyl and $(C_1-C_6)$haloalkyl, in other embodiments $R^{31}$, $R^{32}$, $R^{33}$, $R^{34}$ and $R^{35}$ are each independently selected from the group consisting of hydrogen, $(C_1-C_4)$alkyl and $(C_1-C_4)$haloalkyl, in other embodiments $R^{31}$, $R^{32}$, $R^{33}$, $R^{34}$ and $R^{35}$ are each independently selected from the group consisting of hydrogen, $(C_1-C_3)$alkyl and $(C_1-C_3)$haloalkyl, in other embodiments $R^{31}$, $R^{32}$, $R^{33}$, $R^{34}$ and $R^{35}$ are each independently selected from the group consisting of hydrogen, $(C_1-C_2)$alkyl and $(C_1-C_2)$haloalkyl, in other embodiments $R^{31}$, $R^{32}$, $R^{33}$, $R^{34}$ and $R^{35}$ are each independently selected from the group consisting of hydrogen, methyl, and —$CF_3$, in other embodiments $R^{31}$ and $R^{35}$ are hydrogen and $R^{32}$ $R^{33}$ and $R^{34}$ are selected from the group consisting of hydrogen, $(C_1-C_6)$alkyl, $(C_1-C_6)$haloalkyl, —C(O)$R^{14}$, $(C_6-C_{14})$aryl$(C_1-C_6)$alkyl, —$OR^{15}$ and —NH—C(O)—NH—B, in other embodiments $R^{31}$ and $R^{35}$ are hydrogen and $R^{32}$ $R^{33}$ and $R^{34}$ are selected from the group consisting of hydrogen, $(C_1-C_6)$ alkyl and $(C_1-C_6)$haloalkyl, in other embodiments $R^{31}$, $R^{32}$, $R^{34}$ and $R^{35}$ are hydrogen and $R^{33}$ is selected from the group consisting of hydrogen, $(C_1-C_6)$alkyl, $(C_1-C_6)$haloalkyl, —C(O)$R^{14}$, $(C_6-C_{14})$aryl$(C_1-C_6)$alkyl, —$OR^{15}$ and —NH—C(O)—NH—B; in other embodiments $R^{31}$, $R^{32}$, $R^{34}$ and $R^{35}$ are hydrogen and $R^{33}$ is selected from the group consisting of hydrogen, $(C_1-C_6)$alkyl and $(C_1-C_6)$haloalkyl, in other embodiments $R^{31}$, $R^{33}$, $R^{34}$ and $R^{35}$ are hydrogen and $R^{32}$ is —NH—C(O)—NH—B.

In some embodiments $R^{14}$ is selected from —O—$(C_1-C_6)$alkyl, —O—$(C_1-C_6)$haloalkyl, —NH—$CH_3$ and $(C_6-C_{14})$aryl, in other embodiments $R^{14}$ is selected from —O—$(C_1-C_6)$alkyl and —O—$(C_1-C_6)$haloalkyl, in other embodiments $R^{14}$ is —O—$(C_1-C_6)$alkyl.

In some embodiments $R^{15}$ is selected from the group consisting of $(C_1-C_6)$alkyl, $(C_1-C_6)$haloalkyl and $(C_6-C_{14})$aryl, in other embodiments $R^{15}$ is selected from the group consisting of $(C_1-C_6)$alkyl and $(C_1-C_6)$haloalkyl, in other embodiments $R^{15}$ is $(C_1-C_6)$alkyl, in other embodiments $R^{15}$ is $(C_1-C_4)$alkyl, in other embodiments $R^{15}$ is $(C_1-C_3)$alkyl, in other embodiments $R^{15}$ is $(C_1-C_2)$alkyl, in other embodiments $R^{15}$ is methyl, in other embodiments $R^{15}$ is $(C_1-C_6)$haloalkyl, in other embodiments $R^{15}$ is $(C_1-C_4)$haloalkyl, in other embodiments $R^{15}$ is $(C_1-C_3)$haloalkyl, in other embodiments $R^{15}$ is $(C_1-C_2)$haloalkyl, in other embodiments $R^{15}$ is —$CF_3$.

In some embodiments B is phenyl, optionally substituted with 1-3 substituents independently selected from the group consisting of hydrogen, $(C_1-C_6)$alkyl, $(C_1-C_6)$haloalkyl, halogen, cyano, nitro, —O—$(C_1-C_6)$alkyl and —O—$(C_1-C_6)$haloalkyl, in other embodiments B is phenyl substituted with 1-3 substituents independently selected from the group consisting of hydrogen, $(C_1-C_6)$alkyl, $(C_1-C_6)$haloalkyl and halogen, in other embodiments B is phenyl substituted with 1-3 substituents independently selected from the group consisting of hydrogen, $(C_1-C_4)$alkyl, $(C_1-C_4)$haloalkyl and halogen, in other embodiments B is phenyl substituted with 1-3 substituents independently selected from the group consisting of hydrogen, $(C_1-C_3)$alkyl, $(C_1-C_3)$haloalkyl and halogen, in other embodiments B is phenyl substituted with 1-3 substituents independently selected from the group consisting of hydrogen, $(C_1-C_2)$alkyl, $(C_1-C_2)$haloalkyl and halogen, in other embodiments B is phenyl substituted with 1-3 substituents independently selected from the group consisting of hydrogen, methyl, $(C_1)$haloalkyl and halogen.

In some embodiments $R^5$ and $R^6$ are each independently selected from the group consisting of substituted or unsubstituted $(C_1-C_6)$alkyl, substituted or unsubstituted $(C_1-C_6)$heteroalkyl, substituted or unsubstituted $(C_2-C_6)$alkenyl, substituted and unsubstituted $(C_3-C_{14})$heteroaryl$(C_5-C_6)$alkyl and substituted or unsubstituted $(C_6-C_{10})$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of substituted or unsubstituted $(C_1-C_6)$alkyl, substituted or unsubstituted $(C_1-C_6)$heteroalkyl, substituted or unsubstituted $(C_2-C_6)$alkenyl, substituted and unsubstituted $(C_3-C_{14})$heteroaryl$(C_1-C_6)$alkyl and substituted or unsubstituted $(C_6-C_{10})$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$. In other embodiments $R^5$ and $R^6$ are each independently selected from the group consisting of $(C_1-C_6)$alkyl, $(C_1-C_6)$heteroalkyl, $(C_2-C_6)$alkenyl, $(C_3-C_{14})$heteroaryl$(C_1-C_6)$alkyl and $(C_6-C_{10})$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of $(C_1-C_4)$alkyl, $(C_1-C_4)$heteroalkyl, $(C_2-C_4)$alkenyl and $(C_6)$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of $(C_1-C_3)$alkyl, $(C_1-C_3)$heteroalkyl, $(C_2-C_3)$alkenyl and $(C_6)$aryl$(C_1-C_4)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of $(C_1-C_4)$alkyl, $(C_1-C_4)$heteroalkyl, $(C_2-C_4)$alkenyl and $(C_6)$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five or six-membered ring, which is optionally substituted with one or more independently selected $R^{51}$; or (ii) the formed ring is imidazole, which is optionally substituted with one or more independently selected $R^{51}$. In other embodiments $R^5$ and $R^6$ join together with the nitrogen atom to which they are attached to form a ring, wherein the formed ring is selected from the group consisting of

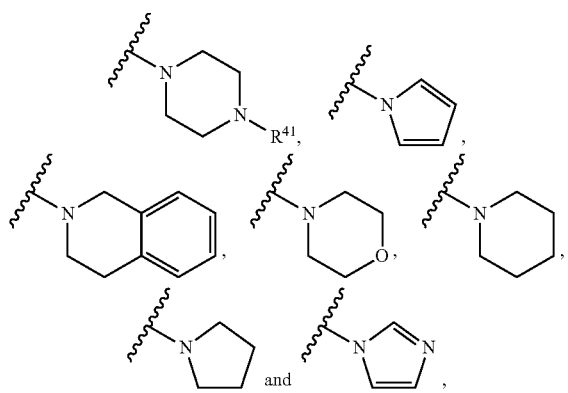

in other embodiments

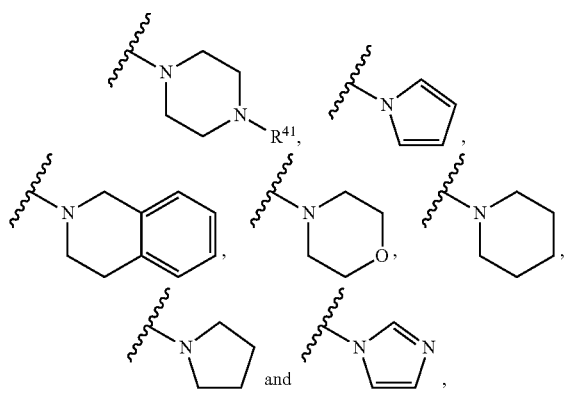

may be substituted or unsubstituted, in particular each $CH_2$ and/or CH group of said ring structures may be independently substituted with one or more residues selected from the group consisting of hydrogen, substituted or unsubstituted (C$_1$-C$_6$)alkyl, (C$_1$-C$_6$)heteroalkyl, (C$_1$-C$_6$)haloalkyl; substituted or unsubstituted (C$_2$-C$_6$)alkenyl, substituted or unsubstituted (C$_2$-C$_6$)alkynyl, substituted or unsubstituted (C$_3$-C$_6$)cycloalkyl, substituted or unsubstituted (C$_6$-C$_{10}$) aryl, substituted or unsubstituted (C$_6$-C$_{10}$)aryl(C$_1$-C$_6$)alkyl, substituted or unsubstituted (C$_3$-C$_{10}$)heteroaryl, substituted or unsubstituted (C$_3$-C$_{10}$)heteroaryl(C$_1$-C$_6$)alkyl, halogen, —CN, —NO$_2$, —N(R$^{62}$)(R$^{63}$), —N(R$^{61}$)(OR$^{61}$), —S(O)$_{0-2}$R$^{61}$, —S(O)$_{1-2}$OR$^{61}$, —OS(O)$_{1-2}$R$^{61}$, —OS(O)$_{1-2}$OR$^{61}$, —S(O)$_{1-2}$N(R$^{62}$)(R$^{63}$), —OS(O)$_{1-2}$N(R$^{62}$)(R$^{63}$), —N(R$^{61}$)S(O)$_{1-2}$R$^{61}$, —NR$^{61}$S(O)$_{1-2}$OR$^{61}$, —NR$^{61}$S(O)$_{1-2}$N(R$^{62}$)(R$^{63}$), —C(=W)R$^{61}$, —C(=W)WR$^{61}$, —WC(=W)R$^{61}$, and —WC(=W)WR$^{61}$, preferably hydrogen, halogen, cyano, (C$_1$-C$_6$)haloalkyl and (C$_1$-C$_6$)alkyl, in other embodiments each CH$_2$ and/or CH group of said ring structures may be each independently substituted with one or more halogen, preferably fluorine, i.e. the respective CH$_2$ or CH group is a CHF, CF$_2$ and CF group.

In some embodiments R$^{41}$ is selected from the group consisting of hydrogen (C$_1$-C$_6$)alkyl, (C$_1$-C$_6$)heteroalkyl, (C$_1$-C$_6$)haloalkyl; (C$_2$-C$_6$)alkenyl, (C$_2$-C$_6$)alkynyl, (C$_3$-C$_8$)cycloalkyl (C$_6$-C$_{10}$)aryl, (C$_6$-C$_{10}$)aryl(C$_1$-C$_6$)alkyl, (C$_3$-C$_{10}$)heteroaryl, (C$_3$-C$_{10}$)heteroaryl(C$_1$-C$_6$)alkyl, —S(O)$_{1-2}$OR$^{61}$, —S(O)$_{1-2}$N(R$^{62}$)(R$^{63}$), —C(O)R$^{42}$, —C(O)N(R$^{42}$)(R$^{43}$), —C(S)N(R$^{42}$)(R$^{43}$), —C(S)OR$^{42}$ and —C(O)OR$^{42}$.

In some embodiments R$^{42}$ and R$^{43}$ are each independently selected from the group consisting of hydrogen (C$_1$-C$_6$)alkyl, (C$_1$-C$_6$)heteroalkyl, (C$_1$-C$_6$)haloalkyl; (C$_2$-C$_6$)alkenyl, (C$_2$-C$_6$)alkynyl, (C$_3$-C$_8$)cycloalkyl (C$_6$-C$_{10}$)aryl, (C$_6$-C$_{10}$)aryl(C$_1$-C$_6$)alkyl, (C$_3$-C$_{10}$)heteroaryl, (C$_3$-C$_{10}$)heteroaryl(C$_1$-C$_6$)alkyl, preferably selected from the group consisting of hydrogen (C$_1$-C$_6$)alkyl, (C$_1$-C$_6$)heteroalkyl, (C$_1$-C$_6$)haloalkyl; (C$_3$-C$_8$)cycloalkyl (C$_6$-C$_{10}$)aryl, (C$_6$-C$_{10}$)aryl(C$_1$-C$_6$)alkyl, (C$_3$-C$_{10}$)heteroaryl, (C$_3$-C$_{10}$)heteroaryl(C$_1$-C$_6$)alkyl.

In some embodiments R$^{51}$ is selected from the group consisting of hydrogen, substituted or unsubstituted (C$_1$-C$_6$)alkyl, (C$_1$-C$_6$)heteroalkyl, (C$_1$-C$_6$)haloalkyl; substituted or unsubstituted (C$_2$-C$_6$)alkenyl, substituted or unsubstituted (C$_2$-C$_6$)alkynyl, substituted or unsubstituted (C$_3$-C$_8$)cycloalkyl, substituted or unsubstituted (C$_6$-C$_{10}$)aryl, substituted or unsubstituted (C$_6$-C$_{10}$)aryl(C$_1$-C$_6$)alkyl, substituted or unsubstituted (C$_3$-C$_{10}$)heteroaryl, substituted or unsubstituted (C$_3$-C$_{10}$)heteroaryl(C$_1$-C$_6$)alkyl, halogen, —CN, —NO$_2$, —OR$^{61}$, —N(R$^{62}$)(R$^{63}$), —N(R$^{61}$)(OR$^{61}$), —S(O)$_{02}$R$^{61}$, —S(O)$_{1-2}$OR$^{61}$, —OS(O)$_{1-2}$R$^{61}$, —OS(O)$_{1-2}$OR$^{61}$, —S(O)$_{1-2}$N(R$^{62}$)(R$^{63}$), —OS(O)$_{1-2}$N(R$^{62}$)(R$^{63}$), —N(R$^{61}$)S(O)$_{1-2}$R$^{61}$, —NR$^{61}$S(O)$_{1-2}$OR$^{61}$, —NR$^{61}$S(O)$_{1-2}$N(R$^{62}$)(R$^{63}$), —C(=W)R$^{61}$, —C(=W)WR$^{61}$, —WC(=W)R$^{61}$, and —WC(=W)WR$^{61}$. In other embodiments R$^{51}$ is selected from the group consisting of hydrogen, (C$_1$-C$_6$)alkyl, (C$_1$-C$_6$)heteroalkyl, (C$_1$-C$_6$)haloalkyl; (C$_2$-C$_6$)alkenyl, (C$_2$-C$_6$)alkynyl, (C$_3$-C$_8$)cycloalkyl, (C$_6$-C$_{10}$)aryl, (C$_6$-C$_{10}$)aryl(C$_1$-C$_6$)alkyl, (C$_3$-C$_{10}$)heteroaryl, (C$_3$-C$_{10}$)heteroaryl(C$_1$-C$_6$)alkyl, halogen, —CN, —NO$_2$, —OR$^{61}$, —N(R$^{62}$)(R$^{63}$), —N(R$^{61}$)(OR$^{61}$), —S(O)$_{0-2}$R$^{61}$, —S(O)$_{1-2}$OR$^{61}$, —OS(O)$_{1-2}$R$^{61}$, —OS(O)$_{1-2}$OR$^{61}$, —S(O)$_{1-2}$N(R$^{62}$)(R$^{63}$), —OS(O)$_{1-2}$N(R$^{62}$)(R$^{63}$), —N(R$^{61}$)S(O)$_{1-2}$R$^{61}$, —NR$^{61}$S(O)$_{1-2}$OR$^{61}$, —NR$^{61}$S(O)$_{1-2}$N(R$^{62}$)(R$^{63}$), —C(=W)R$^{61}$, —C(=W)WR$^{61}$, —WC(=W)R$^{61}$, and —WC(=W)WR$^{61}$.

In some embodiments R$^{61}$ is, in each case, selected from the group consisting of —H, alkyl, alkenyl, alkynyl, cycloalkyl, aryl, heteroaryl, and heterocyclyl, preferably hydrogen and C$_1$-C$_6$alkyl.

In some embodiments R$^{62}$ and R$^{63}$ are, in each case, independently selected from the group consisting of —H, alkyl, alkenyl, alkynyl, cycloalkyl, aryl, heteroaryl, and heterocyclyl.

In some embodiments W is independently selected from O, S, and N(R$^{64}$), in other embodiments W is O; in other embodiments W is S, in other embodiments W is N(R$^{64}$).

In some embodiments R$^{64}$ is independently selected from the group consisting of —H, alkyl, alkenyl, alkynyl, cycloalkyl, aryl, heteroaryl, heterocyclyl, and —OR$^{61}$, in other embodiments R$^{64}$ is independently selected from the group consisting of —H, alkyl, cycloalkyl, aryl, heteroaryl, heterocyclyl, and —OR$^{61}$.

In some embodiments X is O, in other embodiments X is S.

In some embodiments the compound for use and the compound of the pharmaceutical composition for use, as disclosed herein, are characterized by having a structure according to Formula IA

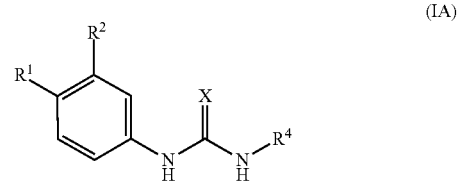

(IA)

wherein
R$^1$ is selected from the group consisting of hydrogen, cyano and halogen;
R$^2$ is (C$_1$-C$_6$)alkyl or (C$_1$-C$_6$)haloalkyl.
R$^4$ is selected from the group consisting of

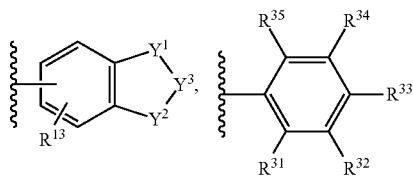

and substituted or unsubstituted naphthyl;
Y$^1$ and Y$^2$ are each independently selected from the group consisting of O, S, SO, SO$_2$ and CH$_2$;
Y$^3$ is CR$^{11}$R$^{12}$;
R$^{11}$ and R$^{12}$ are each independently selected from the group consisting of hydrogen and halogen;
R$^{13}$ is selected from the group consisting of hydrogen, (C$_1$-C$_6$)alkyl, (C$_1$-C$_6$)haloalkyl and halogen, preferably hydrogen;
R$^{31}$, R$^{32}$, R$^{33}$, R$^{34}$ and R$^{35}$ are each independently selected from the group consisting of hydrogen, substituted or unsubstituted (C$_1$-C$_6$)alkyl, (C$_1$-C$_6$)haloalkyl, —C(O)R$^{14}$, substituted or unsubstituted (C$_6$-C$_{14}$)aryl(C$_1$-C$_6$)alkyl, —OR$^{15}$ and —NH—C(O)—NH—B
R$^{14}$ is selected from —O—(C$_1$-C$_6$)alkyl, —O—(C$_1$-C$_6$)haloalkyl, —NH—CH$_3$ and substituted or unsubstituted (C$_6$-C$_{14}$)aryl;
R$^{15}$ is selected from the group consisting of (C$_1$-C$_6$)alkyl, (C$_1$-C$_6$)haloalkyl and substituted or unsubstituted (C$_6$-C$_{14}$)aryl, preferably (C$_1$-C$_6$)alkyl and (C$_1$-C$_6$)haloalkyl;

B is phenyl, optionally substituted with 1-3 substituents independently selected from the group consisting of hydrogen, $(C_1-C_6)$alkyl, $(C_1-C_6)$haloalkyl, halogen, cyano, nitro, —O—$(C_1-C_6)$alkyl and —O—$(C_1-C_6)$haloalkyl, preferably hydrogen, $(C_1-C_6)$alkyl, $(C_1-C_6)$haloalkyl and halogen;

X is selected from O or S;

or a pharmaceutically acceptable salt, solvate or hydrate thereof.

In some embodiments $R^1$ is selected from hydrogen and halogen, in other embodiments $R^1$ is halogen, in in other embodiments $R^1$ is chlorine.

In some embodiments $R^2$ is $(C_1-C_6)$alkyl, in other embodiments $R^2$ is $(C_1-C_6)$alkyl, in other embodiments $R^2$ is $(C_1-C_4)$alkyl, in other embodiments $R^2$ is $(C_1-C_3)$alkyl, in other embodiments $R^2$ is $(C_1-C_2)$alkyl, in other embodiments $R^2$ is methyl. In some embodiments $R^2$ is $(C_1-C_6)$haloalkyl, in other embodiments $R^2$ is $(C_1-C_6)$haloalkyl, in other embodiments $R^2$ is $(C_1-C_4)$haloalkyl, in other embodiments $R^2$ is $(C_1-C_3)$haloalkyl, in other embodiments $R^2$ is $(C_1-C_2)$haloalkyl, in other embodiments $R^2$ is —$CF_3$.

In some embodiments $R^4$ is selected from the group consisting of

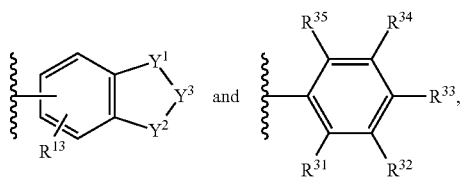

in other embodiments $R^4$ is

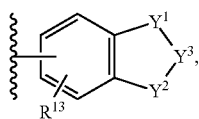

in other embodiments $R^4$ is

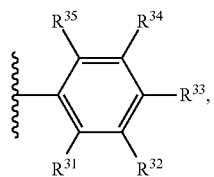

in other embodiments $R^4$ is substituted or unsubstituted naphthyl, in other embodiments $R^4$ is unsubstituted naphthyl, in other embodiments $R^4$ is substituted naphthyl.

In some embodiments $Y^1$ and $Y^2$ are each independently selected from the group consisting of O, S and $CH_2$, in other embodiments $Y^1$ and $Y^2$ are each independently selected from O and S; in other embodiments $Y^1$ and $Y^2$ are O, in other embodiments $Y^1$ and $Y^2$ are S, in other embodiments $Y^1$ and $Y^2$ are $CH_2$.

In some embodiments $R^{11}$ and $R^{12}$ are hydrogen, in other embodiments $R^{11}$ and $R^{12}$ are halogen, in other embodiments $R^{11}$ and $R^{12}$ are fluorine.

In some embodiments $R^{13}$ is selected from hydrogen, $(C_1-C_6)$alkyl, $(C_1-C_6)$haloalkyl and halogen, in other embodiments $R^{13}$ is selected from hydrogen, $(C_1-C_6)$alkyl, $(C_1-C_6)$haloalkyl and halogen, in other embodiments $R^{13}$ is selected from hydrogen, $(C_1-C_4)$alkyl, $(C_1-C_4)$haloalkyl and halogen, in other embodiments $R^{13}$ is selected from hydrogen, $(C_1-C_3)$alkyl, $(C_1-C_3)$haloalkyl and halogen, in other embodiments $R^{13}$ is selected from hydrogen, $(C_1-C_2)$alkyl, $(C_1-C_2)$haloalkyl and halogen, in other embodiments $R^{13}$ is selected from hydrogen, methyl, —$CF_3$ and halogen, in other embodiments $R^{13}$ is selected from hydrogen, $(C_1-C_5)$alkyl, and halogen, in other embodiments $R^{13}$ is selected from hydrogen, and halogen, in other embodiments $R^{13}$ is hydrogen.

In some embodiments $R^{31}$, $R^{32}$, $R^{33}$, $R^{34}$ and $R^{35}$ are each independently selected from the group consisting of hydrogen, substituted or unsubstituted $(C_1-C_6)$alkyl, $(C_1-C_6)$haloalkyl, —$C(O)R^{14}$, substituted or unsubstituted $(C_6-C_{14})$aryl$(C_1-C_6)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_6)$alkyl, $(C_1-C_6)$haloalkyl, —$C(O)R^{14}$, $(C_6-C_{14})$aryl$(C_1-C_6)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_5)$alkyl, $(C_1-C_6)$haloalkyl, —$C(O)R^{14}$, $(C_6-C_{10})$aryl$(C_1-C_6)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_4)$alkyl, $(C_1-C_4)$haloalkyl, —$C(O)R^{14}$, $(C_6)$aryl$(C_1-C_4)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_3)$alkyl, $(C_1-C_3)$haloalkyl, —$C(O)R^{14}$, $(C_6)$aryl$(C_1-C_2)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_2)$alkyl, $(C_1-C_2)$haloalkyl, —$C(O)R^{14}$, $(C_6)$aryl$(C_1-C_2)$alkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, methyl, —$CF_3$, —$C(O)R^{14}$, benzyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_6)$alkyl, $(C_1-C_6)$haloalkyl, —$OR^{15}$ and —NH—C(O)—NH—B, in other embodiments $R^{31}$, $R^{32}$, $R^{33}$, $R^{34}$ and $R^{35}$ are each independently selected from the group consisting of hydrogen, $(C_1-C_6)$alkyl, $(C_1-C_6)$haloalkyl and —$OR^{15}$, in other embodiments $R^{31}$, $R^{32}$, $R^{33}$, $R^{34}$ and $R^{35}$ are each independently selected from the group consisting of hydrogen, $(C_1-C_6)$alkyl and $(C_1-C_6)$haloalkyl, in other embodiments $R^{31}$, $R^{32}$, $R^{33}$, $R^{34}$ and $R^{35}$ are each independently selected from the group consisting of $(C_1-C_6)$alkyl and $(C_1-C_6)$haloalkyl, in other embodiments $R^{31}$, $R^{32}$, $R^{33}$, $R^{34}$ and $R^{35}$ are each independently selected from the group consisting of hydrogen, $(C_1-C_4)$alkyl and $(C_1-C_4)$haloalkyl, in other embodiments $R^{31}$, $R^{32}$, $R^{33}$, $R^{34}$ and $R^{35}$ are each independently selected from the group consisting of hydrogen, $(C_1-C_3)$alkyl and $(C_1-C_3)$haloalkyl, in other embodiments $R^{31}$, $R^{32}$, $R^{33}$, $R^{34}$ and $R^{35}$ are each independently selected from the group consisting of hydrogen, $(C_1-C_2)$alkyl and $(C_1-C_2)$haloalkyl, in other embodiments $R^{31}$, $R^{32}$, $R^{33}$, $R^{34}$ and $R^{35}$ are each independently selected from the group consisting of hydrogen, methyl, and —$CF_3$, in other embodiments $R^{31}$ and $R^{35}$ are hydrogen and $R^{32}$, $R^{33}$ and $R^{34}$ are selected from the group consisting of hydrogen, $(C_1-C_6)$alkyl, $(C_1-C_6)$haloalkyl, —$C(O)R^{14}$, $(C_6-C_{14})$aryl$(C_1-C_6)$alkyl, —$OR^{15}$ and —NH—C(O)—NH—B, in other embodiments $R^{31}$ and $R^{35}$ are hydrogen and $R^{32}$, $R^{33}$ and $R^{34}$ are selected from the group consisting of hydrogen, $(C_1-C_6)$alkyl and $(C_1-C_6)$haloalkyl, in other embodiments $R^{31}$, $R^{32}$, $R^{34}$ and $R^{35}$ are hydrogen and $R^{33}$ is selected from the group consisting of hydrogen, $(C_1-C_6)$ alkyl, $(C_1-C_6)$haloalkyl, —C(O)$R^{14}$, $(C_6-C_{14})$aryl$(C_1-C_6)$ alkyl, —O$R^{15}$ and —NH—C(O)—NH—B; in other embodiments $R^{31}$, $R^{32}$, $R^{34}$ and $R^{35}$ are hydrogen and $R^{33}$ is selected from the group consisting of hydrogen, $(C_1-C_6)$ alkyl and $(C_1-C_6)$haloalkyl, in other embodiments $R^{31}$, $R^{33}$, $R^{34}$ and $R^{35}$ are hydrogen and $R^{32}$ is —NH—C(O)—NH—B.

In some embodiments $R^{14}$ is selected from —O—$(C_1-C_6)$alkyl, —O—$(C_1-C_6)$haloalkyl, —NH—CH$_3$ and $(C_6-C_{14})$aryl, in other embodiments $R^{14}$ is selected from —O—$(C_1-C_6)$alkyl and —O—$(C_1-C_6)$haloalkyl, in other embodiments $R^{14}$ is —O—$(C_1-C_6)$alkyl.

In some embodiments $R^{15}$ is selected from the group consisting of $(C_1-C_6)$alkyl, $(C_1-C_6)$haloalkyl and $(C_6-C_{14})$ aryl, in other embodiments $R^{15}$ is selected from the group consisting of $(C_1-C_6)$alkyl and $(C_1-C_6)$haloalkyl, in other embodiments $R^{15}$ is $(C_1-C_6)$alkyl, in other embodiments $R^{15}$ is $(C_1-C_4)$alkyl, in other embodiments $R^{15}$ is $(C_1-C_3)$alkyl, in other embodiments $R^{15}$ is $(C_1-C_2)$alkyl, in other embodiments $R^{15}$ is methyl, in other embodiments $R^{15}$ is $(C_1-C_6)$ haloalkyl, in other embodiments $R^{15}$ is $(C_1-C_4)$haloalkyl, in other embodiments $R^{15}$ is $(C_1-C_3)$haloalkyl, in other embodiments $R^{15}$ is $(C_1-C_2)$haloalkyl, in other embodiments $R^{15}$ is $CF_3$.

In some embodiments B is phenyl, optionally substituted with 1-3 substituents independently selected from the group consisting of hydrogen, $(C_1-C_6)$alkyl, $(C_1-C_6)$haloalkyl, halogen, cyano, nitro, —O—$(C_1-C_6)$alkyl and —O—$(C_1-C_6)$haloalkyl, in other embodiments B is phenyl substituted with 1-3 substituents independently selected from the group consisting of hydrogen, $(C_1-C_6)$alkyl, $(C_1-C_6)$haloalkyl and halogen, in other embodiments B is phenyl substituted with 1-3 substituents independently selected from the group consisting of hydrogen, $(C_1-C_4)$alkyl, $(C_1-C_4)$haloalkyl and halogen, in other embodiments B is phenyl substituted with 1-3 substituents independently selected from the group consisting of hydrogen, $(C_1-C_3)$alkyl, $(C_1-C_3)$haloalkyl and halogen, in other embodiments B is phenyl substituted with 1-3 substituents independently selected from the group consisting of hydrogen, $(C_1-C_2)$alkyl, $(C_1-C_2)$haloalkyl and halogen, in other embodiments B is phenyl substituted with 1-3 substituents independently selected from the group consisting of hydrogen, methyl, $(C_1)$haloalkyl and halogen.

In some embodiments X is O, in other embodiments X is S.

In some embodiments the compound for use and the compound of the pharmaceutical composition for use having a structure according to Formula I or Formula IA, as disclosed herein, are further characterized in that
$R^{31}$, $R^{33}$, $R^{34}$ and $R^{35}$ are hydrogen;
$R^{32}$ is hydrogen or —NH—C(O)—NH—B;
$R^{14}$ is selected from the group consisting of —O—$(C_1-C_6)$alkyl, —O—$(C_1-C_6)$haloalkyl and substituted or unsubstituted phenyl; and
$R^{15}$ is $(C_1-C_6)$alkyl or $(C_1-C_6)$haloalkyl.

In some embodiments the compound for use and the compound of the pharmaceutical composition for use having a structure according to Formula I or Formula IA, as disclosed herein, are further characterized in that
$R^{31}$, $R^{32}$, $R^{34}$ and $R^{35}$ are hydrogen
$R^{33}$ is selected from the group consisting of hydrogen, $(C_1-C_6)$alkyl, —CH$_2$—$R^{16}$—C(O)—$R^{14}$ and —O$R^{15}$, preferably hydrogen, $(C_1-C_6)$alkyl and —O$R^{15}$;
$R^{14}$ is substituted or unsubstituted phenyl, preferably unsubstituted phenyl;

$R^{15}$ is $(C_1-C_6)$alkyl or $(C_1-C_6)$haloalkyl, preferably $(C_1-C_6)$alkyl; and
$R^{16}$ is substituted or unsubstituted phenyl, preferably unsubstituted phenyl.

In some embodiments the compound for use and the compound of the pharmaceutical composition for use having a structure according to Formula I or Formula IA, as disclosed herein, are further characterized in that
$R^4$ is

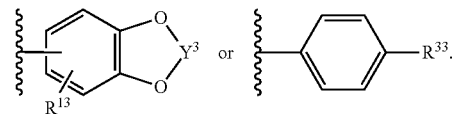

In some embodiments the compound for use and the compound of the pharmaceutical composition for use having a structure according to Formula I or Formula IA, as disclosed herein, are further characterized in that,

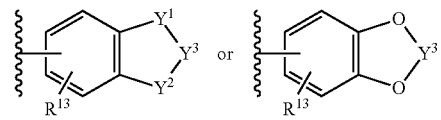

are selected from the group consisting of

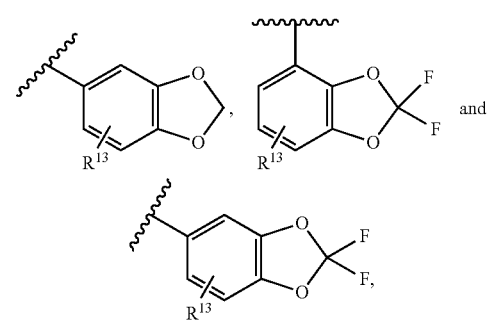

preferably

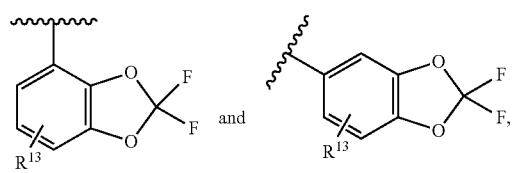

more preferably

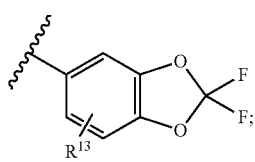

and
$R^{13}$ is hydrogen or halogen, preferably hydrogen.

In some embodiments the compound for use and the compound of the pharmaceutical composition for use having a structure according to Formula I or Formula IA, as disclosed herein, are further characterized in that,

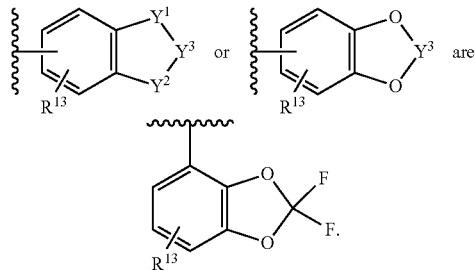

In some embodiments the compound for use and the compound of the pharmaceutical composition for use having a structure according to Formula I or Formula IA, as disclosed herein, are further characterized in that, $R^1$ is halogen, preferably chlorine; $R^2$ is $-CH_3$ or $-CF_3$, preferably $-CF_3$.

In some embodiments the compound for use and the compound of the pharmaceutical composition for use, as disclosed herein, are characterized by having a structure according to Formula IB

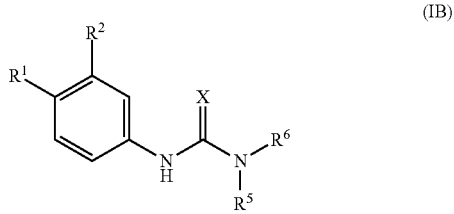

(IB)

wherein
$R^1$ is selected from the group consisting of hydrogen, cyano and halogen, preferably hydrogen and halogen;
$R^2$ is $(C_1-C_6)$alkyl or $(C_1-C_6)$haloalkyl;
$R^5$ and $R^6$ are each independently selected from the group consisting of substituted or unsubstituted $(C_1-C_6)$alkyl, substituted or unsubstituted $(C_1-C_6)$heteroalkyl, substituted or unsubstituted $(C_2-C_6)$alkenyl, substituted or unsubstituted $(C_3-C_{14})$aryl$(C_1-C_6)$alkyl and substituted or unsubstituted $(C_6-C_{10})$aryl$(C_1-C_6)$alkyl;
wherein $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$;
$R^{51}$ is selected from the group consisting of hydrogen, substituted or unsubstituted $(C_1-C_6)$alkyl, $(C_1-C_6)$heteroalkyl, $(C_1-C_6)$haloalkyl; substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{10})$aryl, substituted or unsubstituted $(C_6-C_{10})$aryl$(C_1-C_6)$alkyl, substituted or unsubstituted $(C_3-C_{10})$heteroaryl, substituted or unsubstituted $(C_3-C_{10})$heteroaryl$(C_1-C_6)$alkyl, halogen, $-CN$, $-NO_2$, $-OR^{61}$, $-N(R^{62})(R^{63})$, $-N(R^{61})(OR^{61})$, $-S(O)_{0-2}R^{61}$, $-S(O)_{1-2}OR^{61}$, $-OS(O)_{1-2}R^{61}$, $-OS(O)_{1-2}OR^{61}$, $-S(O)_{1-2}N(R^{62})(R^{63})$, $-OS(O)_{1-2}N(R^{62})(R^{63})$, $-N(R^{61})S(O)_{1-2}R^{61}$, $-NR^{61}S(O)_{1-2}OR^{61}$, $-NR^{61}S(O)_{1-2}N(R^{62})(R^{63})$, $-C(=W)R^{61}$, $-C(=W)WR^{61}$, $-WC(=W)R^{61}$, and $-WC(=W)WR^{61}$;

$R^{61}$ is, in each case, selected from the group consisting of $-H$, alkyl, alkenyl, alkynyl, cycloalkyl, aryl, heteroaryl, and heterocyclyl;

$R^{62}$ and $R^{63}$ are, in each case, independently selected from the group consisting of $-H$, alkyl, alkenyl, alkynyl, cycloalkyl, aryl, heteroaryl, and heterocyclyl;

$R^{64}$ is independently selected from the group consisting of $-H$, alkyl, alkenyl, alkynyl, cycloalkyl, aryl, heteroaryl, heterocyclyl, and $-OR^{61}$;

W is independently selected from O, S, and $N(R^{64})$;

or a pharmaceutically acceptable salt, solvate or hydrate thereof.

In some embodiments $R^5$ and $R^6$ are each independently selected from the group consisting of substituted or unsubstituted $(C_1-C_6)$alkyl, substituted or unsubstituted $(C_1-C_6)$heteroalkyl, substituted or unsubstituted $(C_2-C_6)$alkenyl, substituted and unsubstituted $(C_3-C_{14})$heteroaryl$(C_1-C_6)$alkyl and substituted or unsubstituted $(C_6-C_{10})$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of substituted or unsubstituted $(C_1-C_6)$alkyl, substituted or unsubstituted $(C_1-C_6)$heteroalkyl, substituted or unsubstituted $(C_2-C_6)$alkenyl, substituted and unsubstituted $(C_3-C_{14})$heteroaryl$(C_1-C_6)$alkyl and substituted or unsubstituted $(C_6-C_{10})$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$. In other embodiments $R^5$ and $R^6$ are each independently selected from the group consisting of $(C_1-C_6)$alkyl, $(C_1-C_6)$heteroalkyl, $(C_2-C_6)$alkenyl, $(C_3-C_{14})$heteroaryl$(C_1-C_6)$alkyl and $(C_6-C_{10})$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of $(C_1-C_4)$alkyl, $(C_1-C_4)$heteroalkyl, $(C_2-C_4)$alkenyl and $(C_6)$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of $(C_1-C_3)$alkyl, $(C_1-C_3)$heteroalkyl, $(C_2-C_3)$alkenyl and $(C_6)$aryl$(C_1-C_4)$alkyl; wherein (i) $R^5$ and $R^6$ join together with the nitrogen atom to which they are attached to form a ring, which is optionally substituted with one or more independently selected $R^{51}$, preferably wherein the formed ring is a five, six or seven-membered ring, which is optionally substituted with one or more independently selected $R^{51}$; or (ii) the formed ring is imidazole, which is optionally substituted with one or more independently selected $R^{51}$. In other embodiments $R^5$ and $R^6$ are each independently selected from the group consisting of $(C_1-C_4)$alkyl, $(C_1-C_4)$heteroalkyl, $(C_2-C_4)$alkenyl and $(C_6)$aryl$(C_1-C_6)$alkyl; wherein (i) $R^5$ and $R^6$ join together with the nitrogen atom to which they are attached to form a ring, which is optionally substituted with one or more independently selected $R^{51}$, preferably wherein the formed ring is a five or six-membered ring, which is optionally substituted with one or more independently selected $R^{51}$; or (ii) the formed ring is imidazole, which is optionally substituted with one or more independently selected $R^{51}$. In other embodiments $R^5$ and $R^6$ join together with the nitrogen atom to which they are attached to form a ring, wherein the formed ring is selected from the group consisting of

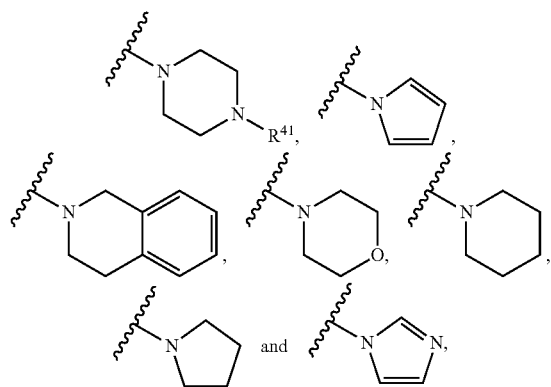

in other embodiments

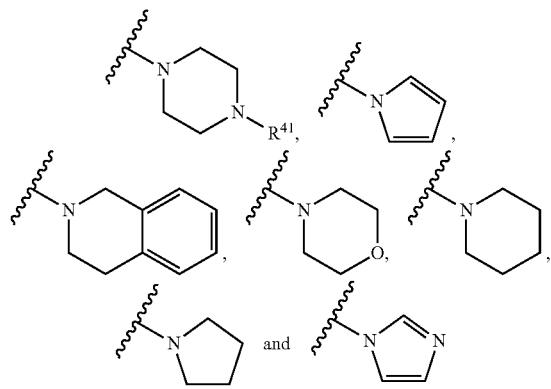

may be substituted or unsubstituted, in particular each $CH_2$ and/or CH group of said ring structures may be independently substituted with one or more residues selected from the group consisting of hydrogen, substituted or unsubstituted $(C_1-C_6)$alkyl, $(C_1-C_6)$heteroalkyl, $(C_1-C_6)$haloalkyl; substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{10})$aryl, substituted or unsubstituted $(C_6-C_{10})$aryl$(C_1-C_6)$alkyl, substituted or unsubstituted $(C_3-C_{10})$heteroaryl, substituted or unsubstituted $(C_3-C_{10})$ heteroaryl $(C_1-C_6)$alkyl, halogen, —CN, —$NO_2$, —$OR^{61}$, —$N(R^{62})(R^{63})$, —$N(R^{61})(OR^{61})$, —$S(O)_{0-2}R^{61}$, —$S(O)_{1-2}OR^{61}$, —$OS(O)_{1-2}R^{61}$, —$OS(O)_{1-2}OR^{61}$, —$S(O)_{1-2}N(R^{62})(R^{63})$, —$OS(O)_{1-2}N(R^{62})(R^{63})$, —$N(R^{51})S(O)_{1-2}R^{61}$, —$NR^{61}S(O)_{1-2}OR^{61}$, —$NR^{61}S(O)_{1-2}N(R^{62})(R^{63})$, —$C(=W)R^{61}$, —$C(=W)WR^{61}$, —$WC(=W)R^{61}$, and —$WC(=W)WR^{61}$, preferably hydrogen, halogen, cyano, $(C_1-C_6)$haloalkyl and $(C_1-C_6)$alkyl, in other embodiments each $CH_2$ and/or CH group of said ring structures may be independently substituted with one or more halogen, preferably fluorine, i.e. the respective $CH_2$ or CH group is a CHF, $CF_2$ and CF group.

In some embodiments $R^{41}$ is selected from the group consisting of hydrogen $(C_1-C_6)$alkyl, $(C_1-C_6)$heteroalkyl, $(C_1-C_6)$haloalkyl; $(C_2-C_6)$alkenyl, $(C_2-C_6)$alkynyl, $(C_3-C_8)$cycloalkyl $(C_6-C_{10})$aryl, $(C_6-C_{10})$aryl$(C_1-C_6)$alkyl, $(C_3-C_{10})$heteroaryl, $(C_3-C_{10})$heteroaryl$(C_1-C_6)$alkyl, —$S(O)_{1-2}OR^{61}$, —$S(O)_{1-2}N(R^{62})(R^{63})$, —$C(O)R^{42}$, —$C(O)N(R^{42})(R^{43})$, —$C(S)N(R^{42})(R^{43})$, —$C(S)OR^{42}$ and —$C(O)OR^{42}$.

In some embodiments $R^{42}$ and $R^{43}$ are each independently selected from the group consisting of hydrogen $(C_1-C_6)$alkyl, $(C_1-C_6)$heteroalkyl, $(C_1-C_6)$haloalkyl; $(C_2-C_6)$alkenyl, $(C_2-C_6)$alkynyl, $(C_3-C_8)$cycloalkyl $(C_6-C_{10})$aryl, $(C_6-C_{10})$aryl$(C_1-C_6)$alkyl, $(C_3-C_{10})$heteroaryl, $(C_3-C_{10})$heteroaryl$(C_1-C_6)$alkyl, preferably selected from the group consisting of hydrogen $(C_1-C_6)$alkyl, $(C_1-C_6)$heteroalkyl, $(C_1-C_6)$haloalkyl; $(C_3-C_8)$cycloalkyl $(C_6-C_{10})$aryl, $(C_6-C_{10})$aryl$(C_1-C_6)$alkyl, $(C_3-C_{10})$heteroaryl, $(C_3-C_{10})$heteroaryl $(C_1-C_6)$alkyl.

In some embodiments $R^{51}$ is selected from the group consisting of hydrogen, substituted or unsubstituted $(C_1-C_6)$alkyl, $(C_1-C_6)$heteroalkyl, $(C_1-C_6)$haloalkyl; substituted or unsubstituted $(C_2-C_6)$alkenyl, substituted or unsubstituted $(C_2-C_6)$alkynyl, substituted or unsubstituted $(C_3-C_8)$cycloalkyl, substituted or unsubstituted $(C_6-C_{10})$aryl, substituted or unsubstituted $(C_6-C_{10})$aryl$(C_1-C_6)$alkyl, substituted or unsubstituted $(C_3-C_{10})$heteroaryl, substituted or unsubstituted $(C_3-C_{10})$heteroaryl$(C_1-C_6)$alkyl, halogen, —CN, —$NO_2$, —$OR^{61}$, —$N(R^{62})(R^{63})$, —$N(R^{61})(O)$, —$S(O)_{0-2}R^{61}$, —$S(O)_{1-2}OR^{61}$, —$OS(O)_{1-2}R^{61}$, —$OS(O)_{1-2}OR^{61}$, —$S(O)_{1-2}N(R^{62})(R^{63})$, —$OS(O)_{1-2}N(R^{62})(R^{63})$, —$N(R^{61})S(O)_{12}R^{61}$, —$NR^{61}S(O)_{1-2}OR^{61}$, —$NR^{61}S(O)_{1-2}N(R^{62})(R^{63})$, —$C(=W)R^{61}$, —$C(=W)WR^{61}$, —$WC(=W)R^{61}$, and —$WC(=W)WR^{61}$. In other embodiments $R^{51}$ is selected from the group consisting of hydrogen, $(C_1-C_6)$alkyl, $(C_1-C_6)$heteroalkyl, $(C_1-C_6)$haloalkyl; $(C_2-C_6)$alkenyl, $(C_2-C_6)$alkynyl, $(C_3-C_6)$cycloalkyl, $(C_6-C_{10})$aryl, $(C_6-C_{10})$aryl$(C_1-C_6)$alkyl, $(C_3-C_{10})$heteroaryl, $(C_3-C_{10})$heteroaryl$(C_1-C_6)$alkyl, halogen, —CN, —$NO_2$, —$OR^{61}$, —$N(R^{62})(R^{63})$, —$N(R^{61})(OR^{61})$, —$S(O)_{0-2}R^{61}$, —$S(O)_{1-2}OR^{61}$, —$OS(O)_{1-2}R^{61}$, —$OS(O)_{1-2}OR^{61}$, —$S(O)_{1-2}N(R^{62})(R^{63})$, —$OS(O)_{1-2}N(R^{62})(R^{63})$, —$N(R^{61})S(O)_{12}R^{61}$, —$NR^{61}S(O)_{1-2}OR^{61}$, —$NR^{61}S(O)_{1-2}N(R^{62})(R^{63})$, —$C(=W)R^{61}$, —$C(=W)WR^{61}$, —$WC(=W)R^{61}$, and —$WC(=W)WR^{61}$.

In some embodiments $R^{61}$ is, in each case, selected from the group consisting of —H, alkyl, alkenyl, alkynyl, cycloalkyl, aryl, heteroaryl, and heterocyclyl, preferably hydrogen and $(C_1-C_6)$alkyl.

In some embodiments $R^{62}$ and $R^{63}$ are, in each case, independently selected from the group consisting of —H, alkyl, alkenyl, alkynyl, cycloalkyl, aryl, heteroaryl, and heterocyclyl.

In some embodiments W is independently selected from O, S, and $N(R^{64})$, in other embodiments W is O; in other embodiments W is S, in other embodiments W is $N(R^{64})$.

In some embodiments $R^{64}$ is independently selected from the group consisting of —H, alkyl, alkenyl, alkynyl, cycloalkyl, aryl, heteroaryl, heterocyclyl, and —$OR^{61}$, in other embodiments $R^{64}$ is independently selected from the group consisting of —H, alkyl, cycloalkyl, aryl, heteroaryl, heterocyclyl, and —$OR^{61}$.

In some embodiments X is O, in other embodiments X is S.

In some embodiments the compound for use and the compound of the pharmaceutical composition for use having a structure according to Formula I, Formula IA and/or Formula IB, as disclosed herein, are useful for the treatment of a bacterial disease, wherein the bacterial disease is caused by at least one bacteria which belong to the groups of Firmicutes and Actinobacteria. In other embodiments bacterial disease is caused by at least one bacteria selected from the group comprising *Listeria monocytogenes*, *Listeria welshimeri*, *Staphylococcus aureus*, MRSA and clinical isolates thereof; Vancomycin-intermediate *Staphylococcus aureus*, Vancomycin-resistant *Staphylococcus aureus*, *Staphylococcus haemolyticus*, *Staphylococcus hominis*, *Staphylococcus epidermidis*, *Staphylococcus saprophyticus*, *Staphylococcus lugdunensis*, *Staphylococcus schleiferi*, *Staphylococcus caprae*, *Streptococcus pneumoniae*, *Streptococcus viridans*, *Streptococcus pyogenes*, *Streptococcus agalactiae*, *Enterococcus faecalis*, *Enterococcus faecium*, *Bacillus licheniformis*, *Bacillus subtilis*, *Bacillus anthracis*, *Bacillus cereus*, *Bacillus thuringiensis*, *Bacillus larvae*, *Mycobacterium tuberculosis*, *Mycobacterium bovis*, *Mycobacterium leprae*, *Mycobacterium ulcerans*, *Mycobacterium kanasasii*, *Mycobacterium avium*, *Mycobacterium paratuberculosis*, *Mycobacterium scrofulaceam*, *Mycobacterium microti*, *Mycobacterium africanurn*, *Mycobacterium canettii*, *Mycobacterium intracellulare*, *Mycobacterium simiae*, *Mycobacterium szulgai*, *Mycobacterium xenopi*, *Mycobacterium fortuitum*, *Mycobacterium chelonei*, *Mycobacterium marinum*, *Nocardia asteroids*, *Rhodococcus equi* and *Burkholderia thailandensis*. In other embodiments bacterial disease is caused by at least one bacteria selected from the group consisting of *Listeria monocytogenes*, *Listeria welshimeri*, *Staphylococcus aureus*, MRSA and clinical isolates thereof; Vancomycin-intermediate *Staphylococcus aureus*, Vancomycin-resistant *Staphylococcus aureus*, *Staphylococcus haemolyticus*, *Staphylococcus hominis*, *Staphylococcus epidermidis*, *Staphylococcus saprophyticus*, *Staphylococcus lugdunensis*, *Staphylococcus schleiferi*, *Staphylococcus caprae*, *Streptococcus pneumoniae*, *Streptococcus viridans*, *Streptococcus pyogenes*, *Streptococcus agalactiae*, *Enterococcus faecalis*, *Enterococcus faecium*, *Bacillus licheniformis*, *Bacillus subtilis*, *Bacillus anthracis*, *Bacillus cereus*, *Bacillus thuringiensis*, *Bacillus larvae*, *Mycobacterium tuberculosis*, *Mycobacterium bovis*, *Mycobacterium leprae*, *Mycobacterium ulcerans*, *Mycobacterium kanasasii*, *Mycobacterium avium*, *Mycobacterium paratuberculosis*, *Mycobacterium scrofulaceam*, *Mycobacterium microti*, *Mycobacterium africanum*, *Mycobacterium canettii*, *Mycobacterium intracellulare*, *Mycobacterium simiae*, *Mycobacterium szulgai*, *Mycobacterium xenopi*, *Mycobacterium fortuitum*, *Mycobacterium chelonei*, *Mycobacterium marinurn*, *Nocardia asteroids*, *Rhodococcus equi* and *Burkholderia thailandensis*. In other embodiments bacterial disease is caused by at least one bacteria selected from the group consisting of *Staphylococcus aureus*, MRSA and clinical isolates thereof; Vancomycin-intermediate *Staphylococcus aureus*, Vancomycin-resistant *Staphylococcus aureus*, and *Staphylococcus epidermidis*. In other embodiments the bacterial disease is caused by at least one bacteria selected from the group consisting of *Staphylococcus aureus*, MRSA and clinical isolates thereof, *Clostridium difficile*, *Streptococcus pneumonia*, *Streptococcus pyogenes*, *Streptococcus pneumonia*, *Staphylococcus epidermidis*, *Staphylococcus haemolyticus*, *Staphylococcus hominis*, Vancomycin-intermediate *S. aureus*, Vancomycin-resistant *S. aureus*, *Listeria monocytogenes*, *Mycobacterium tuberculosis* and *Burkholderia thailandensis*. In other embodiments the bacterial disease is caused by gram positive bacteria, preferably by *Staphylococcus* strains, more preferably by *Staphylococcus aureus* strains, even more preferably by MRSA and clinical isolates thereof; Vancomycin-intermediate *Staphylococcus aureus* and Vancomycin-resistant *Staphylococcus aureus*, still more preferably by MRSA and clinical isolates thereof.

Another aspect of the present invention relates to a compound having a structure according to Formula II

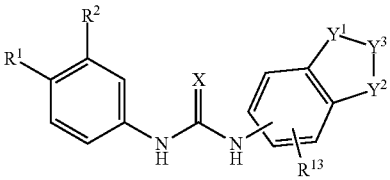

(II)

wherein
$R^1$ is cyano or halogen, preferably halogen, more preferably chlorine;
$R^2$ is $(C_1-C_6)$alkyl or $(C_1-C_6)$haloalkyl, preferably $(C_1-C_6)$haloalkyl, more preferably —$CF_3$;
$Y^1$ and $Y^2$ are each independently selected from the group consisting of O, S, SO and $SO_2$, preferably O or S, more preferably O;
$Y^3$ is $CR^{11}R^{12}$;
$R^{11}$ and $R^{12}$ are each independently selected from the group consisting of hydrogen and halogen, preferably halogen, more preferably fluorine;
$R^{13}$ is selected from the group consisting of hydrogen, $(C_1-C_6)$alkyl, $(C_1-C_6)$haloalkyl and halogen, preferably hydrogen;
X is O or S, preferably O;
or a pharmaceutically acceptable salt, solvate or hydrate thereof.

In some embodiments the compound having a structure according to Formula II, as disclosed herein, is a compound selected from the group consisting of 1-(4-chloro-3-methylphenyl)-3-(2,2-difluorobenzo[d][1,3]dioxol-5-yl)urea, 1-(4-chloro-3-(trifluoromethyl)phenyl)-3-(2,2-difluorobenzo[d][1,3]dioxol-5-yl)urea, 1-(4-chloro-3-(trifluoromethyl)phenyl)-3-(2,2-difluorobenzo[d][1,3]dioxol-5-yl)thiourea, 1-(benzo[d][1,3]dioxol-5-yl)-3-(4-chloro-3-(trifluoromethyl)phenyl)urea, and 1-(4-chloro-3-(trifluoromethyl)phenyl)-3-(2,2-difluorobenzo[d][1,3]dioxol-4-yl)urea.

In other embodiments compound having a structure according to Formula II is 1-(4-chloro-3-methylphenyl)-3-(2,2-difluorobenzo[d][1,3]dioxol-5-yl)urea. In other embodiments compound having a structure according to Formula II is 1-(4-chloro-3-(trifluoromethyl)phenyl)-3-(2,2-difluorobenzo[d][1,3]dioxol-5-yl)urea. In other embodiments compound having a structure according to Formula II is 1-(4-chloro-3-(trifluoromethyl)phenyl)-3-(2,2-difluorobenzo[d][1,3]dioxol-5-yl)thiourea. In other embodiments compound having a structure according to Formula II is 1-(benzo[d][1,3]dioxol-5-yl)-3-(4-chloro-3-(trifluoromethyl)phenyl)urea. In other embodiments compound having a structure according to Formula II is 1-(4-chloro-3-(trifluoromethyl)phenyl)-3-(2,2-difluorobenzo[d][1,3]dioxol-4-yl)urea.

In some embodiments the compound having a structure according to Formula II, as disclosed herein, is for use in medicine.

In some embodiments the compound having a structure according to Formula II, as disclosed herein, is useful for the treatment of a bacterial disease. The bacterial disease is preferably caused by at least one bacteria selected from the list consisting of *Listeria monocytogenes, Listeria welshimeri, Staphylococcus aureus*, MRSA and clinical isolates thereof; Vancomycin-intermediate *Staphylococcus aureus*, Vancomycin-resistant *Staphylococcus aureus, Staphylococcus haemolyticus, Staphylococcus hominis, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracis, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroids, Rhodococcus equi* and *Burkholderia thailandensis*, preferably wherein the bacterial disease is caused by gram positive bacteria. The bacterial disease is caused preferably by gram positive bacteria, more preferably by a methicillin-resistant *Staphylococcus aureus* strain (MRSA).

Another aspect of the present invention is a kit comprising a compound having a structure according to Formula II, as disclosed herein, and at least one pharmaceutically acceptable carrier.

As used herein and throughout the entire description, the terms "carrier" and "excipient" are used interchangeably herein. Pharmaceutically acceptable carriers or excipients include diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), anti-foaming agents (e.g. Simethicone), thickening agents (e.g. methylcellulose or hydroxyethylcellulose), sweetening agents (e.g. sorbitol, saccharin, aspartame, acesulfame), flavoring agents (e.g. peppermint, lemon oils, butterscotch, etc), humectants (e.g. propylene, glycol, glycerol, sorbitol). The person skilled in the art will readily be able to choose suitable pharmaceutically acceptable carriers or excipients, depending, e.g., on the formulation and administration route of the pharmaceutical composition.

A non-exhaustive list of exemplary pharmaceutically acceptable carriers or excipients includes (biodegradable) liposomes; microspheres made of the biodegradable polymer poly(D,L)-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable excipients are inter alia described in Remington's Pharmaceutical Sciences, $15^{th}$ Ed., Mack Publishing Co., New Jersey (1991) and Bauer et al., Pharmazeutische Technologie, $5^{th}$ Ed., Govi-Verlag Frankfurt (1997).

The present invention also relates to wound dressings, medical devices, implants etc. which are amenable to coatings comprising at least one compound and/or composition of the invention. The wound dressing, devices or implants etc. may have surfaces composed of thermoplastic or polymeric materials such as polyethylene, Dacron, nylon, polyesters, polytetrafluoroethylene, polyurethane, latex, silicone elastomers and the like. Devices and/or implants with metallic surfaces are also amenable to coatings with the compounds/compositions of the present invention. Such devices or implants, for example bone and joint prosthesis, can be coated by cement mixture containing the compounds/compositions of the invention. Particular devices especially suited for application of the compounds/compositions of this invention include but are not limited to intravascular, peritoneal, pleural and urological catheters, heart valves; cardiac pacemakers; vascular shunts; and orthopedic, intraocular, or penile prosthesis.

In some embodiments the compound for use and the compound of the pharmaceutical composition for use disclosed herein and in particular those compounds having a structure according to Formula I, Formula IA, Formula IB and/or Formula II, as disclosed herein, are characterized in that such compound binds to Signal peptidase IB enzyme (SpsB), preferably such compound activates the Signal peptidase IB enzyme, preferably such compound leads to an activation of the Signal peptidase as shown by FRET (Förster resonance energy transfer)-based peptidase assay (Rao S. C. V.; Bockstael, K.; Nath, S.; Engelborghs, Y.; Anné, J; Geukens, N. *FEBS* 2009, 276 (12), 3222-3234) using the SpsB-containing membrane fraction of *S. aureus* (Therien A. G. et al, *Antimicrob Agents Ch* 2012, 194 (10), 2677 2686.) (FIG. 7A-C). The substrate for cleavage with SpsB is an internally quenched peptide from *Staphylococcus epidermidis* SceD preprotein with Dabcyl- and Edans groups as FRET pair (4-(4-dimethylaminophenylazo)benzoic acid; EDANS: 5-((2-aminoethyl)amino)-1-naphthalenesulfonic acid). Membrane bound SpsB cleaves the peptide releasing the fluorescent donor from quenching which results in fluorescence detectable at 510 nm. Upon treatment with 100 μM sorafenib and 100 μM PK/X17-1-150 activity of SpsB increased to 2.6 and 4.3 A·U/s, respectively, compared to DMSO treated control (1.8 A·U/s).

The above assay is disclosed herein in the appended examples and also exemplified in the following. Cells were grown according to stationary phase, harvested (12.000×g, 10 min, 4° C.), digested with lysostaphin (end conc: 20 U/mL, 37° C., 1 h) and sonicated (30 s, 20%, Bandelin Sonoplus, Berlin, Germany). Intact cells and debris were removed by centrifugation: 12.000×g, 10 min, 4° and membranes collected: 39.000×g, 75 min, 4° C. Membranes were resuspended in 2 mL cold 50 mM sodium phosphate buffer pH 7.5 and protein concentration determined by BCA (Roti®-Quant universal, Carl Roth GmbH+Co. KG, Karlsruhe, Germany) assay.

0.1 mg/mL membranes in 50 mM sodium phosphate buffer pH 7.5 were used for the FRET (Förster resonance energy transfer) assay and incubated with 1 µL compound (in DMSO) and 10 µM SPase I FRET substrate (Sequence of SceD peptide): DABCYL-AGHDAHASET-EDANS (Protein AGHDAHASET has SEQ ID NO. 1, DABCYL: 4-(4-dimethylaminophenylazo)benzoic acid; EDANS: 5-((2-aminoethyl)amino)-1-naphthalenesulfonic acid, Anaspec Inc., Fremont, CA, USA). Fluorescence turnover was determined on a TECAN plate reader (Tecan infinite 200Pro, Tecan Group Ltd., Zurich, Switzerland) at 37° C. using 340 nm as excitation and 510 nm as emission wavelengths in fluorescence top reading mode.

Addition of sorafenib and PK/X17-1-150 increased SpsB peptidase activity (FIG. 7A-C) demonstrating that binding to the enzyme stimulates substrate turnover.

The present invention further relates to the compounds of the invention and in particular the compounds for use and compounds of the pharmaceutical composition for use having a structure according to Formula I, Formula IA, Formula IB and/or Formula II, as disclosed herein, that are characterized in that said compounds increase the bacterial SpsB activity. Assays that are able to detect such an increase are exemplified hereinabove and in the appended examples. Said SpsB activity is a proteolytic activity. Preferably, said compounds increase the bacterial SpsB activity by binding to SpsB. In this regard it is envisaged that said compounds bind reversibly to SpsB. However, also irreversible binding is envisaged. It is equally preferred that said compounds increase the bacterial SpsB activity by stimulating a substance leading to an increased SpsB activity. Said substance can directly or indirectly stimulate SpsB. In this regard a direct stimulation is understood as a direct binding of said substance to SpsB, thereby increasing the bacterial SpsB activity. Indirect stimulation means that a substance activates SpsB via another substance or via a signal cascade increasing the bacterial SpsB activity. It is further envisaged that the compounds described herein lead to an enrichment of secretion proteins in the bacterial cell by SpsB-catalyzed proteolysis of cellular proteins. Preferably, said cellular proteins are essential cellular proteins. More preferably, said cellular proteins are the essential cellular proteins penicillin binding protein 1 (PBP1) and penicillin binding protein 2 (PBP2). The SpsB-catalyzed proteolysis leads to the cleavage of said cellular proteins. Preferably said cleavage is an unspecific cleavage of cellular proteins. Accordingly, the compounds of the present application cause an increased activity of SpsB in bacterial cells, leading to the cleavage of cellular proteins and resulting in an increase secretion and accumulation of secretory proteins, wherein said accumulation leads to cell death of bacterial cells.

The term "increasing" or "increased" when used herein refers to an enhanced SpsB activity when contacting bacteria with one or more compounds of the present application. The SpsB activity is thereby measured as compared to a reference, i.e. the bacterial SpsB activity in bacteria which have not been contacted with one or more compounds of the present invention. Alternatively, the SpsB activity can be measured as compared to the bacterial SpsB activity in bacteria contacted with sorafenib.

The stimulatory properties of a compound for increasing SpsB activity in bacteria can be determined using diverse assays or tests for measuring the activity and cleavage capability of SpsB in vitro. According to the present invention, an optical assay can be applied to identify substances with the desired properties. Preferably, an optical assay applicable in this regard is a fluorescence resonance energy transfer (FRET) membrane assay measuring the cleavage of fluorogenic SpsB substrates (see FIG. 7). The SpsB substrate preferably consists of a SpsB target peptide sequence, i.e. a fluorogenic SpsB substrate, comprising a fluorescence donor and a fluorescence quencher. Preferably the fluorescence donor is EDANS and the fluorescence quencher is DABCYL, but also other fluorescence donors and quenchers can be used. In this regard the compounds of the present invention reveal an elevated turnover of the fluorogenic substrate, thereby demonstrating an enhanced proteolytic activity of bacterial SpsB when contacting SpsB with any the SpsB target protein, which results in an increased fluorescence signal (see FIG. 7). The fluorescence signal is thereby measured as compared to a reference, i.e. the fluorescence signal emitted by the proteolysis of the fluorogenic SpsB substrate by SpsB without contacting SpsB with any of the compounds of the present invention. Alternatively the fluorescence signal emitted by the proteolysis of the fluorogenic SpsB substrate when contacting SpsB with sorafenib can also be used as reference. Accordingly, increased fluorescence intensity as compared to a reference is indicative for the stimulatory properties of a compound for increasing SpsB activity and its high antibacterial activity.

Thus, the present invention also relates to a method of determining or identifying a compound for increasing the bacterial SpsB activity, comprising combining bacterial SpsB with said compound and a fluorogenic SpsB substrate, thereby measuring the fluorescence signal as compared to a reference, wherein an increased fluorescence intensity indicates that said compound is suitable for increasing the bacterial SpsB activity. Moreover, the present invention relates to a method of evaluating the capability of a compound for increasing the bacterial SpsB activity, comprising combining bacterial SpsB with said compound and a fluorogenic SpsB target peptide, thereby measuring the fluorescence signal as compared to a reference, wherein an increased fluorescence intensity is indicative for the capability of said compound in increasing the bacterial SpsB activity. Preferably the fluorescence is measured using a fluorescence resonance energy transfer (FRET) membrane optical assay.

Alternatively, the antibacterial activity of the compounds of the present invention can be determined by proteomic analysis of proteins secreted by said bacteria when contacted with any of the compounds of the present invention as compared to a reference. The reference is the proteomic analysis of proteins secreted by bacteria not contacted with any of the compounds of the present invention. Alternatively, the proteomic analysis of proteins secreted by bacteria contacted with sorafenib can also be used as reference. Such a proteomic assay or test can thus be equally used determining or identifying a compound for increasing the bacterial SpsB activity and for measuring activity and cleavage capability of bacterial SpsB. Preferably, said proteomic assay comprises massspectrometric analysis for determining the proteins secreted by said bacterial cells when contacted with said compounds (see FIG. 8, 9).

Thus, the present invention also relates to a method of determining or identifying a compound for increasing the bacterial SpsB activity, comprising contacting bacteria with said compound and conducting a proteomic analysis of the proteins secreted by said bacteria, wherein an increase of secreted proteins is indicative for the suitability of said compound for increasing the bacterial SpsB activity. Moreover, the present invention relates to a method of evaluating the capability of a compound for increasing the bacterial SpsB activity, comprising contacting bacteria with said compound and conducting a proteomic analysis of the proteins secreted by said bacteria, wherein an increase of secreted proteins is indicative for the capability of said compound in increasing the bacterial SpsB activity. Preferably the proteomic analysis is conducted by mass spectrometry. The present invention also refers to a method of increasing SpsB activity in bacteria, comprising contacting said bacteria with any of the compound of the present invention.

The diaryl ureas of the present invention having a structure according to Formula I, Formula IA, Formula IB or Formula II may be prepared by the use of known chemical reactions and procedures, some from starting materials which are commercially available. Nevertheless, general preparative methods are provided below to aid one skilled in the art in synthesizing these compounds, with more detailed examples being provided in the Experimental section which follows.

Substituted anilines may be generated using standard methods (March. *Advanced Organic Chemistry*, 3rd Ed.; John Wiley: New York (1985). Larock. *Comprehensive Organic Transformations*; VCH Publishers: New York (1989)). As shown in Scheme I, aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino-and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3rd Ed.; John Wiley: New York (1985). Larock. *Comprehensive Organic Transformations*; VCH Publishers: New York (1989)).

Scheme I: Reduction of Nitroaryls to Aryl Amines

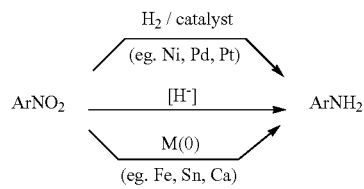

Nitroaryls are commonly formed by electrophilic aromatic nitration using HNO3, or an alternative NO2+ source. Nitroaryls may be further elaborated prior to reduction.

Thus, nitroaryls substituted with potential leaving groups (e.g. F, Cl, Br, etc.) may undergo substitution reactions on treatment with nucleophiles, such as thiolate (exemplified in Scheme II) or phenoxide. Nitroaryls may also undergo Ullman-type coupling reactions (Scheme II).

Scheme II: Selected Nucleophilic Aromatic Substitution using Nitroaryls

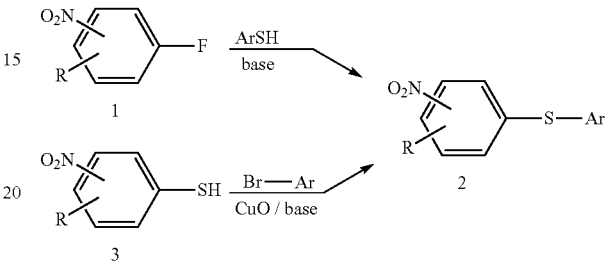

Nitroaryls may also undergo transition metal mediated cross coupling reactions. For example, nitroaryl electrophiles, such as nitroaryl bromides, iodides or triflates, undergo palladium mediated cross coupling reactions with aryl nucleophiles, such as arylboronic acids (Suzuki reactions, exemplified below), aryltins (Stille reactions) or arylzincs (Negishi reaction) to afford the biaryl (5).

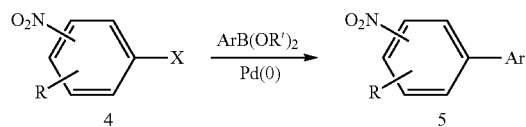

As shown in Scheme III, non-symmetrical urea formation may involve reaction of an aryl isocyanate (14) with an aryl amine (13). The compounds according to formula 1B can be prepared in an analogous manner by reacting an aryl isocyanate with an amine.

In general, the reaction of the aryl isocyanate with the amine or aryl amine is carried out preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitriles such as acetonitrile; heteroaromatics such as pyridine; polar solvents such as dimethyl formamide and hexamethyl phosphoric acid tris-amide; and mixtures of the above-mentioned solvents. Toluene, benzene, and dichloromethane are preferred.

The amine or aryl amine is generally employed in an amount of from 1 to 3 mol per mol of aryl isocyanate; an equimolar amount or slight excess of amine or aryl amine is preferred.

The reaction of the aryl isocyanate with the amine or aryl amine is generally carried out within a relatively wide temperature range. In general, they are carried out in a range of from −20 to 200 C, preferably from 0 to 100 C, and more preferably from 25 to 50 C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

The heteroaryl isocyanate may be synthesized from a heteroaryl amine by treatment with phosgene or a phosgene equivalent, such as trichloromethyl chloroformate (diphosgene), bis (trichloromethyl) carbonate (triphosgene), or N, N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate.

The corresponding carboxylic acid (17) may also be subjected to Curtius-type rearrangements using diphenylphosphoryl azide (DPPA) or a similar reagent.

Scheme III: Selected Methods of Non-Symmetrical Urea Formation

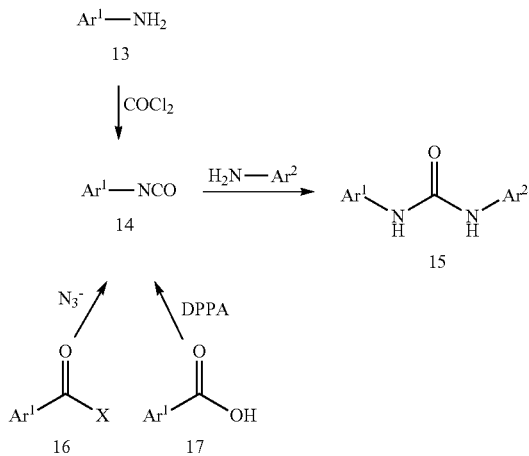

Finally, ureas may be further manipulated using methods familiar to those skilled in the art.

The pharmaceutical composition of the invention will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed in accordance with the invention for delivery by any suitable route of administration. In the context of the present invention, the routes of administration include topical routes (such as epicutaneous, inhalational, nasal, opthalmic, auricular/aural, vaginal, mucosal);

enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

In some embodiments the administration may be a parenteral route, in particular intravenous or intramuscular. In some embodiments the administration may be an enteral route, in particular oral.

In some embodiments, the pharmaceutical composition, as disclosed herein, is administered to a subject in need thereof in an amount effective to treat said bacterial disease. The subject is preferably a mammal. The subject is more preferably a human subject. The bacterial disease can be any bacterial disease disclosed herein above and below.

As used herein and throughout the entire description, the term "Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like. The subject is preferably a mammal, more preferably a human.

As used herein and throughout the entire description, the term "amount effective" in the context of a composition or dosage form for administration to a subject refers to an amount of the composition or dosage form sufficient to provide a benefit in the treatment of bacterial disease, to delay or minimize symptoms associated with bacterial infection or bacterial-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

Another aspect of the present invention is the use of a compound having a structure according to Formula II as a disinfectant.

The present invention also envisions a method of treating in a subject a bacterial infection, comprising administering to said subject an efficient amount of a compound according to Formula (I), Formula (IA), Formula (IB) and/or Formula (II) or a pharmaceutically acceptable salt, solvate or hydrate thereof or a pharmaceutical composition comprising said compound. Said method preferably comprises further administering at least one additional pharmaceutically active compound, including an antibiotic or antifungal. The above described aspects, embodiments, definitions, etc. are also applicable to said method of treatment, mutatis mutandis.

Figure 1:
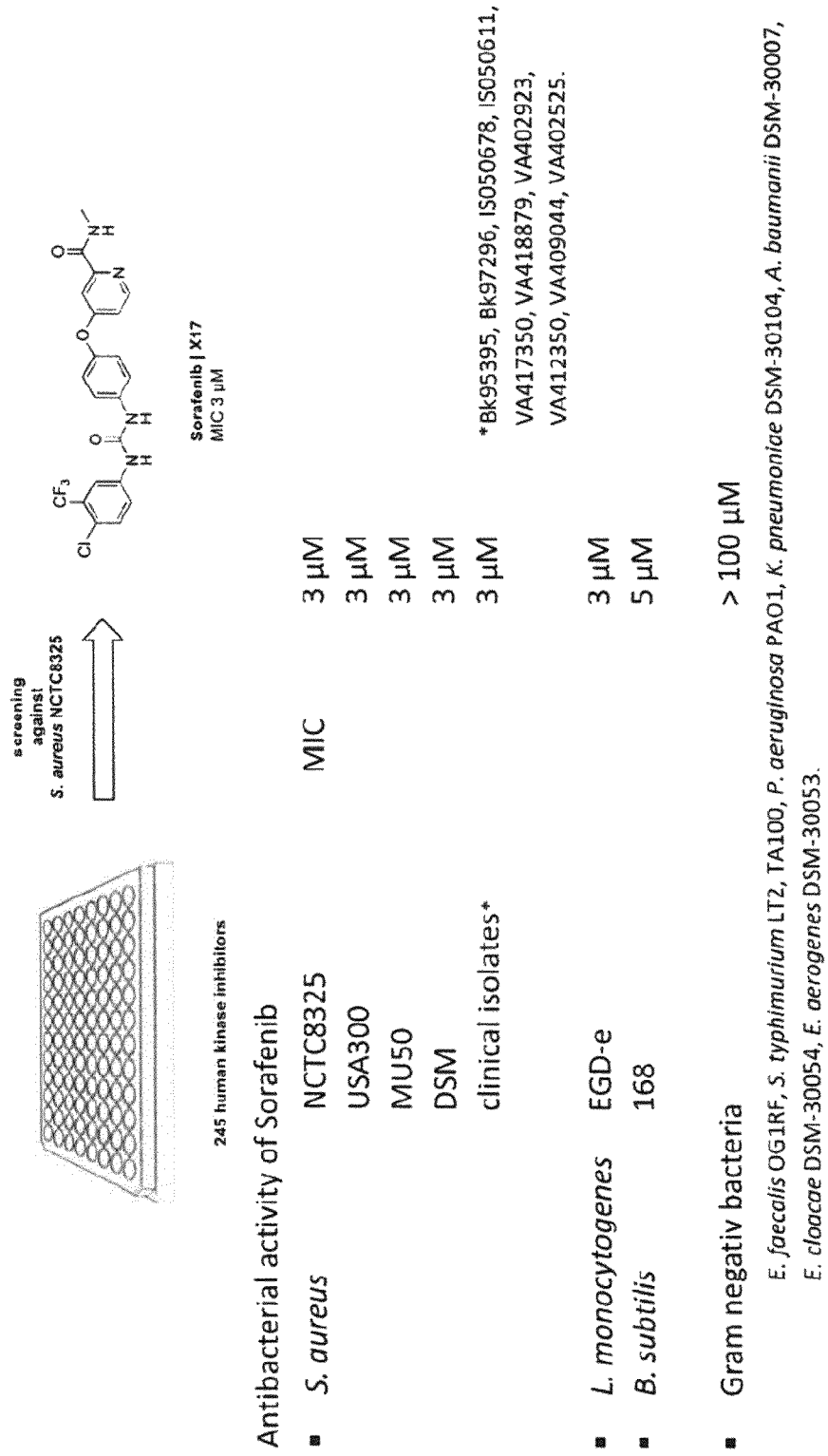
FIG. 1: Antibacterial activity of kinase inhibitor sorafenib (Bay 43-9006, Nexavar™ against various gram positive and gram negative bacteria and bacterial strains. No growth of bacteria could be observed by eye at the minimum inhibitory concentration (MIC) of the probe.
Figure 2:
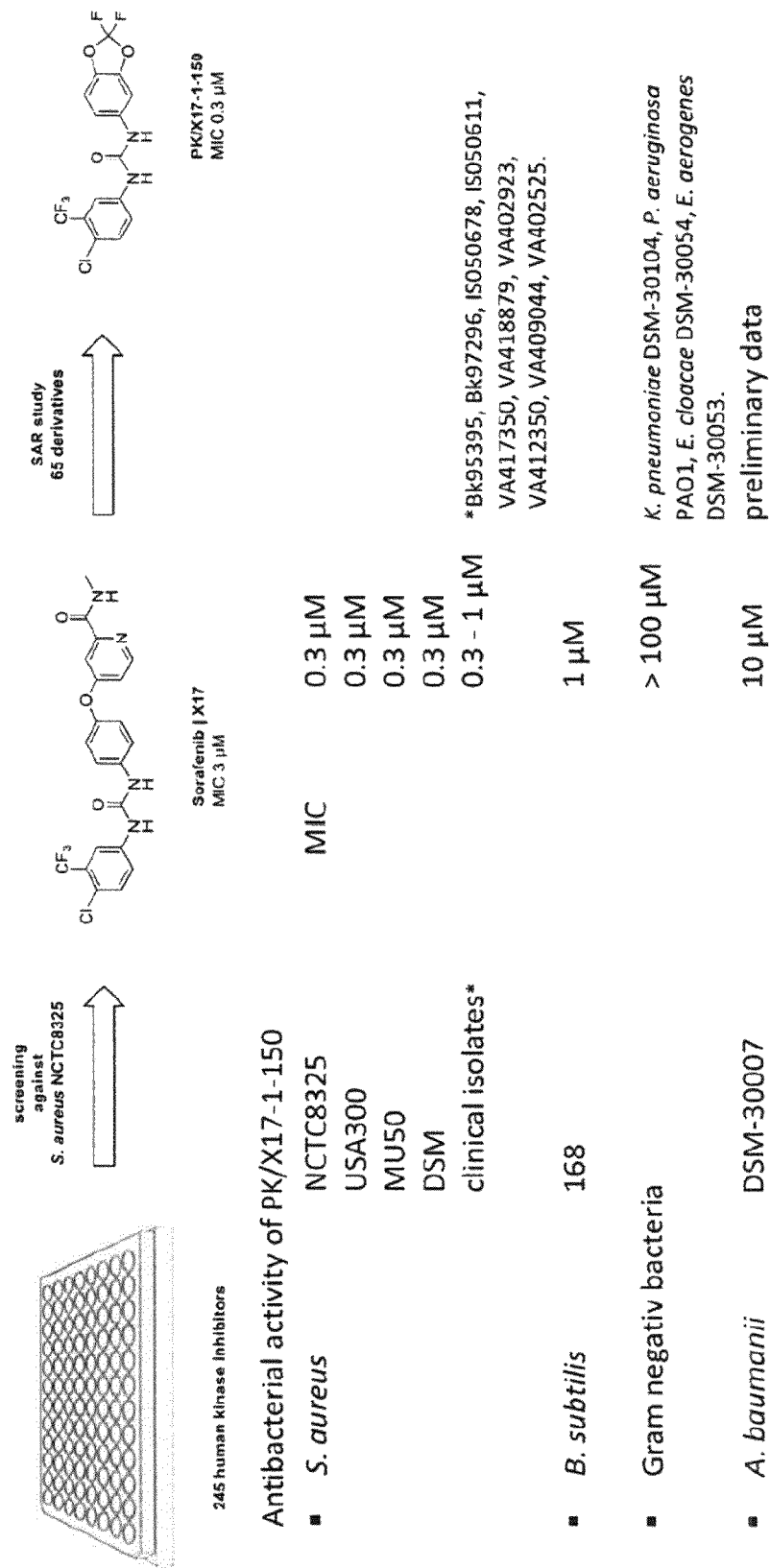
FIG. 2: Antibacterial activity of PK/X17-1-150 against various gram positive and gram negative bacteria and bacterial strains. No growth of bacteria could be observed by eye at the minimum inhibitory concentration (MIC) of the probe.

A) Results of a persister cell assay I. Persister cells were selected from overnight cultures of *S. aureus* NCTC8325 using 20 µg/mL gentamicin for 4 h, washed, diluted to $OD_{600}$=0.4 in PBS and incubated with 2.4 µM PK/X17-1-150, 24 µM sorafenib or 5 µg/mL ciprofloxacin as negative control. Samples were taken at several time-points, cells were serially diluted and plated for the determination of CFU/mL. After 70 h a significant reduction of viable cells for PK/X17-1-150 and sorafenib treated cells compared to the DMSO control is observed, whereas there is no change for the ciprofloxacin-treated control.

B) Results of a persister cell assay II. *S. aureus* NCTC8325 cells were grown to $OD_{600}$=4 (A) or overnight (B) and incubated with 30 µg/mL oxacillin for persister selection in combination with 2.4 µM PK/X17-1-150 or PK/X17-4-011 (inactive control), 24 µM sorafenib or PK/X17-2-011 (inactive control) or 5 µg/mL ciprofloxacin as negative control in TSB-medium. Additionally, compounds were tested without oxacillin to exclude combinatory effects, as the majority of the cells at $OD_{600}$=4 and from overnight cultures already are persisters and do not require selection by oxacillin. After 20 h (A) or 70 h (B) of treatment, cells were serially diluted and plated for the determination of CFU/mL. In all cases there is a significant reduction of viable cells for PK/X17-1-150 and Sorafenib treated cells compared to the DMSO control, whereas there is no change observed for ciprofloxacin-, PK/X17-4-011- or PK/X17-2-011-treated controls.

FIG. 13:

Location of probe PK/X17-1-150 (spheres) within the signal peptidase (surface). a) Surface representation with PK/X17-1-150 shown as spheres, carbon, oxygen, nitrogen, chloride, fluorine atoms are colored purple, red, blue, green, cyan, respectively. b) Detailed representation of the binding site showing PK/X17-1-150 (purple), important active site residues (blue) and residues bound to the probe (gray) in stick representation within the signal peptidase (cartoon). The distances shown correspond to the average values over the last 150 ns of simulation (A).

Further, the invention shall be explained in more detail by the following Examples.

1) Materials and Methods 1.1) Reagents

Reagents and solvents were purchased from commercial suppliers (Sigma-Aldrich Co. LLC, Thermo Fisher Scientific Inc., Merck KGaA, TCI Europe GmbH, Fluorochem Ltd. and Alfa Aesar GmbH) and used without further purification, unless otherwise indicated. HPLC-grade solvents or anhydrous solvents (max. 0.01% water content, stored over molecular sieve under an argon atmosphere) were used for all reactions. All experiments were monitored by analytical thin layer chromatography (TLC). TLC was performed on precoated silica gel plates (60 F-254, 0.25 mm, Merck KGaA) with detection by UV ($\lambda$=254 and/or 366 nm) and/or by coloration using a phosphomolybdate (PMA), and/or potassium permanganate (KMnO4) stain and subsequent heat treatment. Flash chromatography was performed on silica gel 60 (0.035-0.070 mm, mesh 60 Å, Merck KGaA) with the indicated eluent. Preparative thin layer chromatography (prep TLC) was performed on pre-coated silica layer plates (SIL G-100 UV254, 1.00 mm, Macherey-Nagel GmbH & Co. KG) with the indicated eluent. Common solvents for chromatography [n-hexane (Hex), ethyl acetate (EtOAc), dichloromethane ($CH_2Cl_2$) and methanol (MeOH)] were distilled prior to use.

1.2) NMR $^1$H and proton-decoupled $^{13}$C NMR spectra were recorded on a Bruker Avance III HD 300 (300 MHz), a Bruker Avance I 360 (360 MHz), a Bruker Avance III HD (500 MHz) or a Bruker Avance III HD (500 MHz, equipped with a Bruker CryoProbe platform) at 298 K. Chemical shifts are reported in delta ($\delta$) units in parts per million (ppm) relative to distinguished solvent signals [deuterated chloroform ($CDCl_3$) $\delta_H$=7.26 ppm and $\delta_C$=77.16 ppm; deuterated DMSO (DMSO-$d_6$), $\delta_H$=2.50 ppm]. The following abbreviations were used for the assignment of the signals: s—singlet, d—doublet, t—triplet, q—quartet, m—multiplet. Coupling constants J are given in Hertz [Hz]. HR-MS spectra were recorded in the ESI or APCI mode on a Thermo Scientific LTQ-FT Ultra (FT-ICR-MS) coupled with an UltiMate 3000 HPLC system (Thermo Fisher Scientific Inc.).

1.3) Cell Culture

Cell culture media and supplements were obtained from Sigma Life Science and Life Technologies. A549 and Hela cells were cultured in Dulbecco's Modified Eagle Medium (DMEM high glucose, 4.5 g/L) supplemented with 10% fetal bovine serum (Sigma Life Science) and 2 mM L-glutamine (PAA). NIH/3T3 cells were cultured in Dulbecco's Modified Eagle Medium (DMEM high glucose) supplemented with 10% fetal bovine serum (Sigma Life Science) and 4 mM L-glutamine (PAA). HepG2 cells were cultured in RPMI-1640 medium supplemented with 10% fetal bovine serum (Sigma Life Science) and 2 mM L-glutamine (PAA). All cells were maintained in a humidified 37° C. incubator with 5% $CO_2$. Cells were detached with trypsin-EDTA.

1.4) Bacterial Strains and Media

Commercially available strains were obtained from the following suppliers: Institute Pasteur, France (*Staphylococcus aureus* NCTC 8325, *S. aureus* Mu 50, *Listeria monocytogenes* EGD-e), American Type Culture Collection, USA (USA 300 FPR3757), (*Mycobacterium smegmatis* mc$^2$155, *Mycobacterium tuberculosis* H37Rv), (*Bacillus subtilis* 168). DSMZ (*Acinetobacter baumannii* DSM-30007, *Eneterococcus faecium* DSM-20477, *Pseudomonas aeruginosa* DSM-19882, *Enterobacter cloacae* subsp. *Cloacae* DSM-30054, *Enterobacter aerogenes* DSM-30053). Clinical *S. aureus* isolates (BK95395, BK97296, IS050678, IS050611, VA417350, VA418879, VA402923, VA412350, VA409044, VA402525) were a kind gift from Prof. Markus Gerhard at the Institute of Medical Microbiology and Immunology, Technische Universität München. *Escherichia coli* CFT073 was a kind gift from Dr. Guiseppe Magistro (Klinikum d. Universität München Urologische Klinik).

Bacterial growth media: LB-medium (1% peptone, 0.5% NaCl, 0.5% yeast extract, pH 7.5), B-medium (1% peptone, 0.5% NaCl, 0.5% yeast extract, 0.1% K2HPO4, pH 7.5); BHB-medium (Brain Heart Infusion, 0.75% brain infusion, 1% heart infusion, 1% peptone, 0.5% NaCl, 0.25% Na2HPO4, 0.2% glucose, pH 7.4); 7H99 medium (4.7 g/L 7H9 powder, 2 mL/L glycerol, 2.5 mL/L 20% Tween 80, 5 g/L BSA (fraction V), 2 g/L dextrose, 850 mg/L NaCl, 3 mg/L catalase).

2) Compounds

Probe Compound

N-(2-(3-(but-3-yn-1-yl)-3H-diazirin-3-yl)ethyl)-4-(4-(3-(4-chloro-3-(trifluoromethyl)phenyl)ureido) phenoxy)picolinamide (PK/X17-1-058)

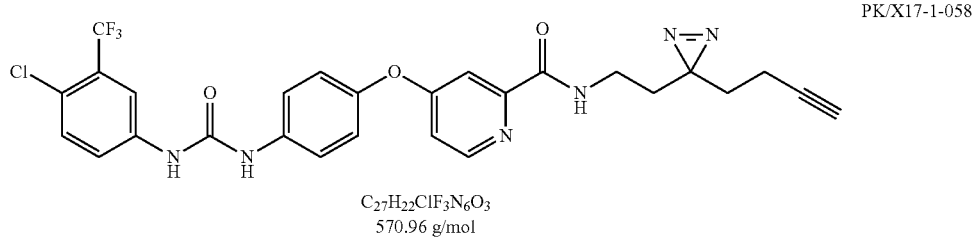 [SMILES: C#CCCC1(CCNC(=O)c2cc(Oc3ccc(NC(=O)Nc4ccc(Cl)c(C(F)(F)F)c4)cc3)ccn2)N=N1]

PK/X17-1-058

$C_{27}H_{22}ClF_3N_6O_3$
570.96 g/mol

To a solution of 4-(4-(3-(4-chloro-3-(trifluoromethyl)phenyl)ureido)phenoxy)picolinic acid (23.1 mg, 0.0511, 1.0 eq.) in dry DMF (0.5 mL) was added HOBt (8.28 mg, 0.0613 mmol, 1.2 eq.), EDC (11.8 mg, 0.0613, 1.2 eq.) and DIEA (17.8 µL, 13.2 mg, 0.102 mmol, 2.0 eq.). After the addition of a solution of 2-(3-(but-3-yn-1-yl)-3H-diazirin-3-yl)ethan-1-amine (Li, Z. et al. Design and synthesis of minimalist terminal alkyne-containing diazirine photo-crosslinkers and their incorporation into kinase inhibitors for cell- and tissue-based proteome profiling. Angew. Chem. Int. Ed. Engl. 52, 8551-6 (2013)) (7.71 mg, 0.0562 mmol, 1.1 eq.) in dry DMF (0.5 mL) the mixture was stirred at room temperature for 24 h. The solvent was removed and the residue was purified flash column chromatography on silica (Hex/EtOAc=2/3) to yield the desired product.

Yield: 60% (17.6 mg, 0.0308 mmol); workup A ($CH_2Cl_2$/MeOH=99/1).

$^1$H NMR (500 MHz, DMSO-$d_6$): $\delta$ [ppm]=9.25 (s, 1H), 9.03 (s, 1H), 8.85 (t, J=6.1 Hz, 1H), 8.52 (d, J=5.6 Hz, 1H), 8.13 (d, J=2.4 Hz, 1H), 7.68-7.58 (m, 4H), 7.37 (d, J=2.6 Hz, 1H), 7.20-7.16 (m, 3H), 3.17 (q, J=7.0 Hz, 2H), 2.83 (t, J=2.7 Hz, 1H), 2.00 (td, J=7.4, 2.7 Hz, 2H), 1.63 (t, J=7.2 Hz, 2H), 1.59 (t, J=7.4 Hz, 2H).

$^{13}$C NMR (126 MHz, DMSO-d$_6$): δ [ppm]=166.1, 163.3, 152.5, 152.2, 150.4, 147.8, 139.4, 137.1, 132.1, 126.7 (q, J=30.3 Hz), 123.2, 123.2 (m), 121.6, 122.9 (q, J=273.3 Hz), 120.5, 116.9 (q, J=5.3 Hz), 114.2, 108.7, 83.2, 71.9, 34.1, 32.0, 31.3, 27.3, 12.7 (observed complexity is due to the C—F splitting).

ESI-HR-MS (m/z) [M+H$^+$] 571.1467 calcd. for C$_{27}$H$_{23}$ClF$_3$N$_6$O$_3$$^+$; found, 571.1472.

2.2) General Procedure for the Synthesis of Urea and Thiourea Containing Compounds A solution of the corresponding commercially available isocyanate or thioisocyanate (1.1 eq.) in dry dichloromethane (3 mL) was cooled to 0° C. After the addition of the corresponding amine (1.0 eq.) the reaction mixture was allowed to warm to room temperature and the reaction was stirred at room temperature for 20 h. Individual work up and purification yielded the desired urea or thiourea containing compounds. In brief, the solvent was removed followed either by purification by flash column chromatography on silica (Hex/EtOAc or CH$_2$Cl$_2$/MeOH; workup A) or by the precipitation from DMF through the addition of water (10 fold excess) and collection of the product by centrifugation (17000 g, 10 min) (workup B).

Example 1

Methyl 3-(4-(3-(4-chloro-3-(trifluoromethyl)phenyl)ureido)phenoxy)benzoate (PK/X17-1-052)

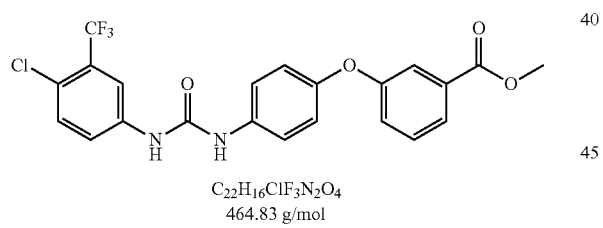

C$_{22}$H$_{16}$ClF$_3$N$_2$O$_4$
464.83 g/mol

Yield: 91% (1.40 g, 3.01 mmol); workup A (CH$_2$Cl$_2$/MeOH=99/1).

$^1$H NMR (250 MHz, CDCl$_3$): δ [ppm]=7.78-7.72 (m, 1H), 7.69 (br s, 1H), 7.60-7.55 (m, 2H), 7.45 (br s, 1H), 7.41-7.27 (m, 3H), 7.20-7.09 (m, 3H), 6.92-6.84 (m, 2H), 3.89 (s, 3H).

$^{13}$C NMR (63 MHz, CDCl$_3$): δ [ppm]=167.1, 157.6, 153.9, 153.6, 137.2, 133.1, 132.1, 131.9, 130.1, 128.9 (q, J=31.6 Hz), 126.4 (m), 124.6, 124.1, 123.6, 123.4, 122.6 (q, J=273.3 Hz), 120.0, 119.2, 119.1 (m), 52.5 (observed complexity is due to the C—F splitting).

ESI-HR-MS (m/z) [M+H$^+$] 465.0824 calcd. for C$_{22}$H$_{17}$ClF$_3$N$_2$O$_4$$^+$; found, 465.0825.

Example 2

1-(4-Benzoylphenyl)-3-(4-chloro-3-(trifluoromethyl)phenyl)urea (PK/X17-1-144)

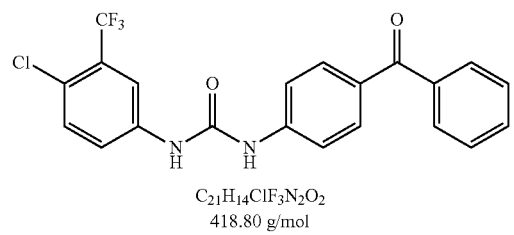

C$_{21}$H$_{14}$ClF$_3$N$_2$O$_2$
418.80 g/mol

Yield: 70% (121 mg, 0.289 mmol); workup B.

$^1$H NMR (500 MHz, DMSO-d$_6$): δ [ppm]=9.35 (s, 1H), 9.31 (s, 1H), 8.16-8.11 (m, 1H), 7.77-7.62 (m, 9H), 7.56 (t, J=7.6 Hz, 2H).

$^{13}$C NMR (126 MHz, DMSO-d$_6$): δ [ppm]=194.5, 152.2, 143.8, 139.0, 137.7, 132.2, 132.1, 131.4, 130.4, 129.3, 128.5, 126.8 (q, J=30.7 Hz), 123.4, 122.8, 122.8 (q, J=273.0 Hz), 117.6, 117.0 (q, J=5.7 Hz) (observed complexity is due to the C—F splitting).

ESI-HR-MS (m/z) [M+H$^+$] 419.0769 calcd. for C$_{21}$H$_{16}$ClF$_3$N$_2$O$_2$$^+$; found, 419.0766.

Example 3

4-(3-(4-Chloro-3-(trifluoromethyl)phenyl)ureido)-N-methylbenzamide (PK/X17-1-145)

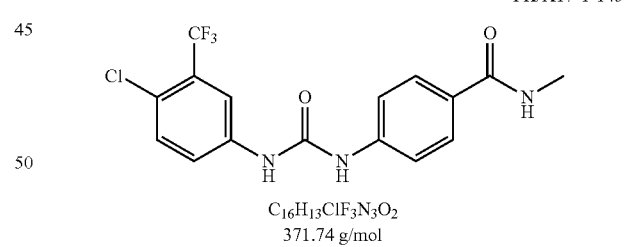

C$_{16}$H$_{13}$ClF$_3$N$_3$O$_2$
371.74 g/mol

Yield: 64% (98.2 mg, 0.264 mmol); workup B.

$^1$H NMR (500 MHz, DMSO-d$_6$): δ [ppm]=9.25 (s, 1H), 9.10 (s, 1H), 8.31 (q, J=4.2 Hz, 1H), 8.14-8.11 (m, 1H), 7.78 (d, J=8.8 Hz, 2H), 7.66-7.61 (m, 2H), 7.53 (d, J=8.8 Hz, 2H), 2.76 (d, J=4.5 Hz, 3H).

$^{13}$C NMR (126 MHz, DMSO-d$_6$): δ [ppm]=166.1, 152.3, 141.8, 139.2, 132.1, 128.1, 128.0, 126.8 (q, J=30.5 Hz), 123.2, 122.8 (q, J=273.0 Hz), 122.5 (m), 117.6, 116.9 (q, J=5.8 Hz), 26.2 (observed complexity is due to the C—F splitting).

Example 4

1-(4-Chloro-3-(trifluoromethyl)phenyl)-3-(2,2-difluorobenzo[d][1,3]dioxol-5-yl)urea (PK/X17-1-150)

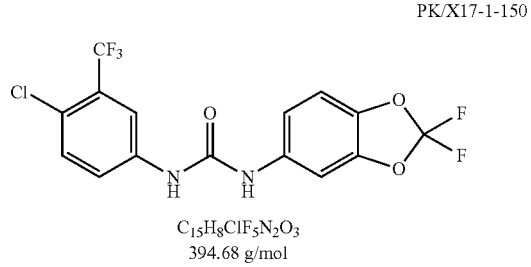 [SMILES: O=C(Nc1ccc2c(c1)OC(F)(F)O2)Nc1ccc(Cl)c(C(F)(F)F)c1]

PK/X17-1-150

$C_{15}H_8ClF_5N_2O_3$
394.68 g/mol

Yield: 91% (148 mg, 0.375 mmol); workup A ($CH_2Cl_2$/MeOH=99/1).

$^1$H NMR (500 MHz, DMSO-$d_6$): δ [ppm]=9.22 (s, 1H), 9.07 (s, 1H), 8.09 (d, J=2.3 Hz, 1H), 7.68-7.59 (m, 3H), 7.33 (d, J=8.7 Hz, 1H), 7.12 (dd, J=8.8, 2.2 Hz, 1H).

$^{13}$C NMR (126 MHz, DMSO-$d_6$): δ [ppm]=152.5, 142.8, 139.2, 137.8, 136.0, 132.0, 131.3 (t, J=252.2 Hz), 126.7 (q, J=30.5 Hz), 123.2, 122.8 (q, J=273.1 Hz), 122.5 (m), 116.9 (q, J=6.0 Hz), 114.2, 110.1, 101.7 (observed complexity is due to the C—F splitting).

ESI-HR-MS (m/z) [M+H$^+$] 395.0216 calcd. for $C_{16}H_9ClF_6N_2O_3{}^+$; found, 395.0211.

Example 5

1-(4-Chloro-3-(trifluoromethyl)phenyl)-3-(4-methoxyphenyl)urea (PK/X17-1-155)

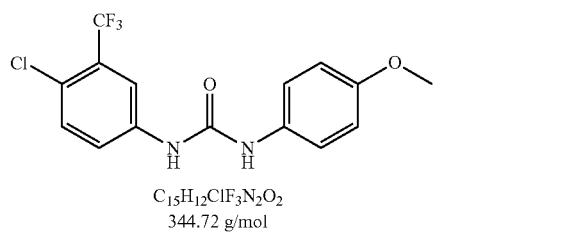

PK/X17-1-155

$C_{15}H_{12}ClF_3N_2O_2$
344.72 g/mol

Yield: 40% (56.6 mg, 0.164 mmol); workup B.

$^1$H NMR (500 MHz, DMSO-$d_6$): δ [ppm]=9.08 (s, 1H), 8.64 (s, 1H), 8.10 (d, J=2.2 Hz, 1H), 7.65-7.57 (m, 2H), 7.36 (d, J=8.9 Hz, 2H), 6.87 (d, J=8.9 Hz, 2H), 3.72 (s, 3H).

$^{13}$C NMR (126 MHz, DMSO-$d_6$): δ [ppm]=154.8, 152.6, 139.6, 132.1, 132.0, 126.7 (q, J=30.5 Hz), 122.9, 122.9 (q, J=273.0 Hz), 122.0, 120.6, 116.7 (q, J=5.6 Hz), 114.0, 55.2.

ESI-HR-MS (m/z) [M+H$^+$] 345.0612 calcd. for $C_{15}H_{13}ClF_3N_2O_2{}^+$; found, 345.0608.

The analytical data corroborate with the literature data in Zhang, L., Darko, A. K., Johns, J. I. and McElwee-White, L. (2011), Eur. J. Org. Chem., 2011: 6261-6268. doi: 10.1002/ejoc.201100657.

Example 6

1-(Benzo[d][1,3]dioxol-5-yl)-3-(4-chloro-3-(trifluoromethyl)phenyl)urea (PK/X17-1-159)

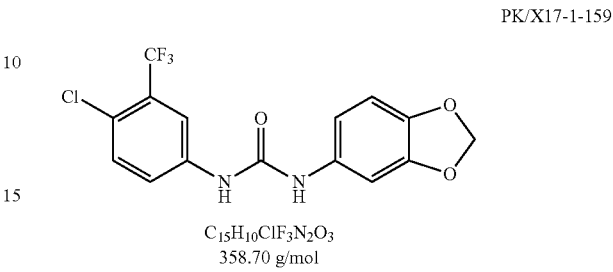

PK/X17-1-159

$C_{15}H_{10}ClF_3N_2O_3$
358.70 g/mol

Yield: 26% (37.7 mg, 0.105 mmol); workup A ($CH_2Cl_2$/MeOH=99/1).

$^1$H NMR (500 MHz, DMSO-$d_6$): δ [ppm]=9.11 (s, 1H), 8.74 (s, 1H), 8.08 (d, J=2.2 Hz, 1H), 7.64-7.58 (m, 2H), 7.18 (d, J=2.0 Hz, 1H), 6.84 (d, J=8.3 Hz, 1H), 6.79 (dd, J=8.4, 2.0 Hz, 1H), 5.98 (s, 2H).

$^{13}$C NMR (126 MHz, DMSO-$d_6$): δ [ppm]=152.5, 147.2, 142.4, 139.5, 133.5, 132.0, 126.7 (q, J=30.6 Hz), 123.0, 122.9 (q, J=273.1 Hz), 122.1 (m), 116.7 (m), 111.6, 108.1, 101.4, 100.9 (observed complexity is due to the C—F splitting).

ESI-HR-MS (m/z) [M+H$^+$] 359.0405 calcd. for $C_{15}H_{11}ClF_3N_2O_3{}^+$; found, 359.0407.

Example 7

1-(4-Chloro-3-(trifluoromethyl)phenyl)-3-(3,4-dimethoxyphenyl)urea (PK/X17-1-160)

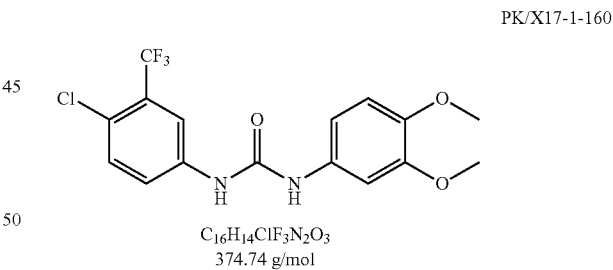

PK/X17-1-160

$C_{16}H_{14}ClF_3N_2O_3$
374.74 g/mol

Yield: 96% (147 mg, 0.392 mmol); workup A ($CH_2Cl_2$/MeOH=99/1).

$^1$H NMR (500 MHz, DMSO-$d_6$): δ [ppm]=9.07 (s, 1H), 8.68 (s, 1H), 8.09 (d, J=2.3 Hz, 1H), 7.65-7.57 (m, 2H), 7.21-7.17 (m, 1H), 6.91-6.85 (m, 2H), 3.74 (s, 3H), 3.71 (s, 3H).

$^{13}$C NMR (126 MHz, DMSO-$d_6$): δ [ppm]=152.5, 148.7, 144.4, 139.5, 132.7, 132.0, 126.7 (q, J=30.5 Hz), 123.0, 122.9 (q, J=273.1 Hz), 122.1 (m), 116.7 (q, J=5.7 Hz), 112.3, 110.7, 104.3, 55.8, 55.4 (observed complexity is due to the C—F splitting).

ESI-HR-MS (m/z) [M+H$^+$] 375.0718 calcd. for $C_{16}H_{16}ClF_3N_2O_3{}^+$; found, 375.0720.

Example 8

1-(4-Chloro-3-(trifluoromethyl)phenyl)-3-(3,4,5-trimethoxyphenyl)urea (PK/X17-1-162)

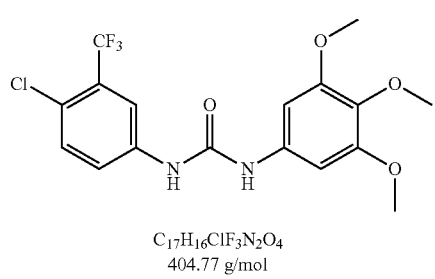

PK/X17-1-162

$C_{17}H_{16}ClF_3N_2O_4$
404.77 g/mol

Yield: 98% (163 mg, 0.402 mmol); workup A ($CH_2Cl_2$/MeOH=99/1).

$^1$H NMR (500 MHz, DMSO-$d_6$): δ [ppm]=9.10 (s, 1H), 8.79 (s, 1H), 8.09 (d, J=2.4 Hz, 1H), 7.67-7.58 (m, 2H), 6.80 (s, 2H), 3.75 (s, 6H), 3.61 (s, 3H).

$^{13}$C NMR (126 MHz, DMSO-$d_6$): δ [ppm]=152.9, 152.4, 139.4, 135.3, 132.8, 132.0, 126.7 (q, J=30.6 Hz), 123.2, 122.9 (q, J=273.1 Hz), 122.3 (m), 116.8 (q, J=5.6 Hz), 96.4, 60.1, 55.7 (observed complexity is due to the C—F splitting).

ESI-HR-MS (m/z) [M+H$^+$] 405.0824 calcd. for $C_{17}H_{17}ClF_3N_2O_4^+$; found, 405.0828.

Example 9

1-(4-Chloro-3-(trifluoromethyl)phenyl)-3-(2,2-difluorobenzo[d][1,3]dioxol-4-yl)urea (PK/X17-1-164)

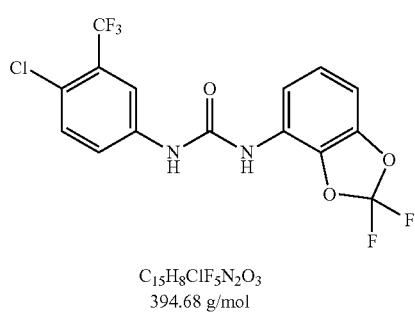

PK/X17-1-164

$C_{15}H_8ClF_5N_2O_3$
394.68 g/mol

Yield: 38% (62 mg, 0.157 mmol); workup A (Hex/EtOAc=4/1).

$^1$H NMR (500 MHz, DMSO-$d_6$): δ [ppm]=9.40 (br s, 1H), 9.04 (br s, 1H), 8.09 (s, 1H), 7.66 (dd, J=8.5, 1.1 Hz, 1H), 7.65-7.61 (m, 2H), 7.16 (t, J=8.3 Hz, 1H), 7.11-7.07 (m, 1H).

$^{13}$C NMR (126 MHz, DMSO-$d_6$): δ [ppm]=151.8, 143.1, 138.9, 133.0, 132.1, 131.0 (t, J=252.5 Hz), 126.8 (q, J=30.8 Hz), 124.5, 123.2, 123.0, 122.8, 122.8 (q, J=273.1 Hz), 116.9 (q, J=5.6 Hz), 116.5, 104.4 (observed complexity is due to the C—F splitting).

ESI-HR-MS (m/z) [M+H$^+$] 395.0216 calcd. for $C_{16}H_9ClF_6N_2O_3^+$; found, 395.0216.

Example 10

1-(4-Chloro-3-(trifluoromethyl)phenyl)-3-(2,2-difluorobenzo[d][1,3]dioxol-5-yl)thiourea (PK/X17-1-166)

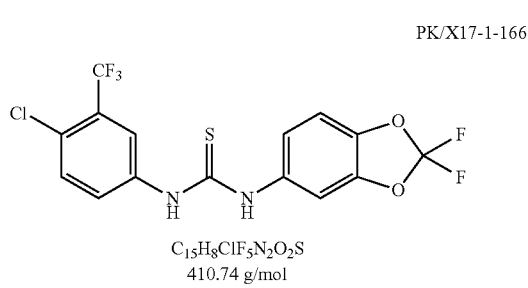 [SMILES: FC1(F)Oc2ccc(NC(=S)Nc3ccc(Cl)c(C(F)(F)F)c3)cc2O1]

PK/X17-1-166

$C_{15}H_8ClF_5N_2O_2S$
410.74 g/mol

Yield: 74% (128 mg, 0.312 mmol); workup A ($CH_2Cl_2$/MeOH=99/1).

$^1$H NMR (500 MHz, DMSO-$d_6$): δ [ppm]=10.17 (s, 1H), 10.05 (s, 1H), 8.06 (d, J=2.5 Hz, 1H), 7.78 (dd, J=8.7, 2.5 Hz, 1H), 7.67 (d, J=8.7 Hz, 1H), 7.61 (d, J=2.1 Hz, 1H), 7.40 (d, J=8.6 Hz, 1H), 7.14 (dd, J=8.6, 2.1 Hz, 1H).

$^{13}$C NMR (126 MHz, DMSO-$d_6$): δ [ppm]=180.3, 142.5, 140.1, 139.1, 135.3, 131.6, 131.4 (t, J=252.5 Hz), 128.9, 126.1 (q, J=30.8 Hz), 125.5 (m), 122.9 (q, J=5.6 Hz), 122.7 (q, J=273.1 Hz), 120.7, 109.9, 107.8 (observed complexity is due to the C—F splitting).

ESI-HR-MS (m/z) [M+H$^+$] 410.9988 calcd. for $C_{16}H_9ClF_6N_2O_8S^+$; found, 410.9986.

Example 11

1-(4-Chloro-3-(trifluoromethyl)phenyl)-3-(naphthalen-2-yl)urea (PK/X17-4-002)

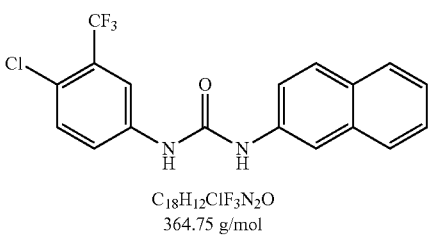

PK/X17-4-002

$C_{18}H_{12}ClF_3N_2O$
364.75 g/mol

Yield: 29% (43.0 mg, 0.118 mmol); workup A (Hex/EtOAc=4/1).

$^1$H NMR (500 MHz, DMSO-$d_6$): δ [ppm]=9.25 (s, 1H), 9.07 (s, 1H), 8.18 (d, J=2.4 Hz, 1H), 8.13 (d, J=1.9 Hz, 1H), 7.87-7.79 (m, 3H), 7.68-7.61 (m, 2H), 7.50 (dd, J=8.8, 2.1 Hz, 1H), 7.48-7.44 (m, 1H), 7.39-7.35 (m, 1H).

$^{13}$C NMR (126 MHz, DMSO-$d_6$): δ [ppm]=152.5, 139.4, 136.9, 133.7, 132.1, 129.3, 128.5, 127.5, 127.1, 126.8 (q, J=30.6 Hz), 126.4, 124.2, 123.1, 122.9 (q, J=273.0 Hz), 122.4, 119.8, 116.8 (q, J=5.6 Hz), 114.0 (observed complexity is due to the C—F splitting).

ESI-HR-MS (m/z) [M+H$^+$] 365.0663 calcd. for $C_{18}H_{13}ClF_3N_2O^+$; found, 365.0662.

Example 12

1-(4-Benzylphenyl)-3-(4-chloro-3-(trifluoromethyl)phenyl)urea (PK/X17-4-003)

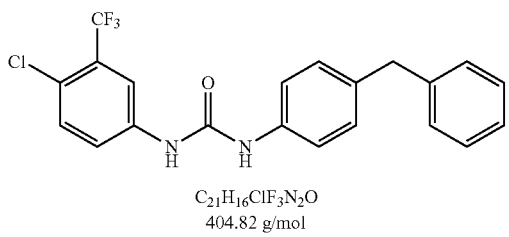

C$_{21}$H$_{16}$ClF$_3$N$_2$O
404.82 g/mol

Yield: 72% (120 mg, 0.296 mmol); workup A (Hex/EtOAc=3/1).

$^1$H NMR (300 MHz, DMSO-d$_6$): δ [ppm]=9.13 (br s, 1H), 8.78 (br s, 1H), 8.10 (d, J=2.0 Hz, 1H), 7.66-7.56 (m, 2H), 7.37 (d, J=8.5 Hz, 2H), 7.32-7.11 (m, 7H), 3.88 (s, 2H).

$^{13}$C NMR (75 MHz, DMSO-d$_6$): δ [ppm]=152.4, 141.6, 139.4, 137.1, 135.2, 132.0, 129.0, 128.6, 128.4, 126.7 (q, J=30.5 Hz), 125.9, 122.9, 122.8 (q, J=273.0 Hz), 122.1 (m), 118.9, 116.6 (q, J=6.0 Hz), 40.5 (observed complexity is due to the C—F splitting).

ESI-HR-MS (m/z) [M+H$^+$] 405.0976 calcd. for C$_{21}$H$_{17}$ClF$_3$N$_2$O$^+$; found, 405.0975.

Example 13

1-(4-Chloro-3-(trifluoromethyl)phenyl)-3-(4-ethylphenyl)urea (PK/X17-4-004)

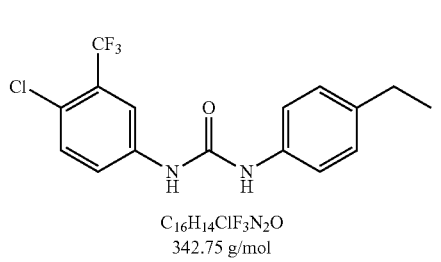

C$_{16}$H$_{14}$ClF$_3$N$_2$O
342.75 g/mol

Yield: 78% (110 mg, 0.320 mmol); workup A (Hex/EtOAc=3/1).

$^1$H NMR (500 MHz, DMSO-d$_6$): δ [ppm]=9.11 (br s, 1H), 8.74 (br s, 1H), 8.10 (d, J=2.4 Hz, 1H), 7.64-7.58 (m, 2H), 7.36 (d, J=8.5 Hz, 2H), 7.12 (d, J=8.5 Hz, 2H), 2.54 (q, J=7.6 Hz, 2H), 1.15 (t, J=7.6 Hz, 3H).

$^{13}$C NMR (126 MHz, DMSO-d$_6$): δ [ppm]=152.4, 139.5, 137.7, 136.8, 132.0, 128.0, 126.7 (q, J=30.5 Hz), 123.0, 122.9 (q, J=273.0 Hz), 122.1 (m), 118.8, 116.7 (q, J=5.7 Hz), 27.6, 15.8 (observed complexity is due to the C—F splitting).

ESI-HR-MS (m/z) [M+H$^+$] 343.0820 calcd. for C$_{16}$H$_{15}$ClF$_3$N$_2$O$^+$; found, 343.0819.

Example 14

1-(4-Chloro-3-methylphenyl)-3-(2,2-difluorobenzo[d][1,3]dioxol-5-yl)urea (PK/X17-4-017)

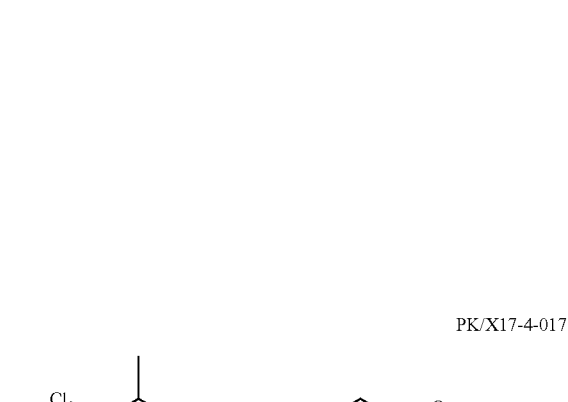

C$_{15}$H$_{11}$ClF$_2$N$_2$O$_3$
340.71 g/mol

Yield: 60% (84.0 mg, 0.247 mmol); workup A (Hex/EtOAc=3/1).

$^1$H NMR (500 MHz, DMSO-d$_6$): δ [ppm]=8.91 (br s, 1H), 8.78 (br s, 1H), 7.65 (d, J=2.1 Hz, 1H), 7.43 (br s, 1H), 7.32-7.29 (m, 3H), 7.08 (dd, J=8.8, 2.2 Hz, 1H), 2.29 (s, 3H).

$^{13}$C NMR (126 MHz, DMSO-d$_6$): δ [ppm]=152.5, 142.8, 138.4, 137.5, 136.4, 135.6, 131.3 (t, J=252.1 Hz), 129.0, 125.9, 120.7, 117.5, 113.7, 110.1, 101.3, 19.9 (observed complexity is due to the C—F splitting).

ESI-HR-MS (m/z) [M+H$^+$] 341.0499 calcd. for C$_{16}$H$_{12}$F$_2$N$_2$O$_3^+$; found, 341.0498.

Example 15

1-(2,2-difluorobenzo[d][1,3]dioxol-5-yl)-3-(3-(trifluoromethyl)phenyl)urea (PK/X17-4-018)

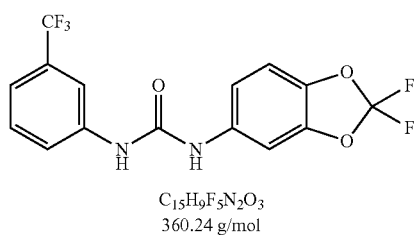

PK/X17-4-018
C$_{15}$H$_9$F$_5$N$_2$O$_3$
360.24 g/mol

Yield: 85% (149 mg, 0.414 mmol); workup A (Hex/EtOAc=3/1).

$^1$H NMR (500 MHz, DMSO-d$_6$): δ [ppm]=9.09 (br s, 1H), 9.00 (br s, 1H), 8.00 (s, 1H), 7.66 (d, J=2.1 Hz, 1H), 7.58 (d, J=8.6 Hz, 1H), 7.51 (t, J=7.9 Hz, 1H), 7.32 (d, J=8.7 Hz, 2H), 7.12 (dd, J=8.7, 2.2 Hz, 1H).

$^{13}$C NMR (75 MHz, DMSO-d$_6$): δ [ppm]=152.5, 142.8, 140.4, 137.7, 136.2, 131.3, 129.9, 129.5 (q, J=31.4 Hz), 124.2 (q, J=272.5 Hz), 122.0, 118.3 (q, J=3.9 Hz), 114.3 (q, J=4.1 Hz), 114.0, 110.0, 101.6 (observed complexity is due to the C—F splitting).

ESI-HR-MS (m/z) [M+H$^+$] 361.0606 calcd. for C$_{16}$H$_{10}$F$_6$N$_2$O$_3$$^+$; found, 361.0605.

Example 16

1-(4-Chloro-3-(trifluoromethyl)phenyl)-3-phenylurea (PK/X17-3-004)

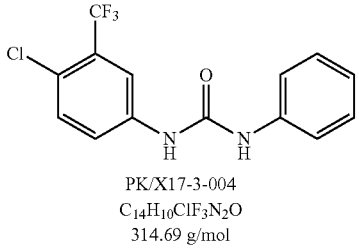 [SMILES: O=C(Nc1ccccc1)Nc1ccc(Cl)c(C(F)(F)F)c1]

PK/X17-3-004
C$_{14}$H$_{10}$ClF$_3$N$_2$O
314.69 g/mol

Yield: 13% (44.0 mg, 0.140 mmol); A (CH$_2$Cl$_2$/MeOH=2/1).

$^1$H NMR (500 MHz, DMSO-d$_6$): δ [ppm]=9.15 (br s, 1H), 8.83 (br s, 1H), 8.11 (d, J=2.3 Hz, 1H), 7.66-7.59 (m, 2H), 7.46 (d, J=7.7 Hz, 2H), 7.29 (t, J=7.9 Hz, 2H), 7.00 (t, J=7.4 Hz, 1H).

$^{13}$C NMR (126 MHz, DMSO-d$_6$): δ [ppm]=152.4, 139.4, 139.2, 132.0, 128.8, 126.7 (q, J=30.5 Hz), 123.0, 122.9 (q, J=273.1 Hz), 122.3, 122.2 (m), 118.6, 116.7 (q, J=5.5 Hz) (observed complexity is due to the C—F splitting).

ESI-HR-MS (m/z) [M+H$^+$] 315.0507 calcd. for C$_{14}$H$_{11}$ClF$_3$N$_2$O$^+$; found, 315.0507.

Example 17

Butyl 4-(3-(4-chloro-3-(trifluoromethyl)phenyl)ureido)benzoate (PK/X17-3-005)

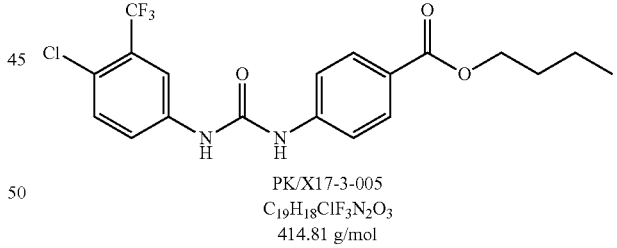

PK/X17-3-005
C$_{19}$H$_{18}$ClF$_3$N$_2$O$_3$
414.81 g/mol

Yield: 93% (200 mg, 0.482 mmol); workup B.

1H NMR (500 MHz, DMSO-d$_6$): δ [ppm]=9.30-9.23 (m, 2H), 8.11 (d, J=2.1 Hz, 1H), 7.89 (d, J=8.7 Hz, 2H), 7.68-7.58 (m, 4H), 4.24 (t, J=6.5 Hz, 2H), 1.72-1.64 (m, 2H), 1.46-1.37 (m, 2H), 0.93 (t, J=7.4 Hz, 3H).

$^{13}$C NMR (126 MHz, DMSO-d$_6$): δ [ppm]=165.4, 152.1, 143.9, 139.0, 132.1, 130.4, 126.8 (q, J=30.8 Hz), 123.3, 123.2, 122.8 (q, J=273.0 Hz), 122.7 (m), 117.7, 117.0 (q, J=5.5 Hz), 64.0, 30.3, 18.8, 13.7 (observed complexity is due to the C—F splitting).

ESI-HR-MS (m/z) [M+H$^+$] 415.1031 calcd. for C$_{19}$H$_{19}$ClF$_3$N$_2$O$_3$$^+$; found, 415.1032.

Example 18

1-(4-Chloro-3-(trifluoromethyl)phenyl)-3-(4-phenoxyphenyl)urea (PK/X17-3-006)

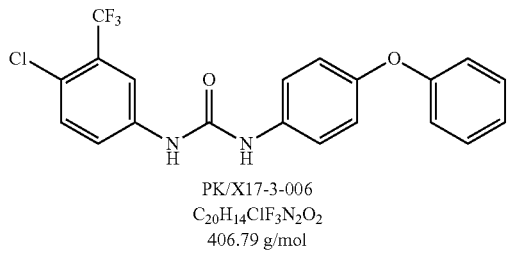 [SMILES: O=C(Nc1ccc(Oc2ccccc2)cc1)Nc1ccc(Cl)c(C(F)(F)F)c1]

PK/X17-3-006
C$_{20}$H$_{14}$ClF$_3$N$_2$O$_2$
406.79 g/mol

Yield: 92% (203 mg, 0.499 mmol); workup B.

$^1$H NMR (500 MHz, DMSO-d$_6$): δ [ppm]=9.13 (s, 1H), 8.84 (s, 1H), 8.11 (d, J=2.3 Hz, 1H), 7.66-7.59 (m, 2H), 7.48 (d, J=8.9 Hz, 2H), 7.36 (t, J=8.0 Hz, 2H), 7.09 (t, J=7.4 Hz, 1H), 7.02-6.94 (m, 4H).

$^{13}$C NMR (126 MHz, DMSO-d$_6$): δ [ppm]=157.5, 152.5, 151.1, 139.4, 135.1, 132.0, 130.0, 126.7 (q, J=30.5 Hz), 123.0, 122.9, 122.9 (q, J=273.0 Hz), 122.2 (m), 120.5, 119.7, 117.7, 116.7 (q, J=5.7 Hz) (observed complexity is due to the C—F splitting).

ESI-HR-MS (m/z) [M+H]$^+$407.0769 calcd. for C$_{20}$H$_{16}$ClF$_3$N$_2$O$_2$$^+$; found, 407.0770.

Example 19

1,1'-(1,3-Phenylene)bis(3-(4-chloro-3-(trifluoromethyl)phenyl)urea (PK/X17-3-003)

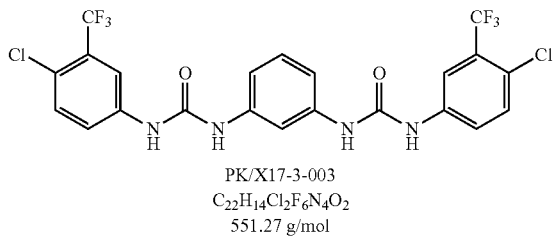 [SMILES: O=C(Nc1cccc(NC(=O)Nc2ccc(Cl)c(C(F)(F)F)c2)c1)Nc1ccc(Cl)c(C(F)(F)F)c1]

PK/X17-3-003
C$_{22}$H$_{14}$Cl$_2$F$_6$N$_4$O$_2$
551.27 g/mol

A solution of 4-chloro-3-(trifluoromethyl)phenyl isocyanate (339 mg, 1.53 mmol, 2.2 eq.) in dry dichloromethane (10 mL) was cooled to 0° C. After the addition of m-phenylenediamine (75.0 mg, 0.694 mmol, 1.0 eq.) the reaction mixture was allowed to warm to room temperature and the reaction was stirred at room temperature for 20 h. The solvent was removed followed by the precipitation from DMF through the addition of water (10 fold excess) and collection of the product by centrifugation (17000 g, 10 min).

Yield: 50% (192 mg, 0.348 mmol).

$^1$H NMR (500 MHz, DMSO-d$_6$): δ [ppm]=9.08 (s, 2H), 8.92 (s, 2H), 8.14 (s, 2H), 7.74 (t, J=2.0 Hz, 1H), 7.61 (d, J=1.4 Hz, 4H), 7.22-7.17 (m, 1H), 7.09 (dd, J=7.9, 2.0 Hz, 2H).

ESI-HR-MS (m/z) [M+H]$^+$ 551.0471 calcd. for C$_{22}$H$_{15}$Cl$_2$F$_6$N$_4$O$_2$$^+$; found, 551.0486.

Reference Example 1

1-(2,2-Difluorobenzo[d][1,3]dioxol-5-yl)-3-phenylurea (PK/X17-4-011)

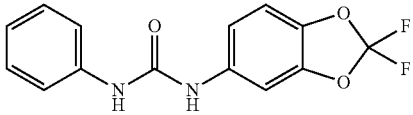

PK/X17-4-011
C$_{14}$H$_{10}$F$_2$N$_2$O$_3$
292.24 g/mol

Yield: 17% (38.0 mg, 0.130 mmol); workup A (Hex/EtOAc=4/1).

$^1$H NMR (500 MHz, DMSO-d$_6$): δ [ppm]=8.88 (s, 1H), 8.72 (s, 1H), 7.66 (d, J=2.1 Hz, 1H), 7.46-7.43 (m, 2H), 7.32-7.26 (m, 3H), 7.08 (dd, J=8.7, 2.2 Hz, 1H), 7.00-6.95 (m, 1H).

$^{13}$C NMR (126 MHz, DMSO-d$_6$): δ [ppm]=152.6, 142.8, 139.5, 137.4, 136.6, 131.3 (t, J=252.2 Hz), 128.8, 122.1, 118.4, 113.5, 110.1, 101.2 (observed complexity is due to the C—F splitting).

ESI-HR-MS (m/z) [M+H$^+$] 293.0732 calcd. for C$_{14}$H$_{11}$F$_3$N$_2$O$_3$$^+$; found, 293.0732.

Reference Example 2

1-(2,2-Difluorobenzo[d][1,3]dioxol-5-yl)-3-(p-tolyl)urea (PK/X17-4-013)

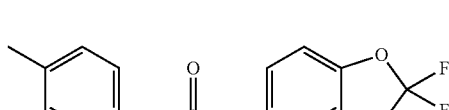

PK/X17-4-013
C$_{15}$H$_{12}$F$_2$N$_2$O$_3$
306.27 g/mol

Yield: 63% (131 mg, 0.428 mmol); workup A (Hex/EtOAc=4/1).

$^1$H NMR (500 MHz, DMSO-d$_6$): δ [ppm]=8.83 (s, 1H), 8.61 (s, 1H), 7.66 (d, J=2.1 Hz, 1H), 7.34-7.28 (m, 3H), 7.10-7.04 (m, 3H), 2.24 (s, 3H).

$^{13}$C NMR (126 MHz, DMSO-d$_6$): δ [ppm]=152.6, 142.8, 137.4, 136.9, 136.7, 131.3 (t, J=252.2 Hz), 130.9, 129.2, 118.5, 113.4, 110.1, 101.1, 20.4 (observed complexity is due to the C—F splitting).

ESI-HR-MS (m/z) [M+H$^+$] 307.0889 calcd. for C$_{16}$H$_{13}$F$_2$N$_2$O$_3$$^+$; found, 307.0887.

Reference Example 3

1-(2,2-Difluorobenzo[d][1,3]dioxol-5-yl)-3-mesitylurea (PK/X17-4-014)

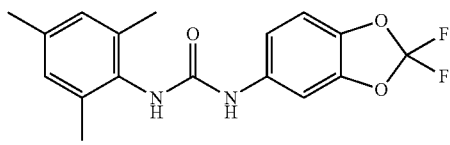

PK/X17-4-014
$C_{17}H_{16}F_2N_2O_3$
334.32 g/mol

Yield: 39% (74.0 mg, 0.221 mmol); workup A (Hex/EtOAc=4/1).

$^1$H NMR (500 MHz, DMSO-$d_6$): δ [ppm]=8.93 (br s, 1H), 7.68 (br s, 1H), 7.65 (d, J=2.1 Hz, 1H), 7.27 (d, J=8.8 Hz, 1H), 7.08 (dd, J=8.8, 2.1 Hz, 1H), 6.88 (s, 2H), 2.22 (s, 3H), 2.14 (s, 6H).

ESI-HR-MS (m/z) [M+H$^+$] 335.1202 calcd. for $C_{17}H_{17}F_2N_2O_3^+$; found, 335.1201.

Reference Example 4

1-(2,2-Difluorobenzo[d][1,3]dioxol-5-yl)-3-octylurea (PK/X17-4-020)

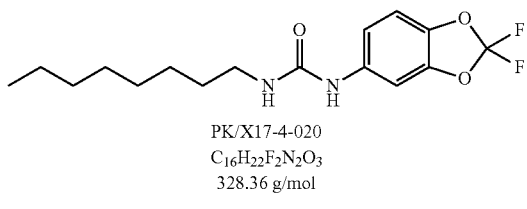 [SMILES: CCCCCCCCNC(=O)Nc1ccc2c(c1)OC(F)(F)O2]

PK/X17-4-020
$C_{16}H_{22}F_2N_2O_3$
328.36 g/mol

Yield: 31% (59.0 mg, 0.180 mmol); workup A (Hex/EtOAc=3/1).

$^1$H NMR (500 MHz, DMSO-$d_6$): δ [ppm]=8.62 (s, 1H), 7.63 (d, J=2.1 Hz, 1H), 7.23 (d, J=8.7 Hz, 1H), 6.96 (dd, J=8.8, 2.1 Hz, 1H), 6.17 (t, J=5.6 Hz, 1H), 3.05 (q, J=6.8 Hz, 2H), 1.45-1.37 (m, 2H), 1.26 (br s, 10H), 0.84 (t, J=6.9 Hz, 3H).

$^{13}$C NMR (126 MHz, DMSO-$d_6$): δ [ppm]=155.1, 142.8, 137.6, 136.8, 131.3 (t, J=252.1 Hz), 112.6, 109.9, 100.4, 39.1, 31.3, 29.7, 28.8, 28.8, 26.4, 22.1, 14.0 (observed complexity is due to the C—F splitting).

ESI-HR-MS (m/z) [M+H$^+$] 329.1671 calcd. for $C_{16}H_{23}F_2N_2O_3^+$; found, 329.1671.

Reference Example 5

N-Methyl-4-(4-(3-phenylureido)phenoxy)picolinamide (PK/X17-2-011)

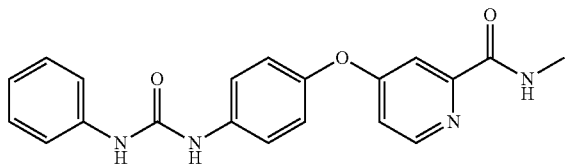

PK/X17-2-011
$C_{20}H_{18}N_4O_3$
362.39 g/mol

Yield: 63% (93.9 mg, 0.259 mmol); workup A (Hex/EtOAc=3/2).

$^1$H NMR (500 MHz, DMSO-$d_6$): δ [ppm]=8.81 (s, 1H), 8.76 (q, J=4.6 Hz, 1H), 8.70 (s, 1H), 8.50 (d, J=5.6 Hz, 1H), 7.58 (d, J=8.9 Hz, 2H), 7.46 (d, J=7.7 Hz, 2H), 7.38 (d, J=2.5 Hz, 1H), 7.31-7.26 (m, 2H), 7.18-7.13 (m, 3H), 7.00-6.96 (m, 1H), 2.78 (d, J=4.9 Hz, 3H).

$^{13}$C NMR (75 MHz, DMSO-$d_6$): δ [ppm]=166.0, 163.8, 152.6, 152.4, 150.4, 147.4, 139.6, 137.6, 128.8, 121.9, 121.5, 119.9, 118.3, 114.0, 108.6, 26.0.

ESI-HR-MS (m/z) [M+H$^+$] 363.4152 calcd. for $C_{20}H_{19}N_4O_3^+$; found, 363.1450.

3) Biological and Pharmacological Tests

3.1) Cytotoxicity Assay (MTT)

The MTT assay was performed in 96 well plates. A549, HeLa and HepG2 cells were seeded with 4000 cells/well, whereas NIH/3T3 cells were seeded with 2000 cells/well. Cells were grown to 30-40% confluence at 37° C. and 5% $CO_2$ over a time span of 24 h. The medium was removed and 100 µL medium/well containing varying concentrations of the respective compound and a final DMSO concentration of 0.1% were added to the cells in triplicates and incubated at 37° C. and 5% $CO_2$ for 24 h. 20 µL Thiazolyl blue tetrazolium bromide (5 mg/mL in PBS, Sigma Aldrich) were added to the cells and incubated at 37° C. and 5% $CO_2$ for 4 h until complete consumption was observed. After removal of the medium, the resulting formazan was dissolved in 200 µL DMSO. Optical density was measured at 570 nm (562 nm) and background subtracted at 630 nm (620 nm) by a TECAN Infinite M200 Pro.

Figure 4:
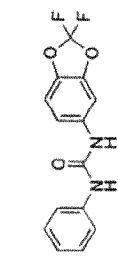
FIG. 4: Cytotoxicity data of sorafenib, a sorafenib derivative (PK/X17-2-011) and two compounds according to the present invention (PK/X17-1-150 and PK/X17-4-011) against human a panel of three human cell lines.
Figure 4:
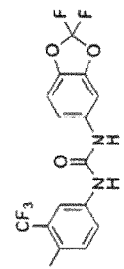
Figure 4:
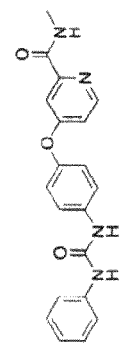
Figure 4:
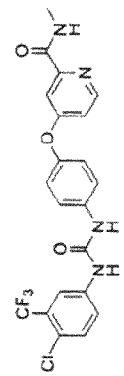

The results of MTT testing in various cell lines (FIG. 4) reveal toxicity of PK/X17-1-150 (example compound 4) at concentrations higher compared to the antibacterial MICs providing a therapeutic window for efficacy studies.

3.2) Plasma Stability Assay

The in vitro stability was tested by a LC-MS based method. Mouse plasma was purchased from biowest (mouse plasma w/lithium heparin, sterile filtered S2162-010) and used as a 1:1 dilution with potassium phosphate buffer (0.1 M, pH 7.4). Final assay concentration of DMSO from compound stocks was 1%. AV1, a β-lactone with known low plasma stability, was used as positive control at a concentration of 50 µM. The compound stability test in plasma was initiated by the addition of 10 µM compound of interest (50 µM in the case of AV1) to 250 µL of diluted mouse plasma at 37° C. Directly after compound addition the reaction mixture was shortly mixed by vortexing and the first sample of 25 µL was withdrawn (time point 0 min). Every sample was quenched immediately by the addition 30 µL of pre-chilled acetonitrile. The reaction mixture was incubated at 37° C. with gentle shaking at 600 rpm. At certain time points (5, 10, 20, 30, 60, 120, 240, 360 min) additional samples (25 µL) were taken for every test compound, quenched as described and stored at −20° C. For analysis by LC-MS all samples were allowed to warm to rt and centrifuged at 17000 g for 5 min. The supernatants were filtered through modified nylon centrifugal filters (0.45 µM) and transferred to LS-MS glass vials. Quantitative LC-MS analysis was performed by LCQ-Fleet Ion Trap Mass Spectrometer equipped with an APCI ion source and a DionexHPLC system using a Waters Xbridge BEH130 C18 column (5 µM 4.6×100 mm). Data analysis was performed by Thermo Scientific Xcalibur software. Shortly, ion peaks from single ion monitoring mass detection were integrated. Peak areas at the time point 0 min were set to 100% and peak decline with time was expressed relative to 100% at t=0 min. Plasma stability was determined in three independent experiments.

Figure 5:
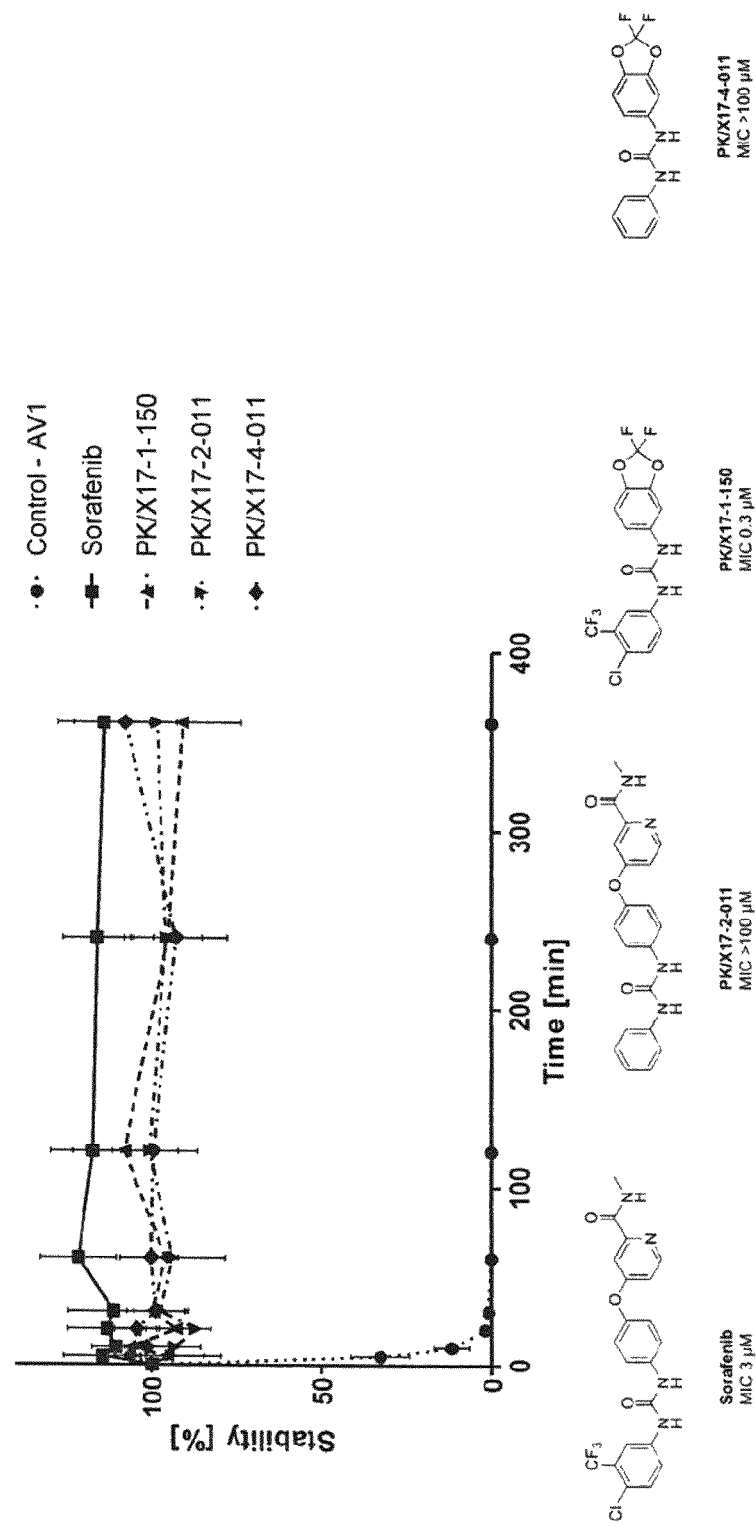
FIG. 5: Stability of sorafenib, a sorafenib derivative (PK/X17-2-011) and two compounds according to the present invention (PK/X17-1-150 and PK/X17-4-011) and negative controls in mouse plasma over a time span of 6 h.

Sorafenib as well as PX/X17-1-150 (example compound 4) exhibit excellent stability in plasma for several hours which represents an ideal condition for clinical studies (FIG. 5).

3.3) Minimal Inhibitory Concentration (MIC)

Minimum inhibitory concentrations (MICs) represent the lowest concentration of sample that will inhibit the visible growth of a microorganism after overnight incubation, and was obtained by a 96 well plate-based assay (Thermo Scientific) with serial dilutions of the probes tested. In the case of *Staphylococcus aureus*, 5 ml of fresh media was inoculated with 5 µL of the corresponding bacterial overnight culture (1:100) and incubated at 37° C. with gentle shaking (200 rpm) until the cultures reached an $OD_{600}$ of 0.4-0.6. Bacteria were diluted in fresh medium to a concentration of $10^5$ CFU/mL. In the case of all other bacteria species tested, fresh media was inoculated 1/10000 and directly used for testing. Diluted bacterial cultures (99 µL) were added to various concentrations of probe (1 µL of the respective stock in DMSO). A growth control containing DMSO (1 µL) and cultivated medium (99 µL) and a sterile control containing fresh medium (100 µL) were run on every 96 well plate in triplicates. After incubation at 37° C. with gentle shaking (200 rpm) for 24 h, the dilution series was analysed for microbial growth, usually indicated by turbidity and/or a pellet of bacteria at the bottom of the well. The lowest concentration in the dilution series at which no growth of bacteria could be observed by eye was defined as the minimum inhibitory concentration (MIC) of the probe. MIC values were determined by three independent experiments with at least triplicate runs for each concentration.

The antibacterial activity of example compound 4 was demonstrated in an in vitro test. Sorafenib was tested as a reference. Both compounds were tested against various bacterial strains. LB medium: 1% peptone, 0.5% NaCl, 0.5% yeast extract, pH 7.5; B medium: 1% peptone, 0.5% NaCl, 0.5% yeast extract, 0.1% K2HPO4, pH 7.5; BHB medium: 0.75% brain infusion, 1% heart infusion, 1% peptone, 0.5% NaCl, 0.25% Na2HPO4, 0.2% glucose, pH 7.4.

TABLE 1

$IC_{50}$ values for inhibition of bacterial growth.

| strain | medium | MIC (µM) of Example compound 4 | MIC (µM) of Sorafenib |
|---|---|---|---|
| Staphylococcus aureus USA300 | B | 0.3 | 3 |
| S. aureus Mu50 | B | 0.3 | 3 |
| Staphylococcus aureus DSM18827 | B | 0.3 | 3 |
| Staphylococcus aureus NCTC8325 | B | 0.3 | 3 |
| Staphylococcus aureus Bk95395 | B | 0.3 | 5 |
| Staphylococcus aureus Bk97296 | B | 0.3 | 5 |
| Staphylococcus aureus IS050678 | B | 0.3 | 5 |
| Staphylococcus aureus IS050611 | B | 0.3 | 3 |
| Staphylococcus aureus VA417350 | B | 0.3 | 5 |
| Staphylococcus aureus VA418879 | B | 0.3 | 5 |
| Staphylococcus aureus VA402923 | B | 0.3 | 5 |
| Staphylococcus aureus VA412350 | B | 0.3 | 5 |
| Staphylococcus aureus VA409044 | B | 0.3 | 3 |
| Staphylococcus aureus VA402525 | B | 0.3 | 5 |
| Mycobacterium smegmatis mc$^2$ 155 | LB | 1 | 6 |
| Mycobacterium tuberculosis H37Rv | 7H9 | 2 | 25 |
| Bacillus subtilis | LB | 1 | 5 |
| Acinetobacter baumannii | B | 10 | >100 |
| Pseudomonas aeruginosa | B | >100 | >100 |
| Enterobacter cloacae subsp. Cloacae | B | >100 | >100 |
| Enterobacter aerogenes | B | >100 | >100 |

The antibacterial activity of compounds of the invention was demonstrated in an in vitro test in which the compounds were tested against *S. aureus* NCTC 8325 by minimum inhibitory concentration (MIC) assays. The assay was performed as described above.

TABLE 2

$IC_{50}$ values for inhibition of bacterial growth of *S. aureus* NCTC 8325.

| Compound of example no. | $IC_{50}$ (µM) |
|---|---|
| 1 | 0.5 |
| 2 | 1 |
| 3 | 30 |
| 4 | 0.3 |
| 5 | 3 |
| 6 | 10 |
| 7 | 30 |
| 8 | 30 |
| 9 | 1 |
| 10 | 1 |
| 11 | 1 |
| 12 | 1 |
| 13 | 1 |
| 14 | 1 |
| 15 | 1 |
| 16 | 3 |
| 17 | 0.6 |

TABLE 2-continued

IC$_{50}$ values for inhibition of bacterial growth of S. aureus NCTC 8325.

| Compound of example no. | IC$_{50}$ (µM) |
| --- | --- |
| 18 | 0.6 |
| 19 | 1 |
| Reference Example 1 | >100 |
| Reference Example 2 | >100 |
| Reference Example 3 | >100 |
| Reference Example 4 | >100 |
| Reference Example 5 | >100 |
| Probe compound (PK/X17-1-058) | 10 |

3.4) Resistance Development Assay

For resistance development by sequential passaging, exponential growing S. aureus NCTC 8325 was diluted 1:100 in 1 mL MHB medium containing sorafenib, example compound 4 (PK/X17-1-150) or Ofloxacin as positive control as well as DMSO or 0.1 M NaOH as growth/negative controls. Bacteria were incubated at 37° C. with shaking at 200 rpm, and passaged in 24 h intervals in the presence of sorafenib, example compound 4 (PK/X17-1-150) or Ofloxacin at different concentrations (0.25×MIC, 0.5×MIC, 1×MIC, 2×MIC, 4×MIC). Cultures from the second highest concentrations that allowed growth (OD$_{600}$≥3) were diluted 1:100 into fresh media containing different concentrations of the respective antimicrobial (0.25×MIC, 0.5×MIC, 1×MIC, 2×MIC, 4×MIC). If a shift in MIC levels was observed, concentrations of the respective antimicrobial were adjusted accordingly for the following passaging. This serial passaging was repeated for 27 days.

Figure 6:
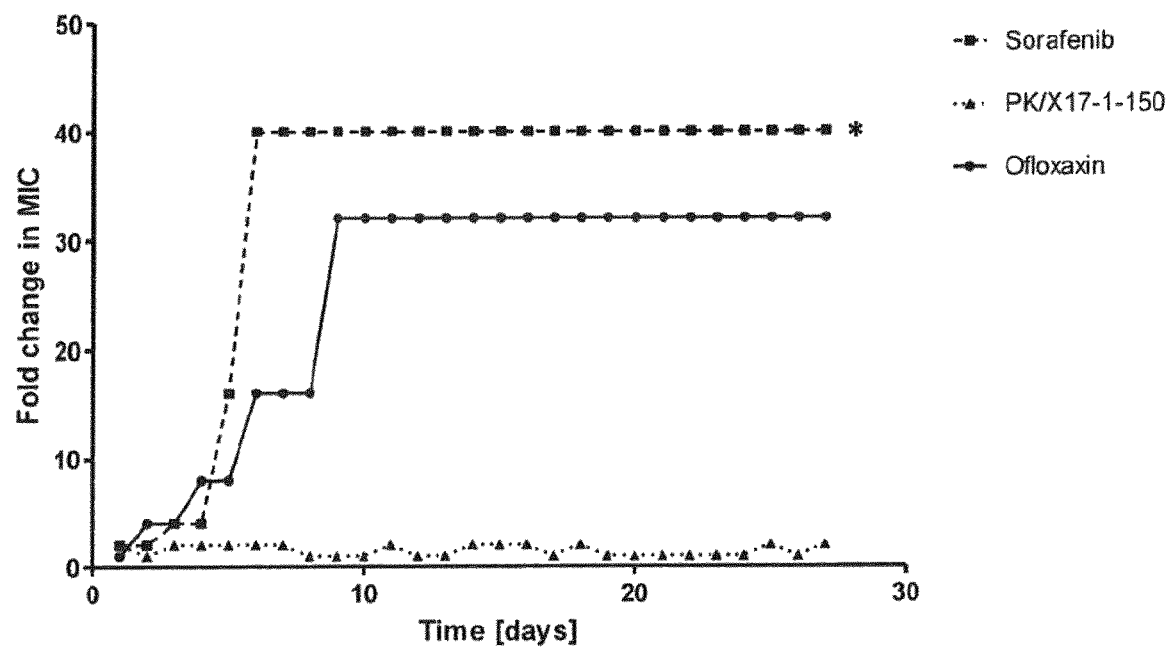
FIG. 6: Multiple passages of *S. aureus* with PK/X17-1-150, ofloxacin and sorafenib showed rapid resistance development in case of sorafenib and ofloxacin. PK/X17-1-150 (example compound 4), a compound according to the present invention, did not induce resistance. MIC: minimal inhibitory concentration, the lowest concentration of a given compound where no bacterial growth can be detected.
Figure 6:
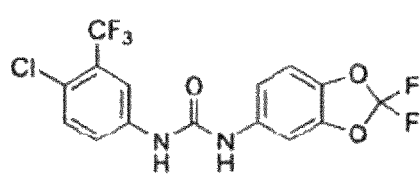

Serial passaging of S. aureus in the presence of subinhibitory levels of example compound 4 (PK/X17-1-150) over a period of 27 days showed no resistant development, whereas serial passaging of S. aureus in the presence sorafenib resulted in resistance development within the same time frame (FIG. 6). Bacteria showed first signs of lower sensitivity against sorafenib within the first 5 days, while the minimal inhibitory concentration increased by a factor 40 within the first 10 days. Furthermore, preliminary results indicate that PK/X17-1-150 (example compound 4) is still active against S. aureus that developed resistance against sorafenib.

3.5) Activity Based Protein Profiling with Photoprobe X17PP1 (pABPP, Probe Compound) in S. aureus NCTC8325

Figure 3:
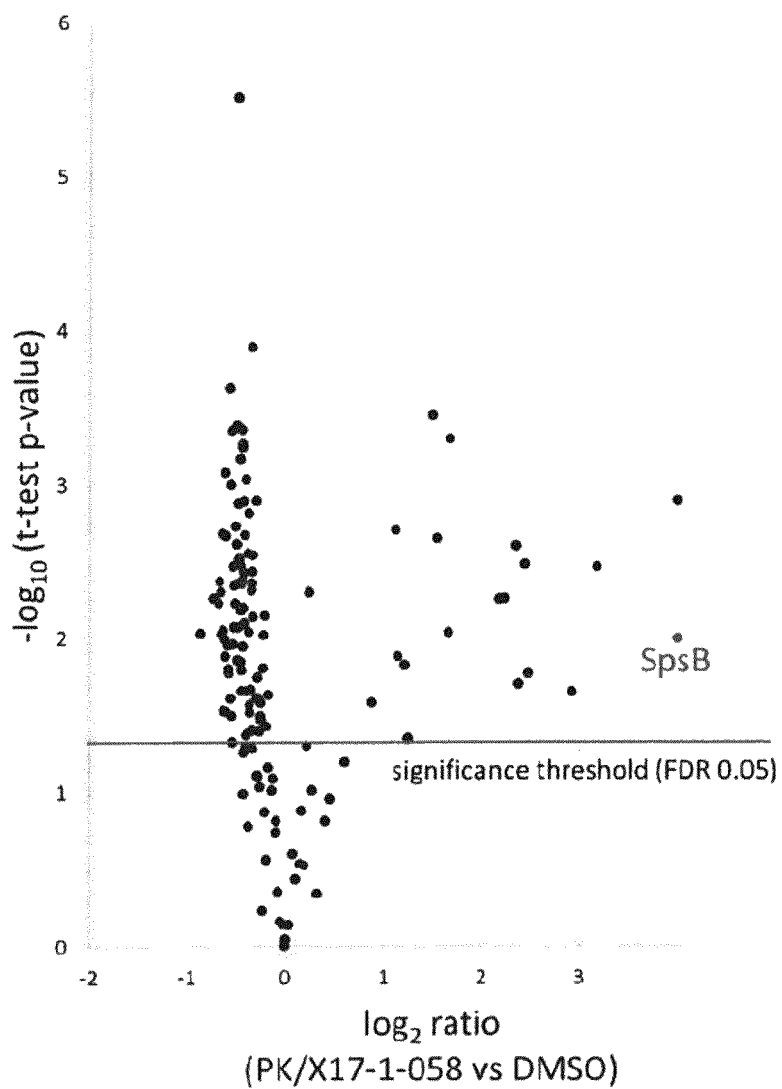
FIG. 3: Vulcano plot—target identification of sorafenib in multi-resistant *S. aureus* utilizing the affinity-based protein profiling (AfBPP) platform. Protein hits that are enriched compared to the control and of statistical significance are shown on the upper right. Signal peptidase B (SpsB) is a predominant target identified by these experiments.
Figure 3:
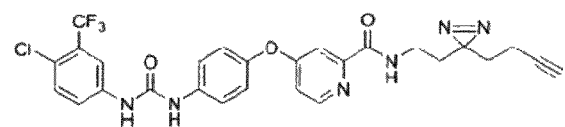

The gel-free affinity-based protein profiling (AfBPP) platform (Evans, M. J.; Cravatt, B. F. Chem. Rev. 2006, 106 (8), 3279-3301) was utilized to identify the protein target of sorafenib and structurally related compounds in S. aureus. A photoreactive derivative of sorafenib (PK/X17-1-058 (Probe compound)) bearing a terminal alkyne handle was incubated with S. aureus cells in vivo. After irradiation the cells were lysed and the terminal alkyne modified with a biotin-containing linker via click chemistry. Proteins, which were in this way irreversibly attached to a biotin molecule, were enriched on avidin beads, which bind biotins via affinity-based interaction. Following tryptic digest the samples were measured by LC-MS/MS and analyzed using MaxQuant and Perseus. We identified type I signal peptidase (SpsB), an essential serine-protease, as a possible protein target of this compound class (FIG. 3). Further in vitro experiments will be conducted to biochemically validate SpsB as the molecular target of sorafenib and related compounds.

For overnight culture 5 mL of B medium (1% peptone, 0.5% NaCl, 0.5% yeast extract, 0.1% K2HPO4, pH 7.5) were inoculated with 50 µL of a cryostock (1:100) and incubated by shaking at 37° C. (200 rpm) for 14 h. The overnight culture was diluted 1:10 into 100 mL B medium. After 7 h growth an equivalent of OD$_{600}$=20 of the culture was harvested at 6000×g and 4° C. for 10 min and washed with PBS. Cells were resuspended in 0.5 mL PBS. For competition experiments samples were incubated with 0.5 mM sorafenib in DMSO or DMSO only as control (final concentration of 1%) for 45 min at 25° C. and 700 rpm. After preincubation 50 µM photoprobe X17PP1 in DMSO or DMSO as control (final concentration of 2%) were added and incubated for another 45 min at 25° C. and 700 rpm. After compound treatment samples were diluted in 4 mL PBS, transferred to petri dishes and irradiated with UV light at 360 nm (Philips TL-D BLB UV) for 30 min on ice. The suspension was transferred to falcons and bacteria were harvested by centrifugation at 6000×g and 4° C. for 10 min and washed with PBS.

Cell pellets were resuspended in 0.5 mL PBS with 1×EDTA-free Complete mini protease inhibitors (Roche) on ice and transferred to Precellys Glass/Ceramic Kit SK38 2.0 mL tubes. Cells were lysed with a Precellys®24 Homogenizer (Bertin Technologies, Montigny-le-Bretonneux, France) (at 5500 rpm for 15 s. Lysis was performed 6 times with 2 min cooling breaks on ice after each run. 300 µL of the lysates were transferred to 1.5 mL microcentrifuge tubes and treated with 8 µg/mL lysostaphin (Sigma) for 20 min at 37° C. and 700 rpm. Membranes were separated from cytosol by centrifugation for 1 h at 4° C. and 21,000×g. Membrane fraction was then washed twice with PBS using an ultrasonic rod (Bandelin Sonopuls, Berlin, Germany) at 10% intensity for 10 s for resuspension. Protein concentrations were determined using bicinchoninic acid assay (Pierce BCA Protein assay kit, Thermo Fisher Scientific, Pierce Biotechnology, Rockford, IL, USA) and used for normalization.

For click chemistry 300 µL of membrane and cytosol fractions were treated with 60 µM Biotin-PEG$_3$-N$_3$ (CLK-AZ104P4-100, Jena Bioscience, Jena, Germany), 1 mM TCEP, 0.1 mM TBTA ligand and 1 mM CuSO$_4$. The samples were incubated for 1 h at RT in the dark. Subsequently proteins were precipitated using 1.2 mL of cold acetone over night at −80° C.

The precipitated proteins were centrifuged at 16900×g and 4° C. for 15 min and formed protein pellets were washed two times with 1 mL cold methanol (−80° C.). Resuspension was achieved by sonication (15 sec at 10% intensity with an ultrasonic rod). Pellets were resuspended in 0.5 mL 0.4% SDS in PBS at RT by sonication (15 sec at 10% intensity). For enrichment 50 µL avidin-agarose beads (Sigma) were prepared by washing the three times with 1 mL 0.4% (w/v) SDS in PBS. Protein solution were added to the washed avidin-agarose beads and incubated under continuous inverting at 20 rpm and RT for 1 h. Beads were washed three times with 1 mL 0.4% SDS in PBS, two times with 1 mL 6 M urea in water and three times with 1 mL PBS. All centrifugation steps were conducted at 400 g for 2 min at RT.

The beads with bound proteins were resuspended in 200 µl denaturation buffer (7 M urea, 2 M thiourea in 20 mM pH 7.5 HEPES buffer). Proteins were reduced on-bead with 5 mM TCEP at 37° C. and 1200 rpm for 1 h. Subsequent alkylation was performed with 10 mM Iodoacetamide at 25° C. and 1200 rpm for 30 min in the dark. Alkylation was quenched by the addition of 10 mM dithiothreitol for 30 min at RT. For digestion 1 µL LysC (0.5 µg/µL) (Wako Pure Chemical Industries, Richmond, VA, USA) was added to each sample and incubated at RT and 1200 rpm for 2 h.

Afterwards samples were diluted 1:4 with 50 mM TEAB and digested with 1.5 μL trypsin (0.5 μg/μL) (Promega Sequencing Grade Modified, Promega, Madison, WI, USA) over night at 37° C. The reaction was stopped by adding formic acid (FA) to a final concentration of 0.5% (final pH of 2-3). Peptides were desalted and labelled by stable isotope dimethyl labeling (Boersema P. J. et al., Nat protoc 2009, 4 (4), 484-94)) on-column using 50 mg SepPak C18 columns (Waters). For this SepPak C18 columns were equilibrated with 1 mL acetonitrile, 1 mL elution buffer (80% ACN, 0.5% FA) and 3×1 mL aqueous 0.5% FA solution. Subsequently the samples were loaded by gravity flow, washed with 5×1 mL aqueous 0.5% FA solution and labeled with 5 mL of the respective dimethyl labeling solution. The following solutions were used: 30 mM $NaBH_3CN$, 0.2% $CH_2O$, 10 mM $NaH_2PO_4$, 35 mM $Na_2HPO_4$, pH 7.5 (light (L)), 30 mM $NaBH_3CN$, 0.2% $CD_2O$, 10 mM $NaH_2PO_4$, 35 mM $Na_2HPO_4$, pH 7.5 5 (light (M)) and 30 mM $NaBHD_3CN$, 0.2% $^{13}CD_2O$, 10 mM $NaH_2PO_4$, 35 mM $Na_2HPO_4$, pH 7.5 5 (heavy (H)). For technical replicates the labels were permuted. Labeled peptides were eluted with 500 μL of elution buffer, mixed for quantification and lyophilized using a vacuum centrifuge.

Prior to mass spectrometry samples were dissolved in 0.5% FA and filtered using 0.45 μm centrifugal filter units (VWR). Samples were analyzed via HPLC-MS/MS using an UltiMate 3000 nano HPLC system (Dionex, Sunnyvale, California., USA) equipped with Acclaim C18 PepMap100 75 μm ID×2 cm trap and Acclaim C18 PepMap RSLC, 75 μM ID×15 cm separation columns coupled to an Orbitrap Fusion (Thermo Fisher Scientific Inc., Waltham, Massachusetts, USA). Peptides were loaded on the trap and washed for 10 min with 0.1% formic acid, then transferred to the analytical column and separated using a 120 min gradient from 3% to 25% acetonitrile (Orbitrap Fusion) in 0.1% formic acid and 5% dimethyl sulfoxide (at 200 nL/min flow rate). LTQ Orbitrap Fusion was operated in a 3 second top speed data dependent mode. Full scan acquisition was performed in the orbitrap at a resolution of 120000 and an ion target of 4e5 in a scan range of 300-1700 m/z. Monoisotopic precursor selection as well as dynamic exclusion for 60 s were enabled. Precursors with charge states of 2-7 and intensities greater than 5e3 were selected for fragmentation. Isolation was performed in the quadrupole using a window of 1.6 m/z. Precursors were collected to a target of 1e2 for a maximum injection time of 250 with "inject ions for all available parallelizable time" enabled ("Universal" method, Eliuk et al, Thermo Scientific Poster Note PN40914). Fragments were generated using higher-energy collisional dissociation (HCD) and detected in the ion trap at a rapid scan rate. Internal calibration was performed using the ion signal of fluoranthene cations (EASY-ETD/IC source).

Peptide and protein identifications were performed using MaxQuant 1.5.1.2 software with Andromeda as search engine using following parameters: Carbamidomethylation of cysteines as fixed and oxidation of methionine as well as acetylation of N-termini as dynamic modifications, trypsin/P as the proteolytic enzyme, 4.5 ppm for precursor mass tolerance (main search ppm) and 0.5 Da for fragment mass tolerance (ITMS MS/MS tolerance). Searches were performed against the Uniprot database for S. aureus NCTC 8325 (taxon identifier: 93061, downloaded on 8.5.2014). Quantification was performed using dimethyl labeling with the following settings: light: DimethLys0, DimethNter0; medium: DimethLys4, DimethNter4 and heavy: DimethLys8, DimethNter8 with a maximum of 4 labeled amino acids. Variable modifications were included for quantification. The "I=L", "requantify" and "match between runs" (default settings) options were used. Identification was done with at least 2 unique peptides and quantification only with unique peptides.

For statistics with Perseus 1.5.1.6 three biological replicates consisting of three technical replicates each were analysed. Putative contaminants, reverse hits and proteins, identified by side only, were removed. Dimethyl labeling ratios were log 2(x) transformed and filtered to contain at least two valid values within technical replicates. Ratios were z-score normalized and average values of technical replicates were calculated. P-values were obtained by a two sided one sample t-test over the three biological replicates.

3.6 SpsB FRET with Membrane Fraction

Cells were grown according to stationary phase, harvested (12.000×g, 10 min, 4° C.), digested with lysostaphin (end conc: 20 U/mL, 37° C., 1 h) and sonicated (30 s, 20%, Bandelin Sonoplus, Berlin, Germany). Intact cells and debris were removed by centrifugation: 12.000×g, 10 min, 4° and membranes collected: 39.000×g, 75 min, 4° C. Membranes were resuspended in 2 mL cold 50 mM sodium phosphate buffer pH 7.5 and protein concentration determined by BCA (Roti®-Quant universal, Carl Roth GmbH+ Co. KG, Karlsruhe, Germany) assay.

0.1 mg/mL membranes in 50 mM sodium phosphate buffer pH 7.5 were used for the FRET (Förster resonance energy transfer) assay and incubated with 1 μL compound (in DMSO) and 10 μM SPase I FRET substrate (Sequence of SceD peptide): DABCYL-AGHDAHASET-EDANS (Protein AGHDAHASET has SEQ ID NO. 1, DABCYL: 4-(4-dimethylaminophenylazo)benzoic acid; EDANS: 5-((2-aminoethyl)amino)-1-naphthalenesulfonic acid, Anaspec Inc., Fremont, CA, USA). Fluorescence turnover was determined on a TECAN plate reader (Tecan infinite 200Pro, Tecan Group Ltd., Zurich, Switzerland) at 37° C. using 340 nm as excitation and 510 nm as emission wavelengths in fluorescence top reading mode.

Figure 7:
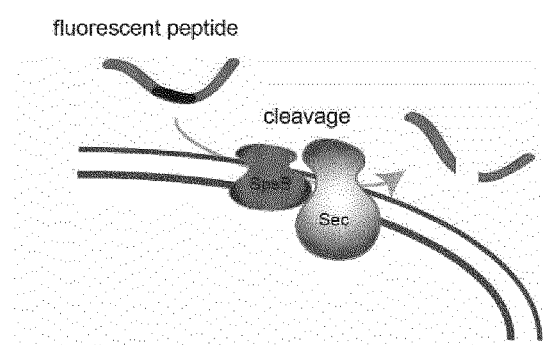
FIG. 7: A) Scheme of the fluorescent peptidase assay. A quenched fluorescent substrate (indicated in green) is cleaved by membrane bound SpsB resulting in dequenching of the donor and detectable fluorescence at 510 nm. This assay monitors SpsB activity. B) Principle of the Förster resonance energy transfer assay. DABCYL: 4-(4-dimethyl-aminophenylazo)benzoic acid; EDANS: 5-((2-aminoethyl)amino)-1-naphthalenesulfonic acid. C) Incubation of SpsB with sorafenib (100 µM) and PK/X17-1-150 (100 µM) stimulates peptidase activity and enhance substrate cleavage resulting in higher fluorescence at 510 nm compared to DMSO treated control. SpsB: Signal peptidase IB enzyme. Sec: proteins involved in secretion by translocation of substrates through the membrane.
Figure 7:
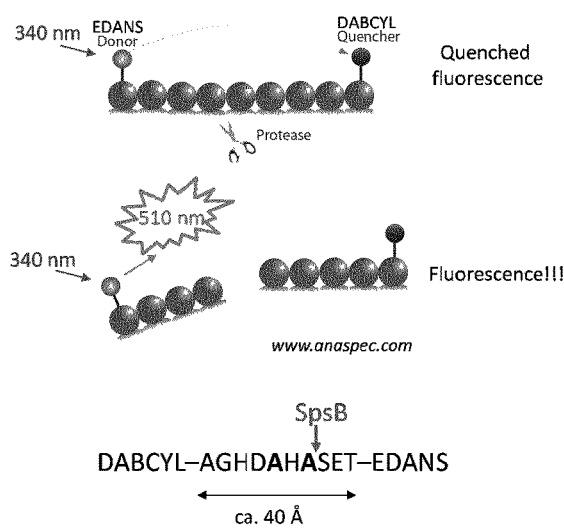
Figure 7:
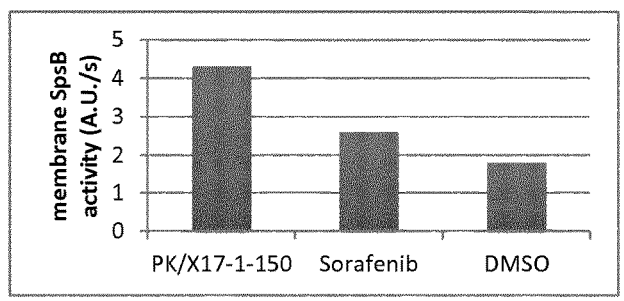
Figure 7:
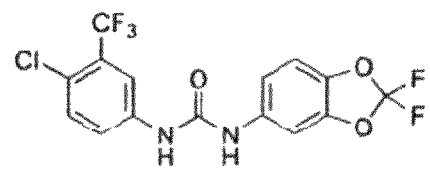

Addition of sorafenib and PK/X17-1-150 increased SpsB peptidase activity (FIG. 7A-C) demonstrating that binding to the enzyme stimulates substrate turnover.

3.7) Analysis of S. aureus NCTC8325 Secretome after Treatment with Sorafenib

The following protocol is based on the publication from Schallenberger et al. (Schallenberger, M. A.; Niessen, S.; Shao, C.; Fowler B. J.; Romesberg, F. E.; J Bacteriol 2012, 194 (10), 2677-2686). For overnight cultures 50 mL of B medium (1% peptone, 0.5% NaCl, 0.5% yeast extract, 0.1% K2HPO4, pH 7.5) were inoculated with 50 μL of a cryostock (1:100) and incubated by shaking at 37° C. (200 rpm) for 16 h. The overnight culture was diluted to $OD_{600}$ of 0.1 into 40 mL B medium per biological replicate. After 5 h growth at 37° C. $OD_{600}$ were measured, cells harvested by centrifugation at 3000×g and 4° C. for 15 min and washed with PBS. Cells were resuspended in fresh B medium to a cell density of ca. 1.5×10⁹ CFU/mL. 10 mL of the cells were incubated with 0.5×MIC of PK/X17-1-150 (0.15 μM) or sorafenib (1.5 μM) or DMSO as control in 50 mL tubes for 1.5 h at 37° C. (200 rpm). After treatment $OD_{600}$ were measured and serial dilutions plated for cell number determination. Cells were pelleted by centrifugation at 3000×g for 15 min and 6000×g for 5 min. The supernatants were collected and filtered (0.22 μM filter). Subsequently proteins were precipitated using 20% (wt/vol) trichloroacetic acid and an overnight incubation @ 4° C. Proteins were harvested by centrifugation at 9000×g, and washed two times with 90% acetone. Protein pellets were air dried and dissolved in 8 M urea in 50 mM Tris pH 8.0. Protein concentrations were measured using BCA assay (Pierce BCA Protein assay kit, Thermo Fisher Scientific, Pierce Biotechnology, Rockford, IL, USA). Protein concentrations were normalized according to protein concentrations (as determined by BCA assay), as no change in cell numbers at 0.5×MIC could be observed.

Proteins were reduced with 10 mM TCEP at 37° C. and 1200 rpm for 1 h. Subsequent alkylation was performed with 12.5 mM Iodoacetamide at 25° C. and 1200 rpm for 30 min in the dark. Alkylation was quenched by the addition of 12.5 mM dithiothreitol for 30 min at RT. For digestion 2 µL LysC (0.5 µg/µL) was added to each sample and incubated at RT and 700 rpm for 2 h. Afterwards samples were diluted 1:5 with 50 mM TEAB and digested with 2 µL trypsin (0.5 µg/µL) over night at 37° C. The reaction was stopped by adding formic acid (FA) to a final concentration of 0.5% (final pH of 2-3). Peptides were desalted on-column using 50 mg SepPak C18 columns (Waters). For this SepPak C18 columns were equilibrated with 1 mL acetonitrile, 1 mL elution buffer (80% ACN, 0.5% FA) and 3×1 mL aqueous 0.5% FA solution. Subsequently the samples were loaded by gravity flow, washed with 3×1 mL aqueous 0.5% FA solution, eluted with 500 µL of elution buffer and lyophilized using a vacuum centrifuge.

Prior to mass spectrometry samples were dissolved in 0.5% FA and filtered using 0.45 µm centrifugal filter units (VWR). Samples were analyzed via HPLC-MS/MS using an UltiMate 3000 nano HPLC system (Dionex, Sunnyvale, California, USA) equipped with Acclaim C18 PepMap100 75 µm ID×2 cm trap and Acclaim C18 PepMap RSLC, 75 µM ID×15 cm separation columns coupled to an Orbitrap Fusion (Thermo Fisher Scientific Inc., Waltham, Massachusetts, USA). Peptides were loaded on the trap and washed for 10 min with 0.1% formic acid, then transferred to the analytical column and separated using a 120 min gradient from 3% to 25% acetonitrile (Orbitrap Fusion) in 0.1% formic acid (at 200 nL/min flow rate). LTQ Orbitrap Fusion was operated in a 3 second top speed data dependent mode. Full scan acquisition was performed in the orbitrap at a resolution of 120000 and an ion target of 4e5 in a scan range of 300-1700 m/z. Monoisotopic precursor selection as well as dynamic exclusion for 60 s were enabled. Precursors with charge states of 2-7 and intensities greater than 5e3 were selected for fragmentation. Isolation was performed in the quadrupole using a window of 1.6 m/z. Precursors were collected to a target of 1e2 for a maximum injection time of 250 with "inject ions for all available parallelizable time" enabled ("Universal" method, Eliuk et al, Thermo Scientific Poster Note PN40914). Fragments were generated using higher-energy collisional dissociation (HCD) and detected in the ion trap at a rapid scan rate. Internal calibration was performed using the ion signal of fluoranthene cations (EASY-ETD/IC source).

Peptide and protein identifications were performed using MaxQuant 1.5.1.2 software with Andromeda as search engine using following parameters: Carbamidomethylation of cysteines as fixed and oxidation of methionine as well as acetylation of N-termini as dynamic modifications, trypsin/P as the proteolytic enzyme, 4.5 ppm for precursor mass tolerance (main search ppm) and 0.5 Da for fragment mass tolerance (ITMS MS/MS tolerance). Searches were performed against the Uniprot database for S. aureus NCTC 8325 (taxon identifier: 93061, downloaded on 8.5.2014). Quantification was performed using MaxQuant's LFQ algorithm. The "I=L", "requantify" and "match between runs" (default settings) options were used. Identification was done with at least 2 unique peptides and quantification only with unique peptides.

For statistics with Perseus 1.5.1.6 three biological were analysed. Putative contaminants, reverse hits and proteins, identified by side only, were removed. LFQ intensities were log 2(x) transformed and filtered to contain at least one valid value. Data was filtered to contain at least two "MS/MS count" in all three replicates of either DMSO or compound treated samples or both. Protein ratios (0.5×MIC sorafenib/DMSO and 8×MIC sorafenib/DMSO) were calculated and z-score normalized. P-values were obtained by a two sided one sample t-test over the three biological replicates.

Figure 8:
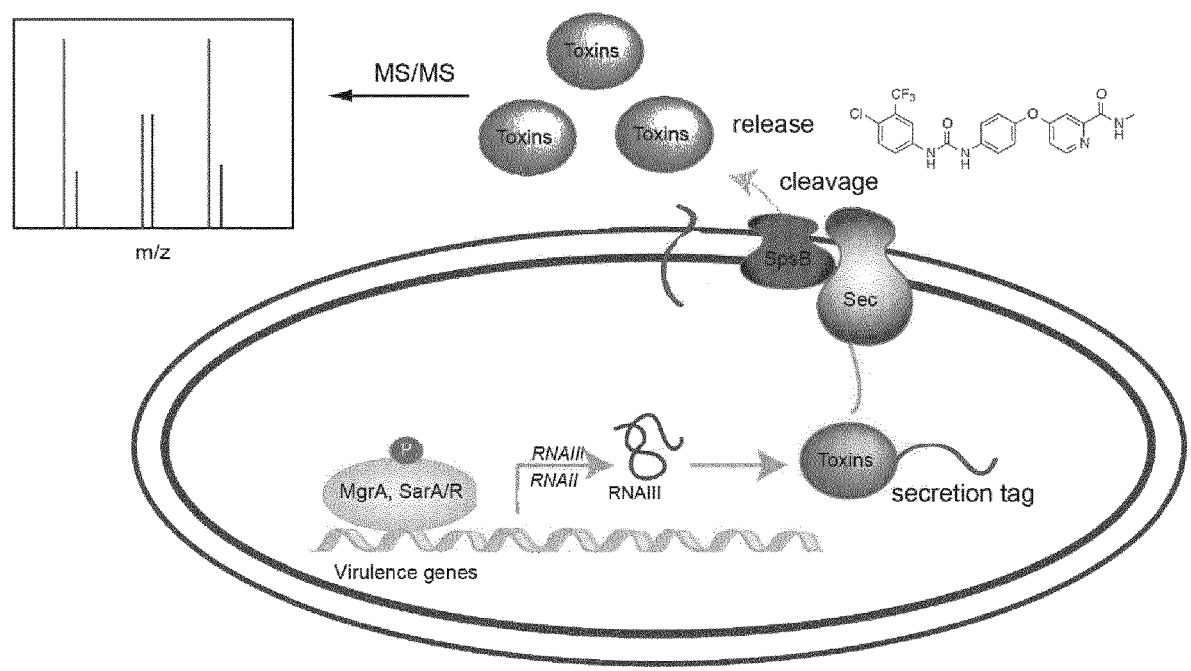
FIG. 8: Scheme of secretome (secreted proteins) analysis. Extracellular proteins of PK/X17-1-150 (example compound 4) treated and untreated cells are isolated and identified by massspectrometric (MS/MS) analysis. Many of these secreted proteins are toxins which are produced by bacteria in response to quorum sensing induced by the binding of autoinducing peptides (AIP). MgrA/SarA/R: transcriptional regulators of *S. aureus* genes.
Figure 9:
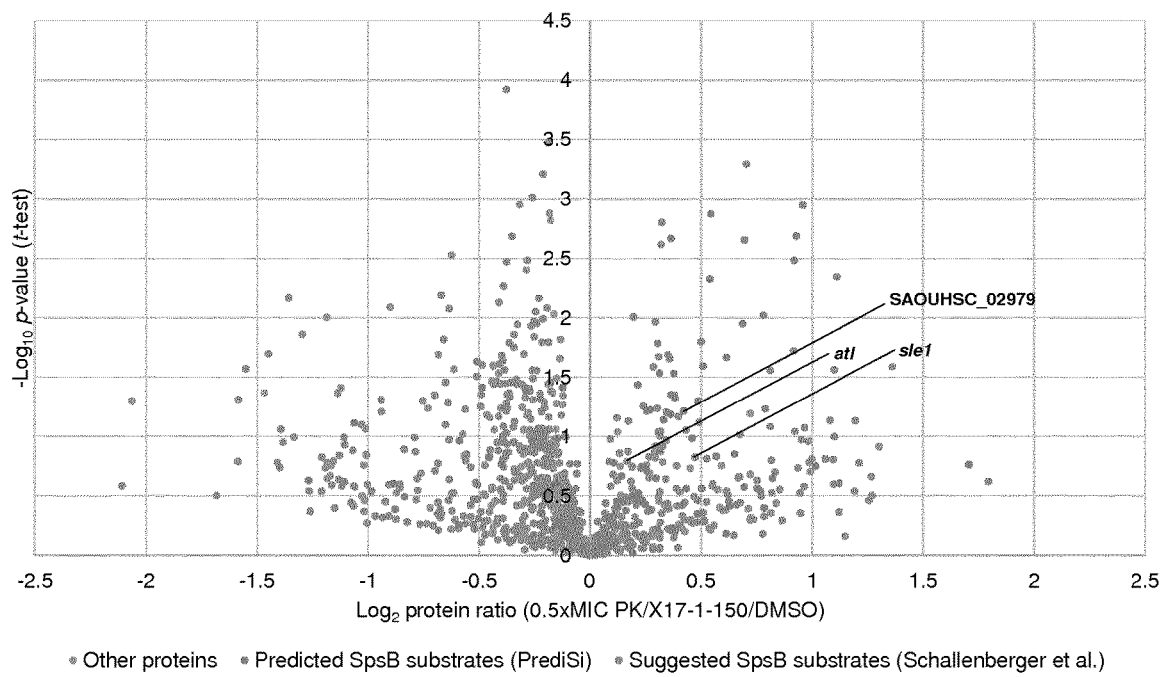
FIG. 9: A) Analysis of secretome at 0.5×MIC of PK/X17-1-150 vs DMSO. Essential cell wall biosynthesis proteins are among the processed proteins. B) Analysis of secretome at 0.5×MIC of sorafenib vs DMSO. Several known (depicted in red, Schallenberger, M. A.; Niessen, S.; Shao, C.; Fowler B. J.; Romesberg, F. E. *J. Bacteriol* 2012, 194 (10), 2677-2686) and predicted (by PrediSi, in blue) SpsB substrates are secreted which is in line with the stimulation of SpsB. SpsB: Signal peptidase IB enzyme.
Figure 9:
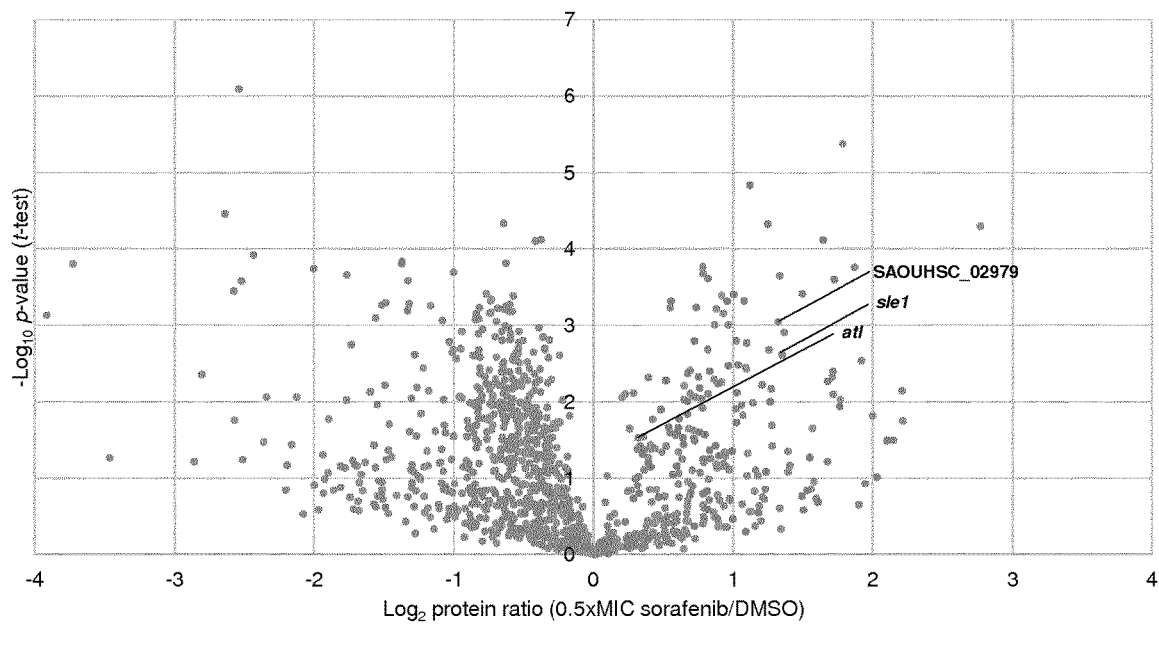

In agreement with results of the FRET peptidase assay (FIG. 7) stimulation of protein secretion was also obtained in whole cells upon incubation with 0.5×MIC of PK/X17-1-150 or sorafenib (FIG. 8). Analysis of the secretome (sum of all secreted proteins) revealed a strong increase of extracellular proteins which are predicted SpsB substrates.

3.8) Minimum Biofilm Eradication Concentration (MBEC)

To each well of a flat-bottomed 96-well plate (BD Biosciences, BD 351172) 200 µL of overnight culture of bacteria diluted 1:100 in media is added. Plates are incubated for 24 hours at 37° C. to establish biofilms. After 24 hours, the wells are carefully emptied by inverting the plate and gently shaking. A pre-mixed solution of media and compound stock solution is added to each well and plates are incubated at 37° C. At 16 hours after pre-established biofilms are treated with compound, the media from each well is removed, biofilms are washed three times with 200 µL PBS to remove planktonic cells, and biofilms are regrown overnight at 37° C. in 200 µL of fresh media. 100 µL of supernatant from each well are transferred to a fresh 96-well flat bottomed plate and the OD at 595 nm is measured using a plate reader (POLARstar Omega, BMG Labtech). Concentrations of compound yielding a regrown OD of less than 0.1 correspond to the MBEC. Six replicates are completed for each concentration of compound as well as positive and negative controls.

Figure 10A:
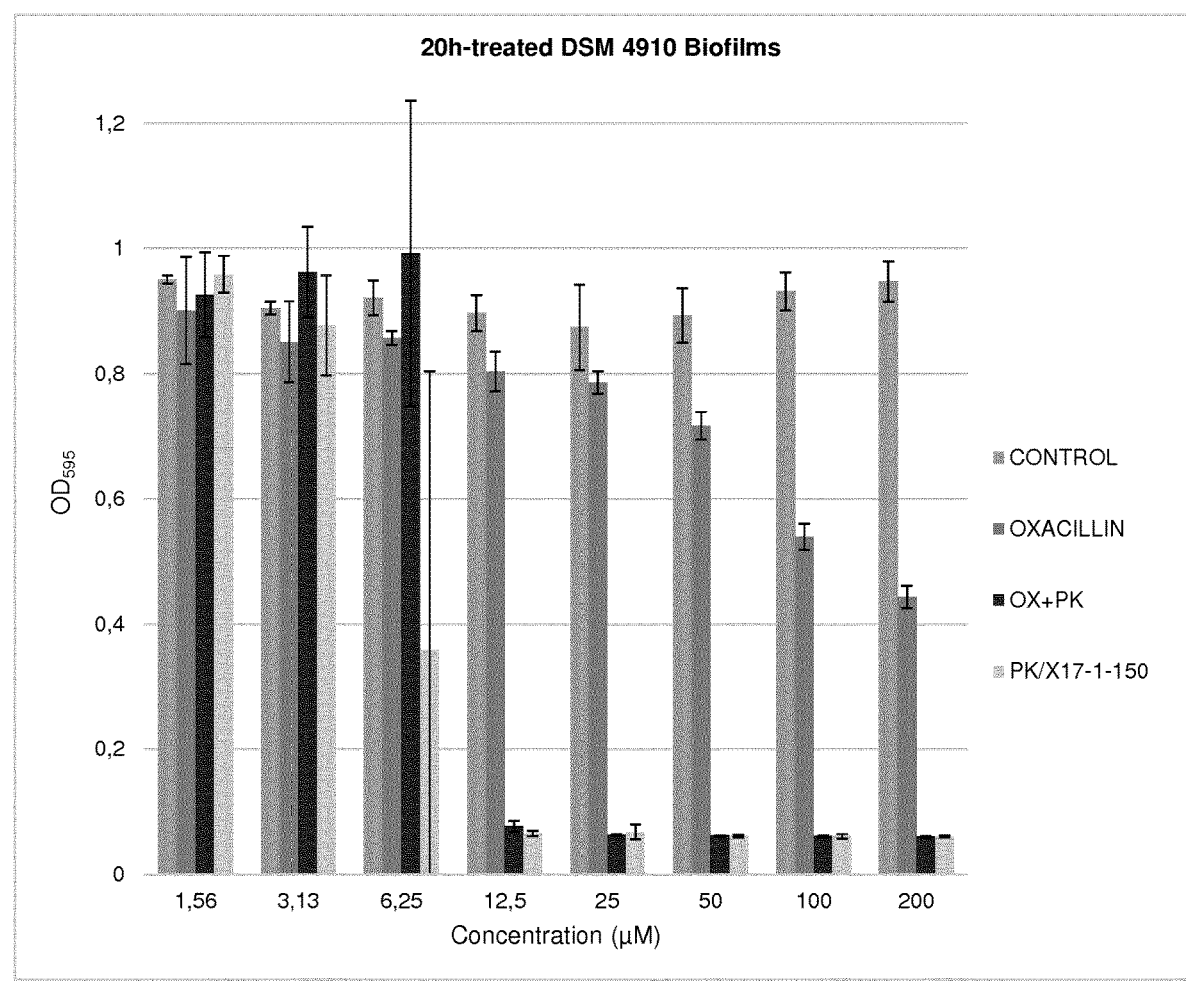
FIG. 10: A) Concentration dependent biofilm eradication effect of PK/X17-1-150 on *S. aureus* DSM 4910 (NCTC 8325) after 20 h of compound treatment. Additional experiments were carried out in absence of compound (control), with oxacillin as marketed drug for comparison and with a combined treatment of oxacillin and PK/X17-1-150 (Ox+PK). Importantly, PK/X17-1-150 revealed the strongest effect. B) Concentration dependent biofilm eradication effect of PK/X17-1-150 on *S. aureus* DSM 4910 (NCTC8325) after 70 h of compound treatment. Additional experiments were conducted as outlined in FIG. 10A. Here, again PK/X17-1-150 and combination OX+PK revealed most potent effects.

The results are shown in FIG. 10A, which shows the concentration dependent biofilm eradication effect of PK/X17-1-150 on S. aureus DSM 4910 after 20 h of compound treatment. DMSO was used as negative control compound, Oxacillin was used as positive control compound. Levels of crystal violet retained were measured spectrophotometrically at an OD of 595 nm. Concentrations of compound yielding a regrown OD of less than 0.1 correspond to the MBEC. Six replicates are completed for each concentration of compound as well as controls. PK/X17-1-150 revealed the strongest effect.

Figure 10B:
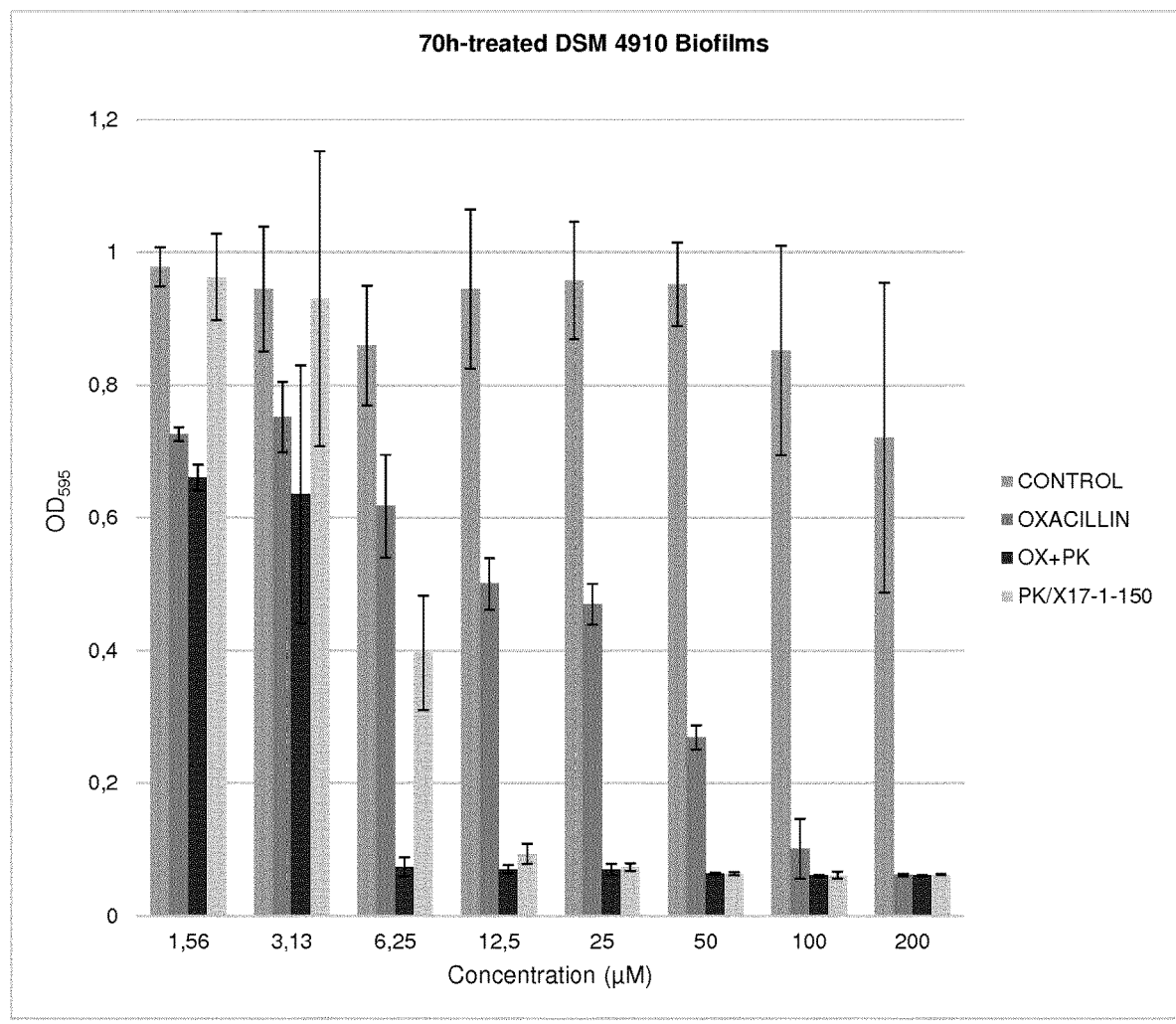

Similar results are shown in FIG. 10B, which show concentration dependent biofilm eradication effect of PK/X17-1-150 on S. aureus DSM 4910 after 70 h of compound treatment. DMSO was used as negative control compound, Oxacillin was used as positive control compound. Levels of crystal violet retained were measured spectrophotometrically at an OD of 595 nm. Concentrations of compound yielding a regrown OD of less than 0.1 correspond to the MBEC. Six replicates are completed for each concentration of compound as well as controls. PK/X17-1-150 and the combination Ox+PK revealed most potent effects.

3.9) Animal Model Data

Figure 11A:
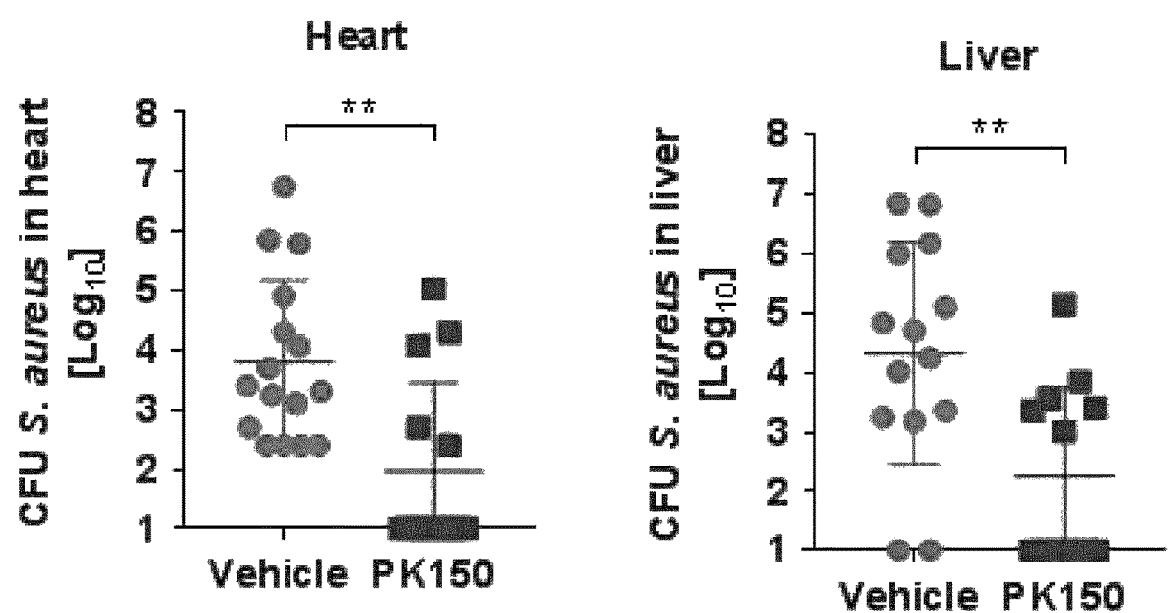
FIG. 11: A) Efficacy of PK/X17-1-150 against *S. aureus* in a murine bloodstream infection model. Bacterial loads in heart (left) and liver (right) were both significantly reduced by 2 log cfu compared to the vehicle control. B) Efficacy of PK/X17-1-150 and levofloxacin against MRSA ATCC 33951 in the neutropenic murine thigh model. A 1-$\log_{10}$ cfu/g thigh reduction was observed in PK/X17-1-150-treated mice in comparison with sham-treated mice. The same range of reduction was determined for mice treated with the positive control levofloxacin upon i.v. administration.

FIG. 11A shows the efficacy of PK/X17-1-150 against S. aureus in a murine bloodstream infection model. Bacterial loads in the heart (left) and liver (right) of S. aureus-infected mice treated with 20 mg/kg of PK/X17-1-150 (squares) or vehicle alone (circles). Each symbol represents an individual mouse. Compilation data from three independent experiments are presented. N=14 for vehicle and PK/X17-1-150.

Horizontal lines represent the mean values. **, p<0.01. Bacterial loads in heart (left) and liver (right) were both significantly reduced by 2 log cfu compared to the vehicle control.

Figure 11B:
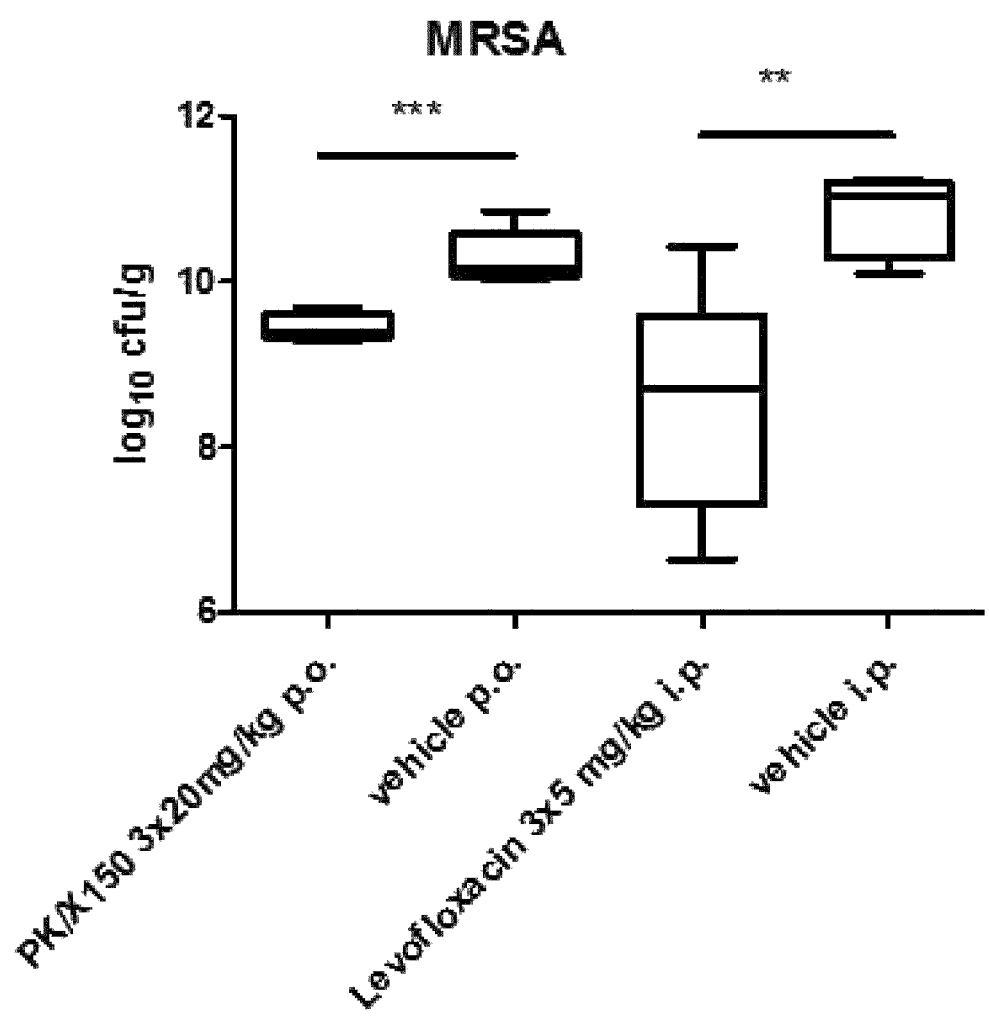
Figure 12A:
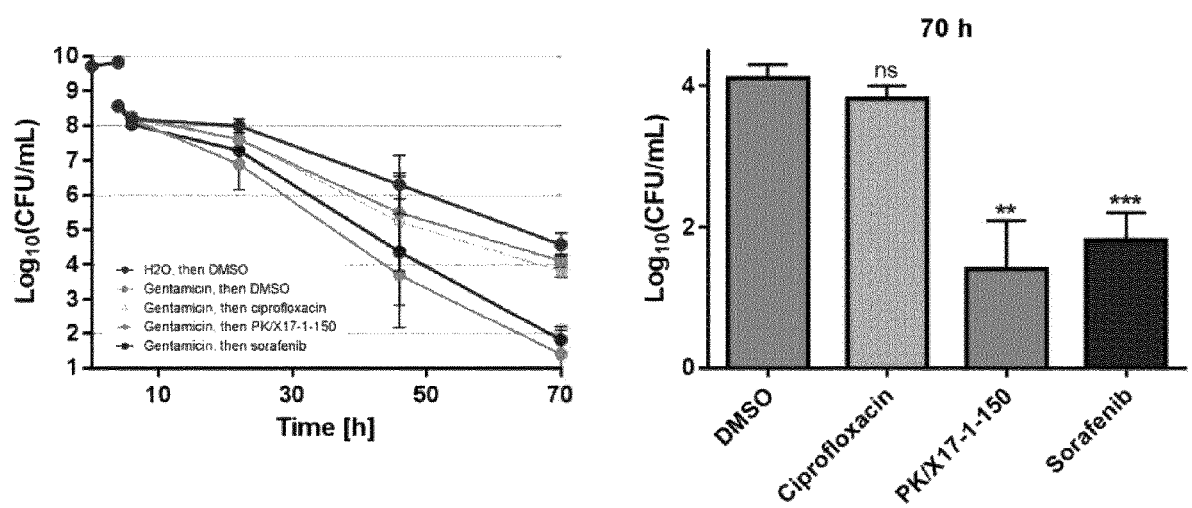
FIG. 12.
Figure 12B:
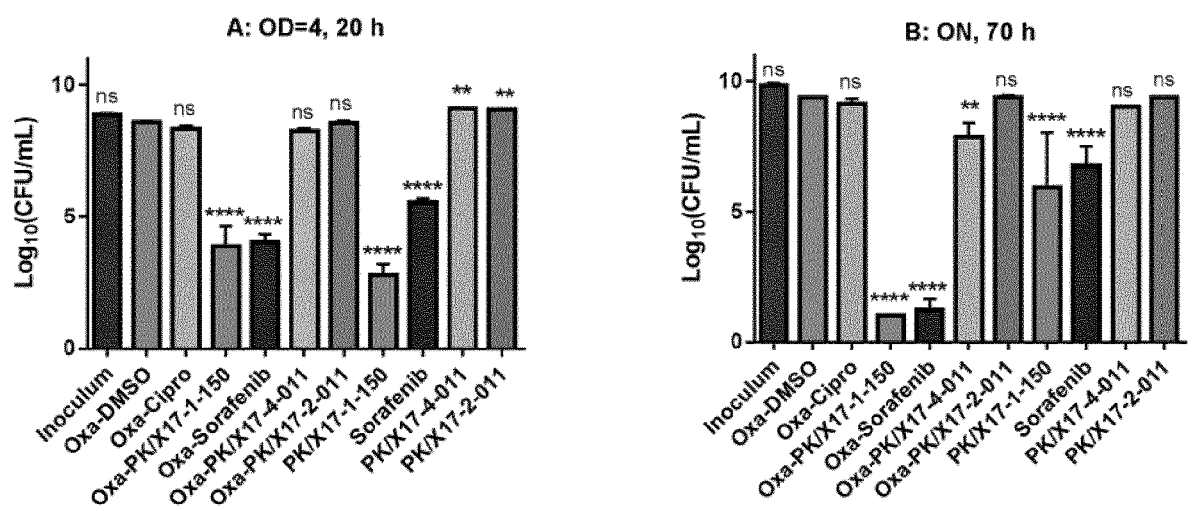
Figure 13:
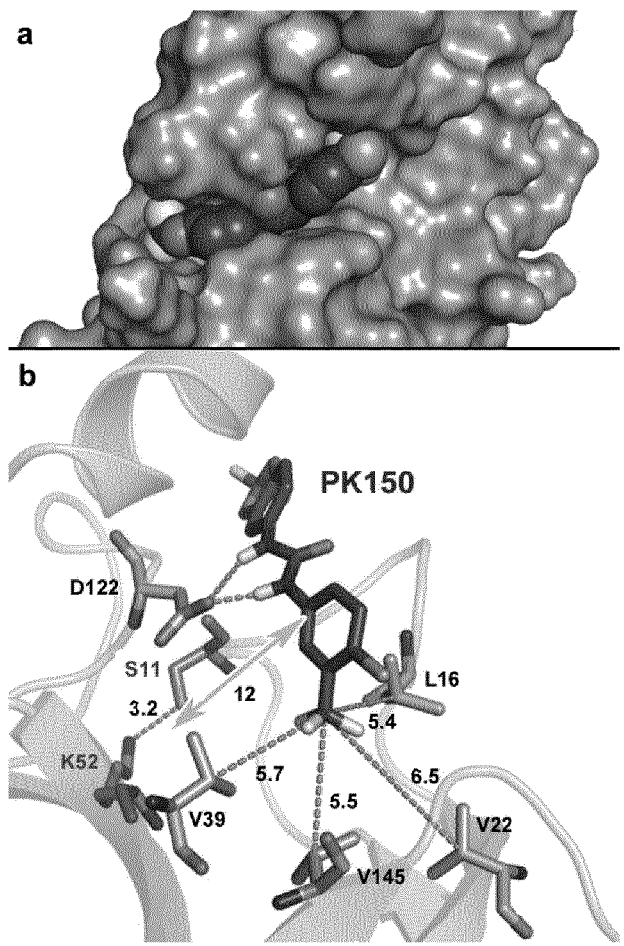

FIG. 11B shows the efficacy of PK/X17-1-150 and levofloxacin against MRSA ATCC 33591 in the neutropenic murine thigh model. PK/X17-1-150 (20 mg/kg) and the corresponding vehicle were administered orally after 30 min, 4 and 8 h after bacterial inoculation, whereas levofloxacin (5 mg/kg) and the corresponding vehicle were administered intraperitoneally after 2, 6 and 10 h after bacterial inoculation. N=6 for vehicle i.p., levofloxacin i.p. and for PK/X17-1-150; n=5 for vehicle p.o. Data are expressed as mean values±SD. , p<0.01; *, p<0.001. A 1-$\log_{10}$ cfu/g thigh reduction was observed in PK/X17-1-150-treated mice in comparison with sham-treated mice. The same range of reduction was determined for mice treated with the positive control levofloxacin upon i. v. administration.

3.10) Data Obtained with Persister Cells

As the generation and treatment of persister cells is highly dependent on the conditions and there is no consistency in the scientific community, two assays with different conditions were performed to corroborate effects resulting from PK/X17-1-150 treatment.

Persister cell assay I. S. aureus NCTC 8325 cells were inoculated from an exponentially growing culture at $OO_{600}$=0.4-0.5 1:1000 into tryptic soy broth (TSB, 17 g/L casein peptone, pancreas hydrolysate, 3 g/L soy peptone (papain hydrolysate), 2.5 g/L di-Potassium hydrogen phosphate, 5 g/L sodium chloride, 2.5 g/L glucose monohydrate, pH 7.3±0.2; CASO Broth, Carl Roth GmbH+Co. KG) and grown for exactly 15 h at 37° C. and 200 rpm. Cells were serially diluted and plated to determine cell numbers before any treatment. Persisters were prepared by treating the culture with 20 μg/mL gentamicin (40×MIC in NCTC 8325) for 4 h at 37° C. and 200 rpm. An $H_2O$-treated control culture was incubated in the same way. Persisters (and control cells) were washed three times with PBS (5000×g, 5 min) and diluted to $OD_{600}$=4 in PBS. Serial dilutions were prepared for plating and determination of CFU/mL. 8×MIC concentrations of PK/X17-1-150 (2.4 μM) and sorafenib (24 μM) and 5 μg/mL ciprofloxacin (20×MIC) as negative control were added 1:1000 to 10 mL aliquots of the diluted persisters in 100 mL flasks and incubated at 37° C. and 200 rpm for 70 h. At indicated times cells from 1 mL samples were harvested (10000×g, 3 min), washed with PBS to remove the compound and resuspended in 1 or 0.1 mL PBS for the determination of CFU/mL by plating serial dilutions on agar plates. Three biological replicates were prepared and means, standard deviations and p-values (unpaired parametric t-test) were determined with Prism (GraphPadPrism v6.05, GraphPad Software). After 70 h there is a significant reduction of viable cells for PK/X17-1-150 and Sorafenib treated cells compared to the DMSO control, whereas there is no change for the ciprofloxacin-treated control.

Persister cell assay II. Tryptic soy broth (50 mL in 250 mL culture flasks) was inoculated 1:1000 with overnight cultures of NCTC 8325 and grown at 37° C. and 200 rpm until an $OD_{600}$ of 4 was reached or overnight (ON). Serial dilution were prepared and plated to determine the cell numbers in the inoculum. The cultures were aliquoted a 1 mL and treated with 30 μg/mL oxacillin (30×MIC) combined with 8×MIC of test compounds (2.4 μM PK/X17-1-150 or PK/X17-4-011, 24 μM sorafenib or PK/X17-2-011). Additionally compounds were tested without oxacillin to exclude combinatory effects, as the majority of the cells at $OD_{600}$=4 and from overnight cultures already are persisters and do not require selection by oxacillin. After 20 h (A) or 70 h (B) of treatment, cells were harvested, washed two times with PBS (10000×g, 3 min), serially diluted and plated on agar plates for determination of surviving cell numbers.

There is a significant reduction of viable cells for PK/X17-1-150 and Sorafenib treated cells compared to the DSMO control, whereas there is no change observed for ciprofloxacin-, PK/X17-4-011- or PK/X17-2-011-treated controls.

3.11) Molecular Docking

1.) Preparation of the Systems

For the preparation of the systems, the signal peptidase crystal structure with the PDB code 4wvj was used for the simulations. The bound peptide was removed and the protein was solvated in a water box using tleap module of the Amber15 (Case, D. A.; J. T. B.; Betz, R. M.; Cerutti, D. S.; Cheatham, T. E. III; Darden, T. A.; Duke, R. E.; Giese, T. J.; Gohlke, H.; Goetz, A. W.; Homeyer, N.; Izadi, S.; Janowski, P.; Kaus, J.; Kovalenko, A.; Lee, T. S.; LeGrand, S.; Li, P.; Luchko, T.; Luo, R.; Madej, B.; Merz, K. M.; Monard, G.; Needham, P.; Nguyen, H.; Nguyen, H. T.; Omelyan, I.; Onufriev, A.; Roe, D. R.; Roitberg, A.; Salomon-Ferrer, R.; Simmerling, C. L.; Smith, W.; Swails, J.; Walker, R. C.; Wang, J.; Wolf, R. M.; Wu, X.; York D. M.; Kollman, P. A. *AMBER* 2015. In University of California, San Francisco.: 2015.) program package by applying a 12 Å buffer region around protein atoms (yielding a model consisting of ~30, 000 atoms).

2.) Molecular Dynamic Simulations

All simulations were performed using the ff03 (Duan, Y.; Wu, C.; Chowdhury, S.; Lee, M. C.; Xiong, G.; Zhang, W.; Yang, R.; Cieplak, P.; Luo, R.; Lee, T. *Journal of Computational Chemistry* 2003, 24, 1999-2012.), GAFF (Wang, J.; Wolf, R. M.; Caldwell, J. W.; Kollman, P. A.; Case, D. A. *J. Comput. Chem.* 2004, 25, 1157-1174.) and TIP3P (Jorgensen, W. L.; Chandrasekhar, J.; Madura, J. D.; Impey, R. W.; Klein, M. L. *The Journal of Chemical Physics* 1983, 79, 926-935.) force field parameters for the solute, PK/X17-1-150, and solvent, respectively. Missing bonded parameters for the probe were obtained using the antechamber package (Wang, J.; Wang, W.; Kollman, P. A.; Case, D. A. *Journal of Molecular Graphics and Modelling* 2006, 25, 247-260.) of Amber15, with the RESP charges calculated by the Gaussian09 software (Frisch, M. J.; Trucks, G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L. Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery Jr., J. A.; Peralta, J. E.; Ogliaro, F.; Bearpark, M. J.; Heyd, J.; Brothers, E. N.; Kudin, K. N.; Staroverov, V. N.; Kobayashi, R.; Normand, J. Raghavachari, K.; Rendell, A. P.; Burant, J. C.; Iyengar, S. S.; Tomasi, J.; Cossi, M.; Rega, N. Millam, N. J.; Klene, M.; Knox, J. E.; Cross, J. B.; Bakken, V.; Adamo, C.; Jaramillo, J. Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J. Dapprich, S.; Daniels, A. D.; Farkas, Ö.; Foresman, J. B.; Ortiz, J. V.; Cioslowski, J.; Fox, D. J. *Gaussian* 09, Gaussian, Inc.: Wallingford, CT, USA, 2009.). Prior to the minimization of the models, the density of the systems was adjusted to 1 g/cm³ using an in-house python script. Hydrogens and heavy atoms were minimized consecutively using the SANDER module of Amber15. Periodic boundary conditions were applied. Long-range electrostatic interactions were calculated using the particle mesh Ewald method (Essmann, U.; Perera, L.; Berkowitz, M. L.; Darden, T.; Lee, H.; Pedersen, L. G. *J. Chem. Phys.* 1995, 103, 8577-8593.). A non-bonded cutoff of 12 Å and a time step of 1 fs were used. The systems were heated up to 300 K in the NVT ensemble using a stepwise fashion as performed in our previous works (Marcinowski, M.; Rosam, M.; Seitz, C.; Elferich, J.; Behnke, J.; Bello, C.; Feige, M. J.; Becker, C. F.; Antes, I.; Buchner, J. *J. Mol. Biol.* 2013, 425, 466-474; Schneider, M.; Rosam, M.; Glaser, M.; Patronov, A.; Shah, H.; Back, K. C.; Daake, M. A.; Buchner, J.; Antes, I. *Proteins: Structure, Function, and Bioinformatics* 2016.). The SHAKE algorithm was used to constraint all bonds involving hydrogens (Ryckaert, J.-P.; Ciccotti, G.; Berendsen, H. J. *Journal of Computational Physics* 1977, 23, 327-341.). The production runs were performed in the NPT ensemble for 150 ns and 100 ns for the PK/X17-1-150 bound complex and the apo-protein, respectively. The cuda-enabled graphics processing units (GPUS) version of the pmemd module of Amber15 was used (Götz, A. W.; Williamson, M. J.; Xu, D.; Poole, D.; Le Grand, S.; Walker, R. C. *Journal of Chemical Theory and Computation* 2012, 8, 1542-1555; Salomon-Ferrer, R.; Gotz, A. W.; Poole, D.; Le Grand, S.; Walker, R. C. *Journal of Chemical Theory and Computation* 2013, 9, 3878-3888.).

3.) Docking and Binding Free Energy Calculations

A stepwise and comparative protocol was followed to find the binding site of the probe. Two plausible binding sites were detected using surface based analysis and analyzing their distances to the active site. The probe was docked to these two grooves separately, using the DynaDock approach of our in-house modeling program DynaCell (Antes, I. *Proteins: Structure, Function, and Bioinformatics* 2010, 78, 1084-1104.). The docking was performed in two steps; broad sampling and the molecular dynamic based energy refinement of the selected poses. The energetically-highest ranked five poses (total of ten poses coming from two different binding sites) were further simulated up to 5 ns using the same simulation scheme introduced above. The Molecular Mechanics-Generalized Born Surface Area approach (MMGBSA) (Srinivasan, J.; Cheatham, T. E.; Cieplak, P.; Kollman, P. A.; Case, D. A. *J. Am. Chem. Soc.* 1998, 120, 9401-9409.) was applied to calculate the binding free energies of these 10 complexes. The pose with the lowest binding free energy was chosen for further analysis. For the MMGBSA calculations, three distinct production runs (starting with different velocities) were performed on each equilibrated structure to yield 20 ns simulation time in total (time step 1 fs, a total of 225,000 complex frames (3×75,000). The MMGBSA.py module (Miller III, B. R.; McGee Jr, T. D.; Swails, J. M.; Homeyer, N.; Gohlke, H.; Roitberg, A. E. *J. Chem. Theory Comput.* 2012, 8, 3314-3321.) of Amber15 (Case, D.; Babin, V.; Berryman, J.; Betz, R.; Cai, Q.; Cerutti, D.; Cheatham III, T.; Darden, T.; Duke, R.; Gohlke, H. Proteins 2006, 65, 712-725.) was used to combine these frames and calculate the binding free energy. The contribution of the solvent was computed with Generalized Born Surface Area (GBSA) with a probe radius of 1.4 Å and the 'mbondi2' radii set (Srinivasan, J.; Trevathan, M. W.; Beroza, P.; Case, D. A. *Theoretical Chemistry Accounts: Theory, Computation, and Modeling (Theoretica Chimica Acta)* 1999, 101, 426-434.) using the modified GB model introduced by Case et al. (Onufriev, A.; Bashford, D.; Case, D. A. *The Journal of Physical Chemistry B* 2000, 104, 3712-3720; Onufriev, A.; Bashford, D.; Case, D. A. *Proteins: Structure, Function, and Bioinformatics* 2004, 55, 383-394.). The entropic contributions to the free energy of binding were not included in the calculation scheme as it has been shown that such costly computations do not significantly improve the results (Hou, T.; Wang, J.; Li, Y.; Wang, W. *J. Chem. Inf. Model.* 2010, 51, 69-82; Genheden, S. *J. Comput. Aided Mol. Des.* 2011, 25, 1085-1093; Genheden, S.; Ryde, U. *J. Chem. Theory Comput.* 2011, 7, 3768-3778.).

The invention claimed is:

1. A compound having a structure according to Formula II

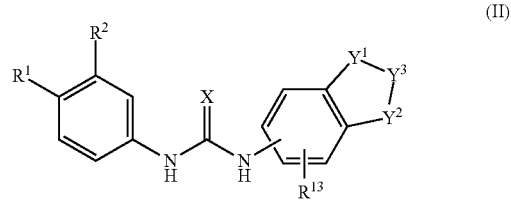

wherein $R^1$ is cyano or halogen;

$R^2$ is $(C_1\text{-}C_6)$alkyl or $(C_1\text{-}C_6)$ haloalkyl;

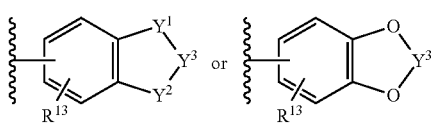

$R^{13}$ is selected from the group consisting of hydrogen, $(C_1-C_6)$alkyl, $(C_1-C_6)$ haloalkyl and halogen; and X is O or S;

or a pharmaceutically acceptable salt, solvate or hydrate thereof.

2. The compound according to claim 1, wherein said compound is 1-(4-chloro-3-(trifluoromethyl)phenyl)-3-(2,2-difluorobenzo [d][1,3]dioxol-4-yl) urea.

3. A kit comprising a compound according to claim 1 and at least one pharmaceutically acceptable carrier.

4. A method for disinfection wherein said method comprises contacting bacteria with a compound of claim 1.

5. A pharmaceutical composition, wherein said composition comprises a compound according to claim 1.

6. A method for the treatment of a bacterial disease, said method comprising administering a compound to a subject having been diagnosed with the bacterial disease, said compound having a structure according to Formula II

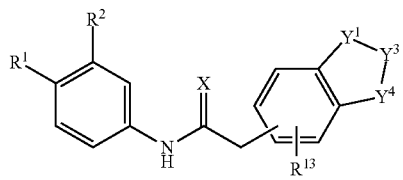

(II)

wherein $R^1$ is;

$R^2$ is $(C_1-C_6)$alkyl or $(C_1-C_6)$ haloalkyl;

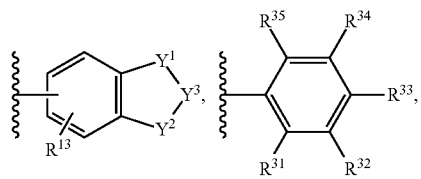

$R^{13}$ is selected from the group consisting of hydrogen, $(C_1-C_6)$alkyl, $(C_1-C_6)$ haloalkyl and halogen; and X is O or S;

or a pharmaceutically acceptable salt, solvate or hydrate thereof, wherein the bacterial disease is caused by at least one bacteria selected from the group consisting of *Listeria monocytogenes, Listeria welshimeri, Staphylococcus aureus,* MRSA and clinical isolates thereof, Vancomycin-intermediate *Staphylococcus aureus*, Vancomycin-resistant *Staphylococcus aureus, Staphylococcus haemolyticus, Staphylococcus hominis, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracis, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroids, Rhodococcus equi* and *Burkholderia thailandensis*.

7. The method according to claim 6, wherein $R^1$ is halogen; and $R^2$ is —$CH_3$ or —$CF_3$.

8. The method according to claim 6, wherein $R^1$ is chlorine; $R^2$ is-$CF_3$;

$R^{13}$ is hydrogen; and X is O.

9. The method according to claim 6, wherein

X is O.

10. A method for the treatment of a bacterial disease, said method comprising administering a compound to a subject having been diagnosed with the bacterial disease, said compound being selected from the group consisting of 1-(4-chloro-3-methylphenyl)-3-(2,2-difluorobenzo [d][1,3]dioxol-5-yl) urea, 1-(4-chloro-3-(trifluoromethyl)phenyl)-3-(2,2-difluorobenzo [d][1,3]dioxol-5-yl) urea, 1-(4-chloro-3-(trifluoromethyl)phenyl)-3-(2,2-difluorobenzo [d][1,3]dioxol-5-yl)thiourea, and 1-(4-chloro-3-(trifluoromethyl)phenyl)-3-(2,2-difluorobenzo [d][1,3]dioxol-4-yl) urea, wherein the bacterial disease is caused by at least one bacteria selected from the group consisting of *Listeria monocytogenes, Listeria welshimeri, Staphylococcus aureus,* MRSA and clinical isolates thereof, Vancomycin-intermediate *Staphylococcus aureus*, Vancomycin-resistant *Staphylococcus aureus, Staphylococcus haemolyticus, Staphylococcus hominis, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Bacillus licheniformis, Bacillus subtilis, Bacillus anthracis, Bacillus cereus, Bacillus thuringiensis, Bacillus larvae, Mycobacterium tuberculosis, Mycobacterium bovis, Mycobacterium leprae, Mycobacterium ulcerans, Mycobacterium kanasasii, Mycobacterium avium, Mycobacterium paratuberculosis, Mycobacterium scrofulaceam, Mycobacterium microti, Mycobacterium africanum, Mycobacterium canettii, Mycobacterium intracellulare, Mycobacterium simiae, Mycobacterium szulgai, Mycobacterium xenopi, Mycobacterium fortuitum, Mycobacterium chelonei, Mycobacterium marinum, Nocardia asteroids, Rhodococcus equi* and *Burkholderia thailandensis*.

* * * * *

```
                        SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Sequence of SceD peptide

<400> SEQUENCE: 1

Ala Gly His Asp Ala His Ala Ser Glu Thr
1               5                   10
```